(12) United States Patent
Buettelmann et al.

(10) Patent No.: US 7,538,132 B2
(45) Date of Patent: May 26, 2009

(54) ISOXAZOLO DERIVATIVES

(75) Inventors: Bernd Buettelmann, Schopfheim (DE); Bo Han, Shanghai (CN); Henner Knust, Rheinfelden (DE); Matthias Heinrich Nettekoven, Grenzach-Wyhlen (DE); Andrew William Thomas, Birsfelden (CH)

(73) Assignee: Hoffman-La Roche Inc., Nutley, NJ (US)

( * ) Notice: Subject to any disclaimer, the term of this patent is extended or adjusted under 35 U.S.C. 154(b) by 441 days.

(21) Appl. No.: 11/520,394

(22) Filed: Sep. 13, 2006

(65) Prior Publication Data

US 2007/0066668 A1    Mar. 22, 2007

(30) Foreign Application Priority Data

Sep. 19, 2005    (EP) .................... 05108599

(51) Int. Cl.
*A61K 31/422* (2006.01)
*C07D 261/06* (2006.01)
*C07D 413/02* (2006.01)

(52) U.S. Cl. ................ 514/378; 548/240; 548/247; 548/248

(58) Field of Classification Search ............. 548/240, 548/247, 248; 514/378
See application file for complete search history.

(56) References Cited

FOREIGN PATENT DOCUMENTS

| WO | WO 95/11885 | 5/1995 |
| WO | WO 02/22610 | 3/2002 |
| WO | WO 2005/056004 | 6/2005 |

OTHER PUBLICATIONS

Dattolo G et al, *Jour. of Heterocyclic Chem.*k 14 (1977) pp. 1021-1022 XP002418194.
Chemical Abstract Service, Columbus, OH XP002418197.
Chemical Abstract Service, Columbus, OH XP002418198.
McNamara et al., Psychobiology (1993), vol. 21, pp. 101-108.
Lam et al., Bioorganic & Medicinal Chemistry Letters (2003) vol. 13(10) pp. 1795-1799.
Wang et al., Journal of Fluorine Chemistry, vol. 111(2) pp. 241-246 (2001).
Roy et al., Synthesis, 2003 pp. 1347-1356.
White, et al., Journal of Organic Chemistry (1981), vol. 46(11) pp. 2273-2280.
Shi Shun et al., J. Org. Chem. vol. 68 (2003) pp. 6810-6813.

*Primary Examiner*—Golam M Shameem
(74) *Attorney, Agent, or Firm*—George W. Johnston; Patricia S. Rocha-Tramloni; Kimberly J. Prior

(57) ABSTRACT

The present invention is concerned with aryl-isoxazole-4-carbonyl-pyrrole-2-carboxylic acid amide derivatives of formula

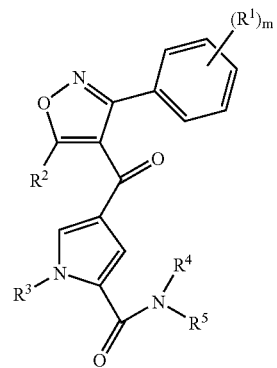

wherein
$R^1$, $R^2$, $R^3$, $R^4$, and $R^5$, and m are as defined herein and with their pharmaceutically acceptable acid addition salts.

This class of compounds have high affinity and selectivity for GABA A α5 receptor binding sites and therefore may be useful as cognitive enhancer or for the treatment of cognitive disorders like Alzheimer's disease.

32 Claims, No Drawings

ISOXAZOLO DERIVATIVES

PRIORITY TO RELATED APPLICATIONS

This application claims the benefit of European Application No. 05108599.1, filed Sep. 19, 2005, which is hereby incorporated by reference in its entirety.

BACKGROUND OF THE INVENTION

Receptors for the major inhibitory neurotransmitter, gamma-aminobutyric acid (GABA), are divided into two main classes: (1) GABA A receptors, which are members of the ligand-gated ion channel superfamily and (2) GABA B receptors, which are members of the G-protein linked receptor family. The GABA A receptor complex which is a membrane-bound heteropentameric protein polymer is composed principally of $\alpha$, $\beta$ and $\gamma$ subunits.

Presently a total number of 21 subunits of the GABA A receptor have been cloned and sequenced. Three types of subunits ($\alpha$, $\beta$ and $\gamma$) are required for the construction of recombinant GABA A receptors which most closely mimic the biochemical, electrophysiological and pharmacological functions of native GABA A receptors obtained from mammalian brain cells. There is strong evidence that the benzodiazepine binding site lies between the $\alpha$ and $\gamma$ subunits. Among the recombinant GABA A receptors, $\alpha 1\beta 2\gamma 2$ mimics many effects of the classical type-I BzR subtypes, whereas $\alpha 2\beta 2\gamma 2$, $\alpha 3\beta 2\gamma 2$ and $\alpha 5\beta 2\gamma 2$ ion channels are termed type-II BzR.

It has been shown by McNamara and Skelton in *Psychobiology*, 21:101-108 that the benzodiazepine receptor inverse agonist $\beta$-CCM enhance spatial learning in the Morris watermaze. However, $\beta$-CCM and other conventional benzodiazepine receptor inverse agonists are proconvulsant or convulsant which prevents their use as cognition enhancing agents in humans. In addition, these compounds are non-selective within the GABA A receptor subunits, whereas a GABA A $\alpha 5$ receptor partial or full inverse agonist which is relatively free of activity at GABA A $\alpha 1$ and/or $\alpha 2$ and/or $\alpha 3$ receptor binding sites can be used to provide a medicament which is useful for enhancing cognition with reduced or without proconvulsant activity. It is also possible to use GABA A $\alpha 5$ inverse agonists which are not free of activity at GABA A $\alpha 1$ and/or $\alpha 2$ and/or $\alpha 3$ receptor binding sites but which are functionally selective for $\alpha 5$ containing subunits. However, inverse agonists which are selective for GABA A $\alpha 5$ subunits and are relatively free of activity at GABA A $\alpha 1$, $\alpha 2$ and $\alpha 3$ receptor binding sites are preferred.

SUMMARY OF THE INVENTION

The present invention provides aryl-isoxazole-4-carbonyl-pyrrole-2-carboxylic acid amide derivatives of formula

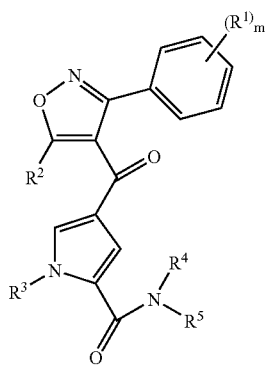

I wherein
$R^1$ is hydrogen, halogen, lower alkoxy, phenyloxy or benzyloxy;
$R^2$ is lower alkyl, $(CH_2)_n$—O-lower alkyl or phenyl;
$R^3$ is hydrogen or lower alkyl;
$R^4$ and $R^5$ are each independently
  hydrogen,
  lower alkyl,
  lower alkyl substituted by halogen,
  lower alkynyl,
  —$(CHR)_n$-aryl, unsubstituted or substituted by halogen, lower alkyl or lower alkoxy,
  —$(CH_2)_n$-non aromatic heterocyclic ring, unsubstituted or substituted by one or two lower alkyl groups,
  —$(CH_2)_n$-aromatic heterocyclic rings
  —$(CR_2)_n$-cycloalkyl, unsubstituted or substituted by one to three substituents selected from the group consisting of hydroxy or lower alkyl,
  —$(CHR)_n$—O-lower alkyl,
  —$(CR_2)_n$—OH, or
  —$(CHR)_n$—NR'R",
or $R^4$ and $R^5$ together with the N-atom to which they are attached form the ring
  8-aza-bicyclo[3.2.1] octane, substituted by hydroxy, or
  3,4-dihydro-1H-isoquinoline, or
  a non aromatic heterocyclic ring, unsubstituted or substituted by one or two substituents selected from the group consisting of C(O)O-lower alkyl, lower alkyl, lower alkyl substituted by halogen, cycloalkyl, hydroxy, halogen, N(R)C(O)-lower alkyl, —$(CH_2)_n$—O-lower alkyl, or by an aromatic heterocyclic ring;
R is hydrogen, hydroxy, or lower alkyl, wherein when there are two R groups, each R can be the same or different;
R' and R" are each independently hydrogen or lower alkyl;
n is 0, 1, 2, 3 or 4; and
m is 1, 2 or 3;
and with their pharmaceutically acceptable acid addition salts.

The present invention also provides pharmaceutical compositions which comprise a therapeutically effective amount of one or more compounds of the invention and a pharmaceutically acceptable carrier. The invention further provides methods for the preparation of the compounds and compositions of the invention.

This class of compounds have high affinity and selectivity for GABA A $\alpha 5$ receptor binding sites and might be useful as cognitive enhancer or for the treatment of cognitive disorders like Alzheimer's disease.

The most preferred indication in accordance with the present invention is Alzheimer's disease.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "lower alkyl" denotes a straight- or branched-chain hydrocarbon group containing from 1-7, preferably from 1-4, carbon atoms, for example, methyl, ethyl, propyl, isopropyl, n-butyl, i-butyl, t-butyl and the like.

The term "lower alkyl substituted by halogen" denotes a lower alkyl group as defined above, wherein at least one hydrogen atom is replaced by a halogen atom. Examples of preferred groups are CF$_3$, CHF$_2$, CH$_2$F, CH$_2$C(CH$_3$)F$_2$, CH$_2$CH$_2$F, CH$_2$CF$_2$H or CH$_2$CF$_3$ and CF$_2$CH$_3$.

The terms "lower alkoxy" and "O-lower alkyl" are used synonymously and denote a group wherein the alkyl residue is as defined above, which is attached via an oxygen atom.

The term "lower alkynyl" denotes a straight- or branched-chain hydrocarbon group containing from 2-7, preferably from 2-4, carbon atoms, wherein at least one bond is a triple bond.

The term "aryl" denotes an unsaturated carbon ring, for example a phenyl, benzyl or naphthyl group. A preferred aryl group is phenyl.

The term "halogen" denotes chlorine, iodine, fluorine and bromine.

The term "cycloalkyl" denotes a cyclic saturated hydrocarbon ring, having from 3 to 7 carbon ring atoms, for example, cyclopropyl, cyclopentyl or cyclohexyl.

The term "non aromatic heterocyclic ring" denotes a cyclic saturated carbon ring, having from one to three heteroatoms, selected from N, O, and S, for example the following rings: morpholin, thiomorpholin, piperazin, tetrahydropyran, piperidin, pyrrolidin and tetrahydrofuran.

The term "aromatic heterocyclic ring" denotes an aromatic 5 or 6 membered ring containing from one to three heteroatoms, selected from N, O and S atoms. Examples of such aromatic heterocyclic rings are pyridine, thiophen, imidazol, furan, oxazol and pyrazin.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

"Therapeutically effective amount" means an amount that is effective to prevent, alleviate or ameliorate symptoms of disease or prolong the survival of the subject being treated.

The present invention provides aryl-isoxazole-4-carbonyl-pyrrole-2-carboxylic acid amide derivatives of formula

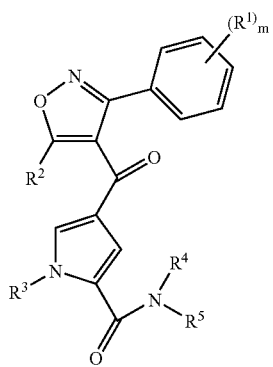

I wherein
$R^1$ is hydrogen, halogen, lower alkoxy, phenyloxy or benzyloxy;
$R^2$ is lower alkyl, (CH$_2$)$_n$—O-lower alkyl or phenyl;
$R^3$ is hydrogen or lower alkyl;
$R^4$ and $R^5$ are each independently hydrogen,
lower alkyl,
lower alkyl substituted by halogen,
lower alkynyl,
—(CHR)$_n$-aryl, unsubstituted or substituted by halogen, lower alkyl or lower alkoxy,
—(CH$_2$)$_n$-non aromatic heterocyclic ring, unsubstituted or substituted by one or two lower alkyl groups,
—(CH$_2$)$_n$-aromatic heterocyclic rings
—(CR$_2$)$_n$-cycloalkyl, unsubstituted or substituted by one to three substituents selected from the group consisting of hydroxy or lower alkyl,
—(CHR)$_n$—O-lower alkyl,
—(CR$_2$)$_n$—OH, or
—(CHR)$_n$—NR'R",
or $R^4$ and $R^5$ together with the N-atom to which they are attached form the ring
8-aza-bicyclo[3.2.1]octane, substituted by hydroxy, or
3,4-dihydro-1H-isoquinoline, or
a non aromatic heterocyclic ring, unsubstituted or substituted by one or two substituents selected from the group consisting of C(O)O-lower alkyl, lower alkyl, lower alkyl substituted by halogen, cycloalkyl, hydroxy, halogen, N(R)C(O)-lower alkyl, —(CH$_2$)$_n$—O-lower alkyl, or by an aromatic heterocyclic ring;
R is hydrogen, hydroxy, or lower alkyl, wherein when there are two R groups, each R can be the same or different;
R' and R" are each independently hydrogen or lower alkyl;
n is 0, 1, 2, 3 or 4; and
m is 1, 2 or 3;
and with their pharmaceutically acceptable acid addition salts.

Exemplary preferred compounds are those having binding activity (Ki) of lower than 0.01 µM that are selective for GABA A α5 subunits and are relatively free of activity at GABA A α1, α2 and α3 receptor binding sites.

Preferred compounds of formula I are those in which $R^1$ is hydrogen or halogen, $R^2$ is methyl, ethyl or CH$_2$OCH$_3$, $R^3$ is hydrogen or methyl and $R^4$ and $R^5$ do not form together with the N atom to which they are attached a heterocyclic ring.

More specifically, preferred compounds from this group are those wherein $R^1$ is hydrogen, $R^2$ is methyl or ethyl, $R^3$ and $R^4$ are hydrogen and $R^5$ is (CR$_2$)$_n$-cycloalkyl, unsubstituted or substituted by one to three substituents selected from the group consisting of hydroxy and lower alkyl, for example the following compounds:
4-(5-methyl-3-phenyl-isoxazole-4-carbonyl)-1H-pyrrole-2-carboxylic acid cyclopropylmethylamide,
4-(5-methyl-3-phenyl-isoxazole-4-carbonyl)-1H-pyrrole-2-carboxylic acid cyclobutylamide,
4-(5-ethyl-3-phenyl-isoxazole-4-carbonyl)-1H-pyrrole-2-carboxylic acid cyclopentylamide,
4-(5-ethyl-3-phenyl-isoxazole-4-carbonyl)-1H-pyrrole-2-carboxylic acid cyclopropylmethylamide and
4-(5-ethyl-3-phenyl-isoxazole-4-carbonyl)-1H-pyrrole-2-carboxylic acid cyclopropylamide.

Preferred compounds from this group are further those wherein $R^1$ is hydrogen, $R^2$ is methyl or ethyl, $R^3$ and $R^4$ are hydrogen and $R^5$ is (CH$_2$)$_n$-non aromatic heterocyclic ring, unsubstituted or substituted by one or two substituents selected from the group consisting of lower alkyl, for example the following compounds
4-(5-methyl-3-phenyl-isoxazole-4-carbonyl)-1H-pyrrole-2-carboxylic acid (tetrahydro-pyran-4-yl)-amide and
4-(5-ethyl-3-phenyl-isoxazole-4-carbonyl)-1H-pyrrole-2-carboxylic acid (tetrahydro-pyran-4-yl)-amide.

Preferred compounds from this group are further those wherein $R^1$ is Br, $R^2$ is methyl, $R^3$ is methyl, $R^4$ is hydrogen and $R^5$ is $(CH_2)_n$-non aromatic heterocyclic ring, unsubstituted or substituted by one or two substituents selected from the group consisting of lower alkyl, for example the following compounds 4-[3-(4-bromo-phenyl)-5-methyl-isoxazole-4-carbonyl]-1-methyl-1H-pyrrole-2-carboxylic acid (tetrahydro-pyran-4-yl)-amide and 4-[3-(4-bromo-phenyl)-5-methyl-isoxazole-4-carbonyl]-1-methyl-1H-pyrrole-2-carboxylic acid (3-morpholin-4-yl-propyl)-amide.

Preferred compounds are further those wherein $R^1$ is Br, Cl or F, $R^2$ is methyl or $CH_2OCH_3$, $R^3$ and $R^4$ are hydrogen and $R^5$ is $(CH_2)_n$-non aromatic heterocyclic ring, unsubstituted or substituted by one or two substituents selected from the group consisting of lower alkyl, for example the following compounds 4-[3-(4-bromo-phenyl)-5-methyl-isoxazole-4-carbonyl]-1H-pyrrole-2-carboxylic acid (tetrahydro-pyran-4-yl)-amide, 4-[3-(4-bromo-phenyl)-5-methyl-isoxazole-4-carbonyl]-1H-pyrrole-2-carboxylic acid (2,2-dimethyl-tetrahydro-pyran-4-yl)-amide, 4-[3-(4-fluoro-phenyl)-5-methyl-isoxazole-4-carbonyl]-1H-pyrrole-2-carboxylic acid (tetrahydro-pyran-4-yl)-amide, 4-[3-(4-chloro-phenyl)-5-methyl-isoxazole-4-carbonyl]-1H-pyrrole-2-carboxylic acid (tetrahydro-pyran-4-yl)-amide, 4-[3-(2-fluoro-phenyl)-5-methyl-isoxazole-4-carbonyl]-1H-pyrrole-2-carboxylic acid (tetrahydro-pyran-4-yl)-amide, 4-[3-(4-fluoro-phenyl)-5-methoxymethyl-isoxazole-4-carbonyl]-1H-pyrrole-2-carboxylic acid (tetrahydro-pyran-4-yl)-amide and 4-[3-(3,4-difluoro-phenyl)-5-methyl-isoxazole-4-carbonyl]-1H-pyrrole-2-carboxylic acid (tetrahydro-pyran-4-yl)-amide.

Preferred compounds are further those wherein $R^1$ is Br, Cl or F, $R^2$ is methyl, $R^3$ and $R^4$ are hydrogen and $R^5$ is lower alkyl or alkynyl, for example the following compounds 4-[3-(4-Bromo-phenyl)-5-methyl-isoxazole-4-carbonyl]-1H-pyrrole-2-carboxylic acid isopropylamide, 4-[3-(4-Fluoro-phenyl)-5-methyl-isoxazole-4-carbonyl]-1H-pyrrole-2-carboxylic acid prop-2-ynylamide and 4-[3-(4-Chloro-phenyl)-5-methyl-isoxazole-4-carbonyl]-1H-pyrrole-2-carboxylic acid prop-2-ynylamide.

Preferred compounds are further those wherein $R^1$ is Br, Cl or F, $R^2$ is methyl, $R^3$ and $R^4$ are hydrogen and $R^5$ is $(CR_2)_n$-cycloalkyl, unsubstituted or substituted by one to three substituents selected from the group consisting of hydroxy and lower alkyl, for example the following compounds 4-[3-(4-bromo-phenyl)-5-methyl-isoxazole-4-carbonyl]-1H-pyrrole-2-carboxylic acid (4-hydroxy-cyclohexyl)-amide, 4-[3-(4-fluoro-phenyl)-5-methyl-isoxazole-4-carbonyl]-1H-pyrrole-2-carboxylic acid cyclopentylamide, 4-[3-(4-fluoro-phenyl)-5-methyl-isoxazole-4-carbonyl]-1H-pyrrole-2-carboxylic acid cyclopropylamide, 4-[3-(4-fluoro-phenyl)-5-methyl-isoxazole-4-carbonyl]-1H-pyrrole-2-carboxylic acid cyclobutylamide, 4-[3-(4-chloro-phenyl)-5-methyl-isoxazole-4-carbonyl]-1H-pyrrole-2-carboxylic acid cyclopentylamide, 4-[3-(4-chloro-phenyl)-5-methyl-isoxazole-4-carbonyl]-1H-pyrrole-2-carboxylic acid cyclopropylamide, 4-[3-(4-chloro-phenyl)-5-methyl-isoxazole-4-carbonyl]-1H-pyrrole-2-carboxylic acid cyclopropylmethyl-amide, 4-[3-(2-fluoro-phenyl)-5-methyl-isoxazole-4-carbonyl]-1H-pyrrole-2-carboxylic acid cyclopentylamide, 4-[3-(3-fluoro-phenyl)-5-methyl-isoxazole-4-carbonyl]-1H-pyrrole-2-carboxylic acid cyclopentylamide and 4-[3-(3,4-difluoro-phenyl)-5-methyl-isoxazole-4-carbonyl]-1H-pyrrole-2-carboxylic acid cyclopentylamide.

Preferred compounds are further those wherein $R^1$ is Cl or F, $R^2$ is methyl, $R^3$ and $R^4$ are hydrogen and $R^5$ is $(CR_2)_n$—OH, for example the following compounds 4-[3-(4-fluoro-phenyl)-5-methyl-isoxazole-4-carbonyl]-1H-pyrrole-2-carboxylic acid (2-hydroxy-ethyl)-amide and 4-[3-(4-chloro-phenyl)-5-methyl-isoxazole-4-carbonyl]-1H-pyrrole-2-carboxylic acid (2-hydroxy-ethyl)-amide.

Preferred compounds are further those wherein $R^1$ is Cl or F, $R^2$ is methyl, $R^3$ and $R^4$ are hydrogen and $R^5$ is $(CH_2)_n$-aromatic heterocyclic ring, for example the following compounds 4-[3-(4-Fluoro-phenyl)-5-methyl-isoxazole-4-carbonyl]-1H-pyrrole-2-carboxylic acid [2-(1H-imidazol-4-yl)-ethyl]-amide, 4-[3-(4-Fluoro-phenyl)-5-methyl-isoxazole-4-carbonyl]-1H-pyrrole-2-carboxylic acid (furan-2-ylmethyl)-amide, 4-[3-(4-Chloro-phenyl)-5-methyl-isoxazole-4-carbonyl]-1H-pyrrole-2-carboxylic acid (furan-2-ylmethyl)-amide and 4-[3-(4-Chloro-phenyl)-5-methyl-isoxazole-4-carbonyl]-1H-pyrrole-2-carboxylic acid [2-(1H-imidazol-4-yl)-ethyl]-amide.

Preferred compounds of formula I are further those in which $R^1$ is hydrogen or halogen, $R^2$ is methyl, ethyl or $CH_2OCH_3$, $R^3$ is hydrogen or methyl and $R^4$ and $R^5$ form together with the N atom a heterocyclic ring.

The present compounds of formula I and their pharmaceutically acceptable salts can be prepared by methods known in the art, for example, by processes described below, which processes comprise a) reacting a compound of formula

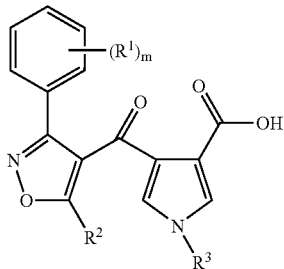

II with an amine of formula

III in the presence of TBTU and N,N-diisopropylethylamine to obtain a compound of formula

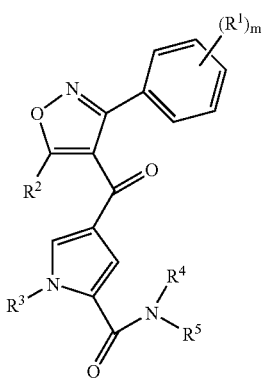

wherein $R^1$, $R^2$, $R^3$, $R^4$ and $R^5$ and m are as described above, or b) reacting a compound of formula

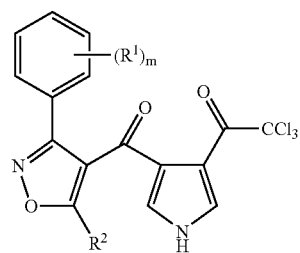

with an amine of formula

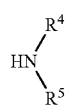

to obtain a compound of formula

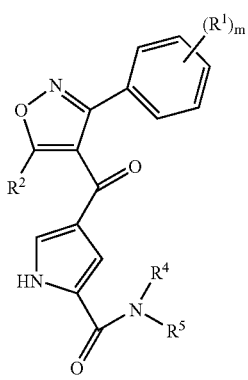

wherein $R^1$, $R^2$, $R^4$ and $R^5$ and m are as described above, c) reacting a compound of formula

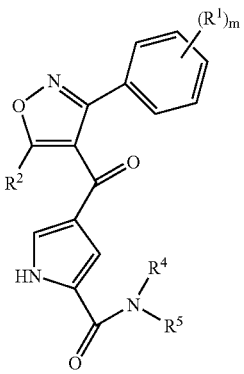

with an alkyliodide of formula $R^3I$ (for $R^3$=lower alkyl) to obtain a compound of formula

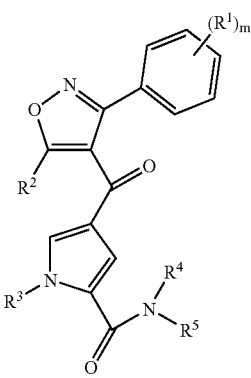

wherein $R^1$, $R^2$, $R^4$ and $R^5$ and m are as described above and $R^3$ is lower alkyl, and, if desired, converting a compound of formula I into a pharmaceutically acceptable salt.

The following schemes (scheme 1, 2 and 3) describe the processes for preparation of compounds of formula I in more detail. The starting materials of formulas III, IV, V, VII, VIII, IX and X are known compounds or can be prepared according to methods known in the art.

Scheme 1

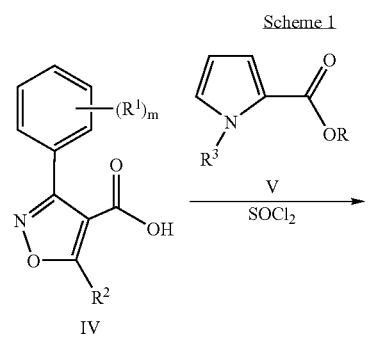

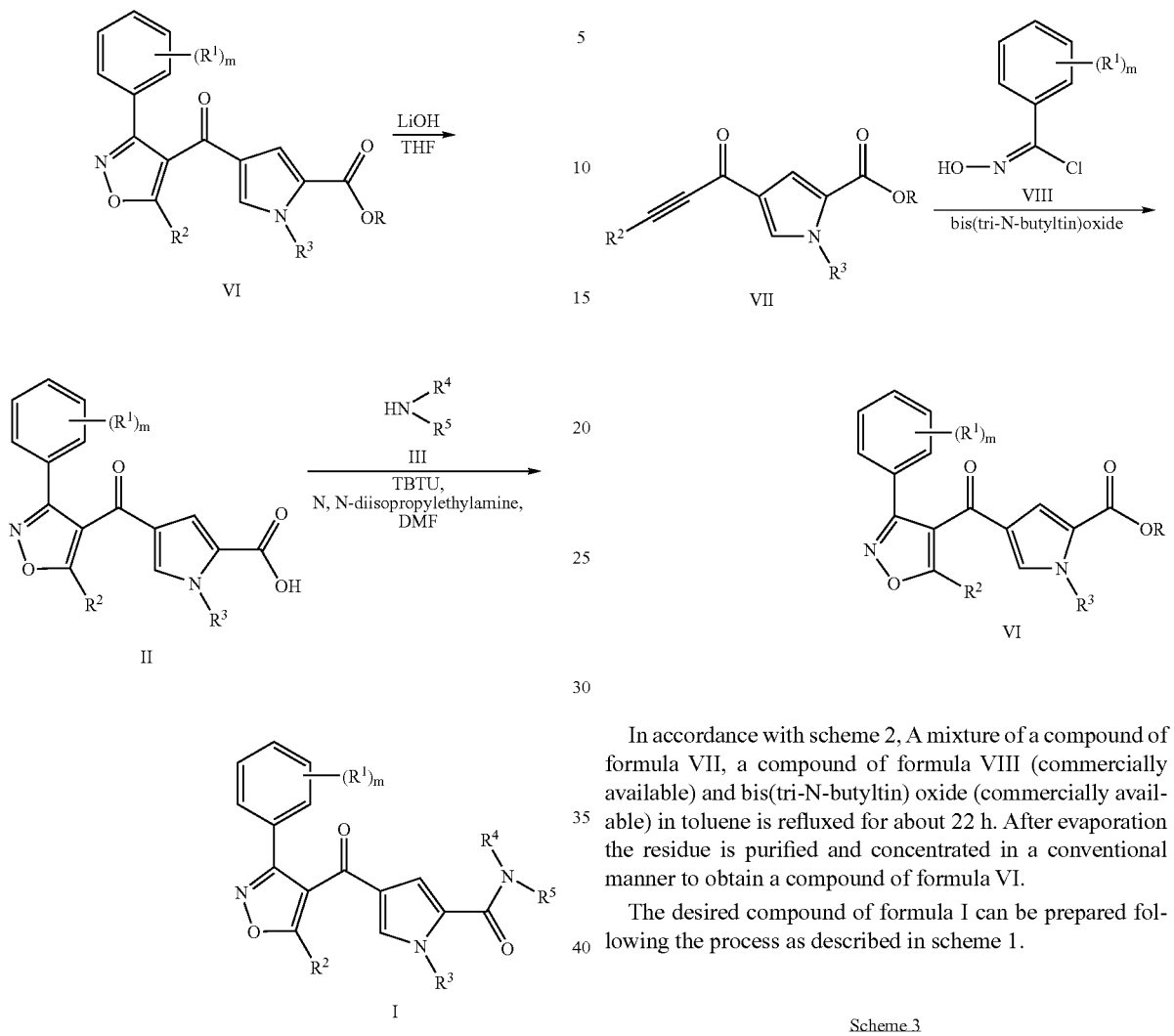

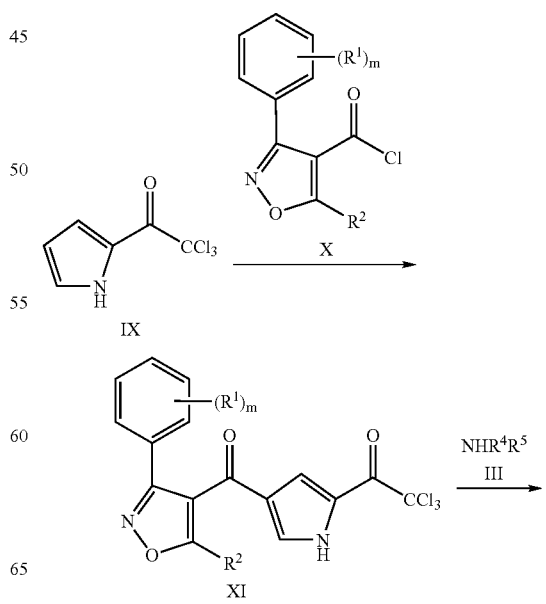

In accordance with scheme 2, A mixture of a compound of formula VII, a compound of formula VIII (commercially available) and bis(tri-N-butyltin) oxide (commercially available) in toluene is refluxed for about 22 h. After evaporation the residue is purified and concentrated in a conventional manner to obtain a compound of formula VI.

The desired compound of formula I can be prepared following the process as described in scheme 1.

In accordance with scheme 1, a compound of formula I can be prepared as follows:

A mixture of a compound of formula IV (commercially available) and $SOCl_2$ is heated to reflux for about 3 h. After evaporation the residue is added to a mixture of a compound of formula V (commercially available) and $AlCl_3$ in dichloroethane and heated to reflux for about 3 h. After cooling to room temperature and purification, a compound of formula VI is obtained.

A mixture of a compound of formula VI and $LiOH.H_2O$ in THF, methanol and water is heated to reflux for about 3 h. The mixture is concentrated and purified in a conventional manner to obtain a compound of formula II.

Further, a mixture of a compound of formula II, an amine of formula III (commercially available), 2-(1H-benzotriazole-1-yl)-1,1,3,3-tetramethyluronium tetrafluoroborate (TBTU), and N,N-disiopropylethylamine in DMF is reacted at room temperature for about 16 h to obtain the desired compound of formula I.

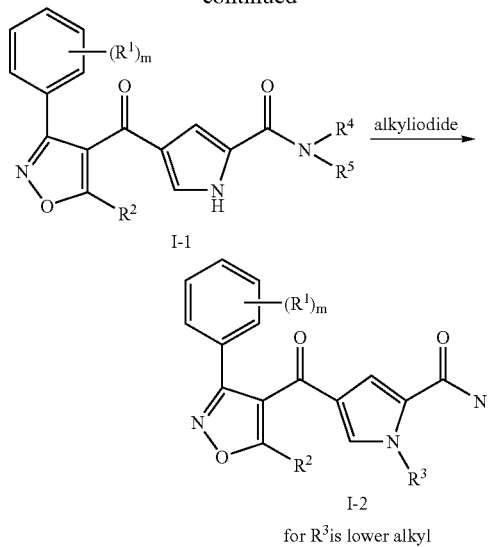

for R³ is lower alkyl

To a solution of 2-trichloroacetyl-1H-pyrrole (commercially available) in $CH_2Cl_2$ and nitromethane $AlCl_3$ is added in one portion. Then, a compound of formula X in $CH_2Cl_2$ is added dropwise. The reaction mixture is stirred at room temperature for about 18 h, concentrated and purified in conventional matter. Then, a mixture of the obtained compound of formula XI, an amine of formula III and triethylamine is stirred overnight at about 60° C. After cooling to room temperature, the reaction mixture is evaporated to dryness to obtain a compound of formula I-1. To a solution of this compound in dry DMF is added KOt-Bu, and the mixture is stirred at room temperature for about 30 minutes. The reaction is cooled to 0° C., and methyl iodide is added. The resulting mixture is stirred at room temperature for about 8 h. A compound of formula I, wherein $R^3$ is lower alkyl, is obtained.

As mentioned earlier, the compounds of formula I and their pharmaceutically usable salts possess valuable pharmacological properties. The compounds of the present invention are ligands for GABA A receptors containing the α5 subunit and are therefore useful in the therapy where cognition enhancement is required.

The compounds were investigated in accordance with the test given hereinafter.

Membrane Preparation and Binding Assay

The affinity of compounds at GABA A receptor subtypes was measured by competition for [3H]flumazenil (85 Ci/mmol; Roche) binding to HEK293 cells expressing rat (stably transfected) or human (transiently transfected) receptors of composition α1β3γ2, α2⊖3γ2, α3β3γ2 and α5β3γ2.

Cell pellets were suspended in Krebs-tris buffer (4.8 mM KCl, 1.2 mM CaCl2, 1.2 mM MgCl2, 120 mM NaCl, 15 mM Tris; pH 7.5; binding assay buffer), homogenized by polytron for ca. 20 sec on ice and centrifuged for 60 min at 4° C. (50000 g; Sorvall, rotor: SM24=20000 rpm). The cell pellets were resuspended in Krebs-tris buffer and homogenized by polytron for ca. 15 sec on ice. Protein was measured (Bradford method, Bio-Rad) and aliquots of 1 mL were prepared and stored at −80° C.

Radioligand binding assays were carried out in a volume of 200 mL (96-well plates) which contained 100 mL of cell membranes, [3H]flumazenil at a concentration of 1 nM for α1, α2, α3 subunits and 0.5 nM for α5 subunits and the test compound in the range of 10-10–3×10-6 M. Nonspecific binding was defined by 10-5 M diazepam and typically represented less than 5% of the total binding. Assays were incubated to equilibrium for 1 hour at 4° C. and harvested onto GF/C uni-filters (Packard) by filtration using a Packard harvester and washing with ice-cold wash buffer (50 mM Tris; pH 7.5). After drying, filter-retained radioactivity was detected by liquid scintillation counting. Ki values were calculated using Excel-Fit (Microsoft) and are the means of two determinations.

The compounds of the accompanying examples were tested in the above described assay, and were found to possess a Ki value for displacement of [3H]flumazenil from α5 subunits of the rat GABA A receptor of 100 nM or less. In a preferred embodiment the compounds of the invention are binding selective for the α5 subunit relative to the α1, α2 and α3 subunit.

| Example No. | Ki [µM] hα5 |
| --- | --- |
| 12 | 0.0066 |
| 15 | 0.00795 |
| 26 | 0.00285 |
| 61 | 0.00365 |
| 84 | 0.00685 |
| 123 | 0.0045 |
| 135 | 0.0045 |
| 136 | 0.00165 |
| 137 | 0.0041 |
| 138 | 0.0036 |
| 140 | 0.0099 |
| 141 | 0.00605 |
| 144 | 0.0061 |
| 145 | 0.00775 |
| 146 | 0.00155 |
| 152 | 0.0052 |
| 153 | 0.00755 |
| 154 | 0.0061 |
| 156 | 0.00385 |
| 157 | 0.00745 |
| 160 | 0.0069 |
| 161 | 0.0063 |
| 162 | 0.0014 |
| 163 | 0.0061 |
| 173 | 0.0063 |
| 178 | 0.0061 |
| 210 | 0.00245 |
| 215 | 0.0021 |
| 216 | 0.0023 |
| 217 | 0.00485 |
| 221 | 0.0043 |
| 231 | 0.008 |
| 232 | 0.0087 |
| 254 | 0.0042 |
| 255 | 0.0064 |

The present invention also provides pharmaceutical compositions containing compounds of formula I or pharmaceutically acceptable acid addition salts thereof and a pharmaceutically acceptable carrier. The pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of formula I or their pharmaceutically acceptable acid addition salts, contain a pharmaceutically acceptable carrier. Suitable pharmaceutically acceptable carriers include pharmaceutically inert, inorganic or organic carriers. Lactose, corn starch or derivatives thereof, talc, stearic acid or its salts etc can be used as such excipients e.g. for tablets, dragées and hard gelatin capsules. Suitable excipients for soft gelatin capsules are e.g. vegetable oils, waxes, fats, semisolid and liquid polyols etc. Suitable excipients for the manufacture of solutions and syrups are e.g. water, polyols, saccharose, invert sugar, glucose etc. Suitable excipients for injection solutions are e.g. water, alcohols, polyols, glycerol, vegetable oils etc. Suitable excipients for suppositories are e.g. natural or hardened oils, waxes, fats, semi-liquid or liquid polyols etc.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carrier.

This class of compounds has high affinity and selectivity for GABA A α5 receptor binding sites and are useful as cognitive enhancers or for the treatment of cognitive disorders like Alzheimer's disease. Thus, the present invention also provides a method for the treatment of Alzheimer's disease which comprises administering a therapeutically effective amount of a compound of the invention.

The compounds and compositions of the present invention can be administered in a conventional manner, for example, orally, rectally, or parenterally. The pharmaceutical compositions of the invention can be administered orally, for example, in the form of tablets, coated tablets, dragées, hard and soft gelatin capsules, solutions, emulsions, or suspensions. The pharmaceutical compositions also can be administered rectally, for example, in the form of suppositories, or parenterally, for example, in the form of injectable solutions.

The dosage at which a compound of the invention is administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following examples illustrate the present invention without limiting it. All temperatures are given in degrees Celsius.

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The following examples are provided for illustration of the invention. They should not be considered as limiting the scope of the invention, but merely as being representative thereof. Examples 2, 229 and 230 have been described in detail, the remaining compounds have been prepared accordingly.

EXAMPLE 2

4-(5-Methyl-3-phenyl-isoxazole-4-carbonyl)-1H-pyrrole-2-carboxylic acid (pyridin-2-ylmethyl)-amide

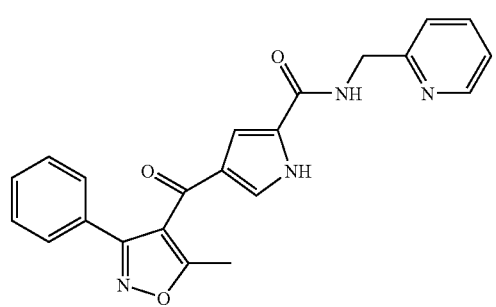

a) Step 1:

4-(5-Methyl-3-phenyl-isoxazole-4-carbonyl)-1H-pyrrole-2-carboxylic acid methyl ester

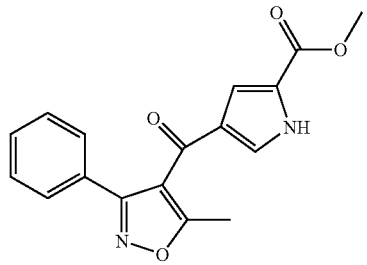

A mixture of 406 mg (2 mmol) 5-methyl-3-phenyl-isoxazole-4-carboxylic acid (commercially available) and 4 mL $SOCl_2$ was heated to reflux for 3 h. After evaporation of all volatiles the residue was added to a mixture of 206 mg (2 mmol) 1H-pyrrole-2-carboxylic acid methyl ester (commercially available) and 440 mg (3 mmol) $AMCl_3$ in 25 mL dichloroethane and heated to reflux for 3 h. After cooling to room temperature the precipitate was collected and washed with dichloromethane. The residue was purified on silica eluting with a gradient of ethyl acetate and heptane affording 210 mg (37%) of the title compound as white foam. (m/e): 311.0 ($MH^+$; 100%).

b) Step 2:

4-(5-Methyl-3-phenyl-isoxazole-4-carbonyl)-1H-pyrrole-2-carboxylic acid (intermediate 1)

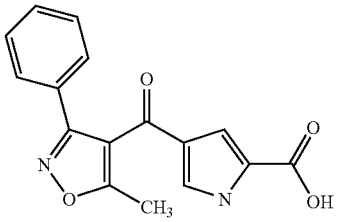

A mixture of 1.2 g (4 mmol) 4-(5-methyl-3-phenyl-isoxazole-4-carbonyl)-1H-pyrrole-2-carboxylic acid methyl ester and 1.3 g (31 mmol) $LiOH.H_2O$ in 40 mL THF, 5 mL methanol and 10 mL water was heated to reflux for 3 h. The mixture was concentrated, acidified and extracted with ethyl acetate. The combined organic extracts were dried with $Na_2SO_4$ and evaporated to yield 1.1 g (96%) of the title compound as light yellow solid. (m/e): 295.1 ($M^-$; 100%).

c) Step 3:

A mixture of 20 mg (0.67 mmol) 4-(5-methyl-3-phenyl-isoxazole-4-carbonyl)-1H-pyrrole-2-carboxylic acid (intermediate 1), 11 mg (0.1 mmol) C-pyridin-2-yl-methylamine (commercially available), 32 mg (0.1 mmol) 2-(1H-benzotriazole-1-yl)-1,1,3,3-tetramethyluronium tetrafluoroborate (TBTU) and 26 mg (0.2 mmol) N,N-disiopropylethylamine in 1.1 mL DMF was reacted at room temperature for 16 h and subsequently subjected to preparative HPLC purification on reversed phase eluting with a acetonitrile/water (0.05% $NEt_3$) gradient. After evaporation of the product fractions 7.6 mg (29%) of the title compound was obtained. (m/e): 387.2 ($MH^+$; 100%)

Intermediate 2

4-[3-(4-Bromo-phenyl)-5-methyl-isoxazole-4-carbonyl]-1H-pyrrole-2-carboxylic acid

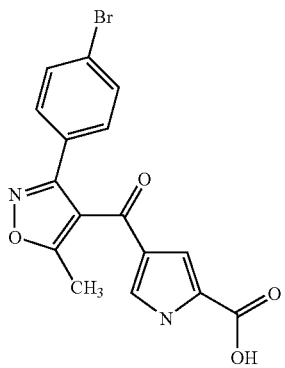

a) Step 1:

4-(1-Oxo-but-2-ynyl)-1H-pyrrole-2-carboxylic acid methyl ester

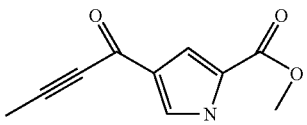

A mixture of 1 g (10 mmol) but-2-ynoyl chloride (Journal of Organic Chemistry (1981), 46(11), 2273-80), 0.625 g (5 mmol) 5-Methyl-3-phenyl-isoxazole-4-carboxylic acid (commercially available) and 1.3 g (10 mmol) $AlCl_3$ in 10 mL dichloroethane was at room temperature for 18 h. The mixture was poured onto ice/water and the organic layer washed with $Na_2CO_3$ sat., NaCl sat. and dried with $Na_2SO_4$. After evaporation of all volatiles the residue was purified on silica eluting with a gradient of ethyl acetate and heptane affording 0.2 g (17%) of the title compound as light brown solid. (m/e): 227.1 ($M^+$).

b) Step 2:

4-[3-(4-Bromo-phenyl)-5-methyl-isoxazole-4-carbonyl]-1H-pyrrole-2-carboxylic acid methyl ester

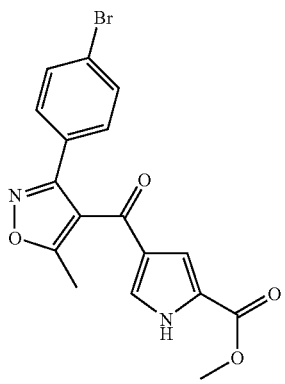

A mixture of 956 mg (5 mmol) 4-(1-oxo-but-2-ynyl)-1H-pyrrole-2-carboxylic acid methyl ester, 3.5 g (15 mmol) 4-bromo-N-hydroxybenzenecarboxymidoyl chloride (commercially available) and 4.47 g (7 mmol) bis(tri-N-butyltin) oxide (commercially available) in 75 mL toluene was refluxed for 22 h. After evaporation of all volatiles the residue was purified on silica eluting with a gradient of ethyl acetate and heptane affording 990 mg (51%) of the title compound as light yellow solid. (m/e): 389.3 (M+; 100%).

c) Step 3:

According to the procedure described for the synthesis of 4-(5-methyl-3-phenyl-isoxazole-4-carbonyl)-1H-pyrrole-2-carboxylic acid (intermediate 1), 4-[3-(4-bromo-phenyl)-5-methyl-isoxazole-4-carbonyl]-1H-pyrrole-2-carboxylic acid (intermediate 2) was synthesized from 4-[3-(4-bromo-phenyl)-5-methyl-isoxazole-4-carbonyl]-1H-pyrrole-2-carboxylic acid methyl ester through saponification with LiOH.H$_2$O. The title compound was obtained in 93% yield as white solid. (m/e): 374.8 (M−; 97%).

Intermediate 3

4-[3-(4-Fluoro-phenyl)-5-methyl-isoxazole-4-carbonyl]-1H-pyrrole-2-carboxylic acid

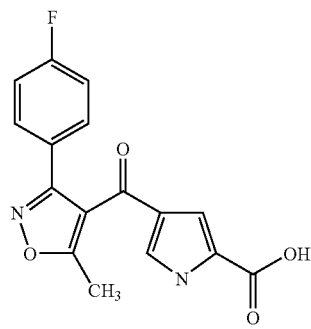

a) Step 1:

4-[3-(4-Fluoro-phenyl)-5-methyl-isoxazole-4-carbonyl]-1H-pyrrole-2-carboxylic acid methyl ester

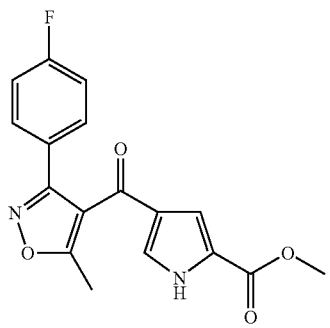

According to the procedure described for the synthesis of 4-[3-(4-bromo-phenyl)-5-methyl-isoxazole-4-carbonyl]-1H-pyrrole-2-carboxylic acid methyl ester (intermediate 2, step 2), 4-[3-(4-fluoro-phenyl)-5-methyl-isoxazole-4-carbonyl]-1H-pyrrole-2-carboxylic acid methyl ester was obtained from 4-(1-oxo-but-2-ynyl)-1H-pyrrole-2-carboxylic acid methyl ester and 4-fluoro-N-hydroxybenzenecarboxymidoyl chloride (commercially available) in 53.6% yield as light brown solid. (m/e): 329.0 (M+; 100%).

b) Step 2:

According to the procedure described for the synthesis of 4-(5-methyl-3-phenyl-isoxazole-4-carbonyl)-1H-pyrrole-2-carboxylic acid (intermediate 1), 4-[3-(4-fluoro-phenyl)-5-methyl-isoxazole-4-carbonyl]-1H-pyrrole-2-carboxylic acid (intermediate 3) was synthesized from 4-[3-(4-fluoro-phenyl)-5-methyl-isoxazole-4-carbonyl]-1H-pyrrole-2-carboxylic acid methyl ester through saponification with LiOH.H$_2$O. The title compound was obtained in 95% yield as white solid. (m/e): 315.2 (M+; 100%).

Intermediate 4

4-[3-(4-Methoxy-phenyl)-5-methyl-isoxazole-4-carbonyl]-1H-pyrrole-2-carboxylic acid

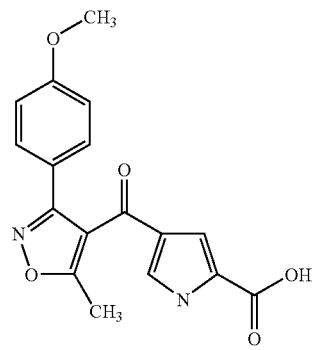

a) Step 1:

4-[3-(4-Methoxy-phenyl)-5-methyl-isoxazole-4-carbonyl]-1H-pyrrole-2-carboxylic acid methyl ester

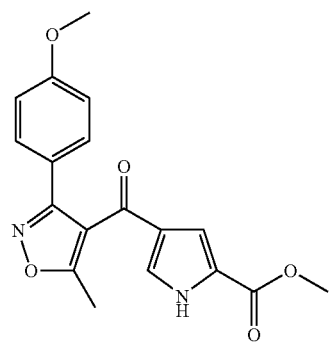

According to the procedure described for the synthesis of 4-[3-(4-bromo-phenyl)-5-methyl-isoxazole-4-carbonyl]-1H-pyrrole-2-carboxylic acid methyl ester (intermediate 2, step 2), 4-[3-(4-methoxy-phenyl)-5-methyl-isoxazole-4-carbonyl]-1H-pyrrole-2-carboxylic acid methyl ester was obtained from 4-(1-oxo-but-2-ynyl)-1H-pyrrole-2-carboxylic acid methyl ester and 4-methoxy-N-hydroxybenzenecarboxymidoyl chloride (commercially available) in 58% yield as light brown solid (m/e): 341.3 (M+; 100%).

b) Step 2:

According to the procedure described for the synthesis of 4-(5-methyl-3-phenyl-isoxazole-4-carbonyl)-1H-pyrrole-2-carboxylic acid (intermediate 1), 4-[3-(4-Methoxy-phenyl)-5-methyl-isoxazole-4-carbonyl]-1H-pyrrole-2-carboxylic acid (intermediate 4) was synthesized from 4-[3-(4-methoxy-phenyl)-5-methyl-isoxazole-4-carbonyl]-1H-pyrrole-2-carboxylic acid methyl ester through saponification with LiOH.H$_2$O. The title compound was obtained in 85% yield as white solid. (m/e): 325.1 (M$^-$; 100%).

Intermediate 5

4-[3-(4-Chloro-phenyl)-5-methyl-isoxazole-4-carbonyl]-1H-pyrrole-2-carboxylic acid

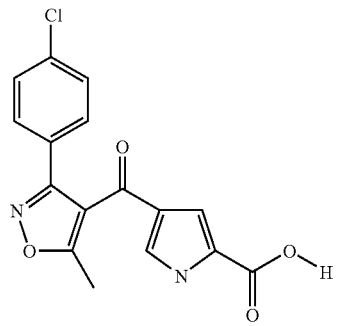

a) Step 1:

4-[3-(4-Chloro-phenyl)-5-methyl-isoxazole-4-carbonyl]-1H-pyrrole-2-carboxylic acid methyl ester

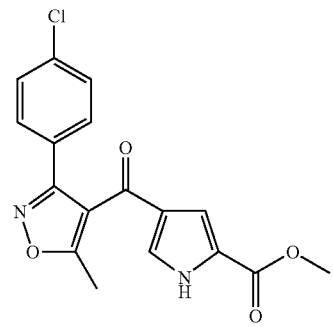

According to the procedure described for the synthesis of 4-[3-(4-bromo-phenyl)-5-methyl-isoxazole-4-carbonyl]-1H-pyrrole-2-carboxylic acid methyl ester (intermediate 2, step 2), 4-[3-(4-chloro-phenyl)-5-methyl-isoxazole-4-carbonyl]-1H-pyrrole-2-carboxylic acid methyl ester was obtained from 4-(1-oxo-but-2-ynyl)-1H-pyrrole-2-carboxylic acid methyl ester and 4-chloro-N-hydroxybenzenecarboxymidoyl chloride (commercially available) in 42% yield as light yellow solid. (m/e): 345.1 (M$^+$; 100%).

b) Step 2:

According to the procedure described for the synthesis of 4-(5-methyl-3-phenyl-isoxazole-4-carbonyl)-1H-pyrrole-2-carboxylic acid (intermediate 1), 4-[3-(4-chloro-phenyl)-5-methyl-isoxazole-4-carbonyl]-1H-pyrrole-2-carboxylic acid (intermediate 5) was synthesized from 4-[3-(4-chloro-phenyl)-5-methyl-isoxazole-4-carbonyl]-1H-pyrrole-2-carboxylic acid methyl ester through saponification with LiOH.H$_2$O. The title compound was obtained in 91% yield as light-yellow solid. (m/e): 331.1 (M$^+$; 100%).

Intermediate 6

4-[3-(2-Fluoro-phenyl)-5-methyl-isoxazole-4-carbonyl]-1H-pyrrole-2-carboxylic acid

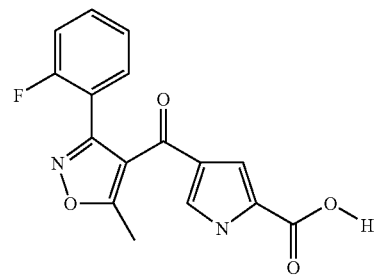

a) Step 1:

4-[3-(2-Fluoro-phenyl)-5-methyl-isoxazole-4-carbonyl]-1H-pyrrole-2-carboxylic acid methyl ester

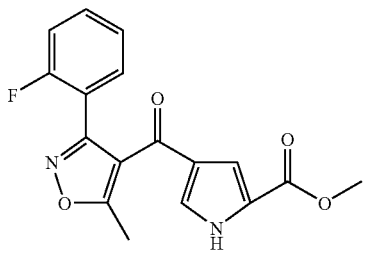

A mixture of 4.07 g (21.3 mmol) 4-(1-oxo-but-2-ynyl)-1H-pyrrole-2-carboxylic acid methyl ester, 18.5 g (106.5 mmol) 2-fluoro-N-hydroxybenzenecarboxymidoyl chloride (commercially available) and 12.7 g (21.3 mmol) Bis(tri-N-butyl-tin) oxide (commercially available) in 300 mL toluene was refluxed for 22 h. After evaporation of all volatiles the residue was purified on silica eluting with a gradient of ethyl acetate and hexane affording 6.78 g (97%) of the title compound as light brown solid. (m/e): 329.0 (M$^+$; 100%).

b) Step 2:

According to the procedure described for the synthesis of 4-(5-methyl-3-phenyl-isoxazole-4-carbonyl)-1H-pyrrole-2-carboxylic acid (intermediate 1), 4-[3-(2-fluoro-phenyl)-5-methyl-isoxazole-4-carbonyl]-1H-pyrrole-2-carboxylic acid (intermediate 6) was synthesized from 4-[3-(2-fluoro-phenyl)-5-methyl-isoxazole-4-carbonyl]-1H-pyrrole-2-carboxylic acid methyl ester through saponification with LiOH.H$_2$O. The title compound was obtained in 93% yield as white solid. (m/e): 313.3 (M$^-$; 100%).

Intermediate 7

4-[3-(3-Fluoro-phenyl)-5-methyl-isoxazole-4-carbonyl]-1H-pyrrole-2-carboxylic acid

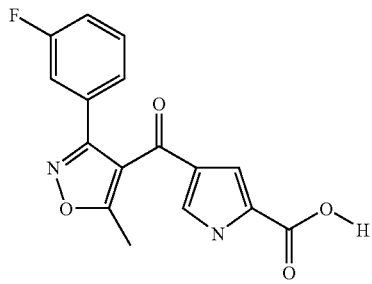

a) Step 1:

4-[3-(3-Fluoro-phenyl)-5-methyl-isoxazole-4-carbonyl]-1H-pyrrole-2-carboxylic acid methyl ester

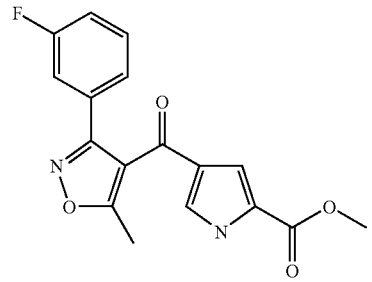

According to the procedure described for the synthesis of 4-[3-(2-fluoro-phenyl)-5-methyl-isoxazole-4-carbonyl]-1H-pyrrole-2-carboxylic acid methyl ester (intermediate 6, step 1), 4-[3-(3-fluoro-phenyl)-5-methyl-isoxazole-4-carbonyl]-1H-pyrrole-2-carboxylic acid methyl ester was obtained from 4-(1-oxo-but-2-ynyl)-1H-pyrrole-2-carboxylic acid methyl ester and 3-fluoro-N-hydroxybenzenecarboxymidoyl chloride (Bioorganic & Medicinal Chemistry Letters (2003), 13(10), 1795-1799) in 94% yield as light brown solid (m/e): 329.0 (M+; 100%).

b) Step 2:

According to the procedure described for the synthesis of 4-(5-methyl-3-phenyl-isoxazole-4-carbonyl)-1H-pyrrole-2-carboxylic acid (intermediate 1), 4-[3-(3-fluoro-phenyl)-5-methyl-isoxazole-4-carbonyl]-1H-pyrrole-2-carboxylic acid (intermediate 7) was synthesized from 4-[3-(3-fluoro-phenyl)-5-methyl-isoxazole-4-carbonyl]-1H-pyrrole-2-carboxylic acid methyl ester through saponification with LiOH.H2O. The title compound was obtained in 90% yield as white solid. (m/e): 313.3 (M−; 100%).

Intermediate 8

4-[3-(3-Chloro-phenyl)-5-methyl-isoxazole-4-carbonyl]-1H-pyrrole-2-carboxylic acid

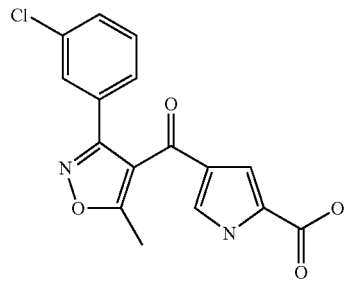

a) Step 1:

4-[3-(3-Chloro-phenyl)-5-methyl-isoxazole-4-carbonyl]-1H-pyrrole-2-carboxylic acid methyl ester

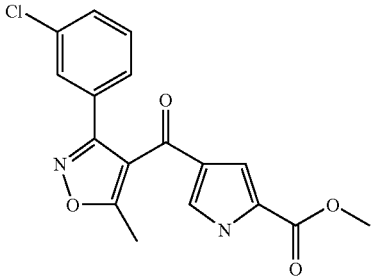

According to the procedure described for the synthesis of 4-[3-(4-bromo-phenyl)-5-methyl-isoxazole-4-carbonyl]-1H-pyrrole-2-carboxylic acid methyl ester (intermediate 2, step 2), 4-[3-(3-chloro-phenyl)-5-methyl-isoxazole-4-carbonyl]-1H-pyrrole-2-carboxylic acid methyl ester was obtained from 4-(1-oxo-but-2-ynyl)-1H-pyrrole-2-carboxylic acid methyl ester and 3-chloro-N-hydroxybenzenecarboxymidoyl chloride (Bioorganic & Medicinal Chemistry Letters (2003), 13(10), 1795-1799) in 52% yield as light yellow solid. (m/e): 345.0 (M+; 100%).

b) Step 2:

According to the procedure described for the synthesis of 4-(5-methyl-3-phenyl-isoxazole-4-carbonyl)-1H-pyrrole-2-carboxylic acid (intermediate 1, step 2), 4-[3-(3-chloro-phenyl)-5-methyl-isoxazole-4-carbonyl]-1H-pyrrole-2-carboxylic acid (intermediate 8) was synthesized from 4-[3-(3-chloro-phenyl)-5-methyl-isoxazole-4-carbonyl]-1H-pyrrole-2-carboxylic acid methyl ester through saponification with LiOH.H2O. The title compound was obtained in 95% yield as light-yellow solid.

Intermediate 9

4-[3-(3-Bromo-phenyl)-5-methyl-isoxazole-4-carbonyl]-1H-pyrrole-2-carboxylic acid

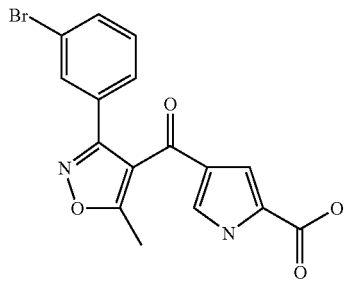

a) Step 1:

4-[3-(3-Bromo-phenyl)-5-methyl-isoxazole-4-carbonyl]-1H-pyrrole-2-carboxylic acid methyl ester

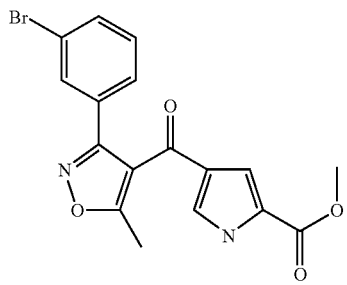

According to the procedure described for the synthesis of 4-[3-(4-bromo-phenyl)-5-methyl-isoxazole-4-carbonyl]-1H-pyrrole-2-carboxylic acid methyl ester (intermediate 2, step 2), 4-[3-(3-bromo-phenyl)-5-methyl-isoxazole-4-carbonyl]-1H-pyrrole-2-carboxylic acid methyl ester was obtained from 4-(1-oxo-but-2-ynyl)-1H-pyrrole-2-carboxylic acid methyl ester and 3-bromo-N-hydroxybenzenecarboxymidoyl chloride (commercially available) in 40% yield as light brown solid (m/e): 389.1 ($M^+$; 100%).

b) Step 2:

According to the procedure described for the synthesis of 4-(5-methyl-3-phenyl-isoxazole-4-carbonyl)-1H-pyrrole-2-carboxylic acid (intermediate 1, step 2), 4-[3-(3-bromo-phenyl)-5-methyl-isoxazole-4-carbonyl]-1H-pyrrole-2-carboxylic acid (intermediate 9) was synthesized from 4-[3-(3-bromo-phenyl)-5-methyl-isoxazole-4-carbonyl]-1H-pyrrole-2-carboxylic acid methyl ester through saponification with $LiOH.H_2O$. The title compound was obtained in 93% yield as light-yellow solid.

Intermediate 10

4-[5-Methyl-3-(4-phenoxy-phenyl)-isoxazole-4-carbonyl]-1H-pyrrole-2-carboxylic acid

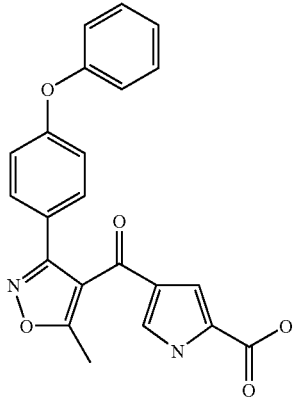

a) Step 1:

4-[5-Methyl-3-(4-phenoxy-phenyl)-isoxazole-4-carbonyl]-1H-pyrrole-2-carboxylic acid methyl ester

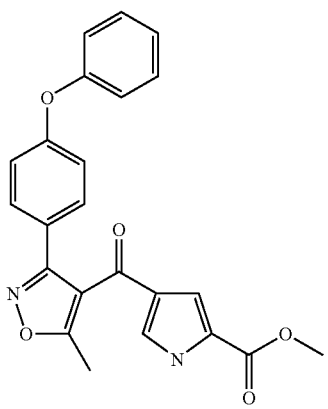

According to the procedure described for the synthesis of 4-[3-(4-bromo-phenyl)-5-methyl-isoxazole-4-carbonyl]-1H-pyrrole-2-carboxylic acid methyl ester (intermediate 2, step 2), 4-[3-(4-phenoxy-phenyl)-5-methyl-isoxazole-4-carbonyl]-1H-pyrrole-2-carboxylic acid methyl ester was obtained from 4-(1-oxo-but-2-ynyl)-1H-pyrrole-2-carboxylic acid methyl ester and 4-phenoxy-N-hydroxybenzenecarboxymidoyl chloride (Journal of Fluorine Chemistry, 111(2), 241-246; 2001) in 88% yield as yellow solid (m/e): 403.0 ($M^+$; 100%).

b) Step 2:

According to the procedure described for the synthesis of 4-(5-methyl-3-phenyl-isoxazole-4-carbonyl)-1H-pyrrole-2-carboxylic acid (intermediate 1, step 2), 4-[3-(4-phenoxy-phenyl)-5-methyl-isoxazole-4-carbonyl]-1H-pyrrole-2-carboxylic acid (intermediate 10) was synthesized from 4-[3-(4-phenoxy-phenyl)-5-methyl-isoxazole-4-carbonyl]-1H-pyrrole-2-carboxylic acid methyl ester through saponification with $LiOH.H_2O$. The title compound was obtained in 86% yield as light-yellow solid.

Intermediate 11

4-[3-(4-Benzyloxy-phenyl)-5-methyl-isoxazole-4-carbonyl]-1H-pyrrole-2-carboxylic acid

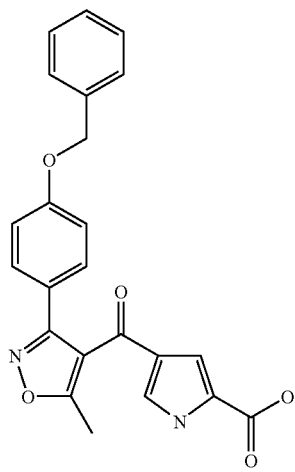

a) Step 1:

4-[3-(4-Benzyloxy-phenyl)-5-methyl-isoxazole-4-carbonyl]-1H-pyrrole-2-carboxylic acid methyl ester

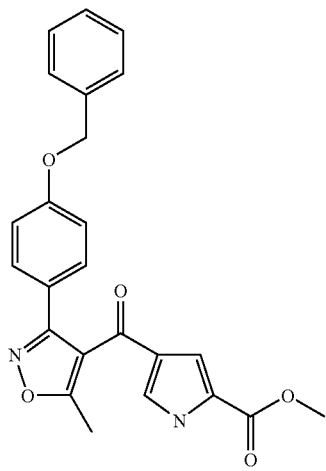

According to the procedure described for the synthesis of 4-[3-(4-bromo-phenyl)-5-methyl-isoxazole-4-carbonyl]-1H-pyrrole-2-carboxylic acid methyl ester (intermediate 2, step 2), 4-[3-(4-benzyloxy-phenyl)-5-methyl-isoxazole-4-carbonyl]-1H-pyrrole-2-carboxylic acid methyl ester was obtained from 4-(1-oxo-but-2-ynyl)-1H-pyrrole-2-carboxylic acid methyl ester and 4-benzyloxy-N-hydroxybenzenecarboxymidoyl chloride (Journal of Fluorine Chemistry, 111(2), 241-246; 2001) in 90% yield as light yellow solid (m/e): 417.1 (M+; 100%).

b) Step 2:

According to the procedure described for the synthesis of 4-(5-methyl-3-phenyl-isoxazole-4-carbonyl)-1H-pyrrole-2-carboxylic acid (intermediate 1, step 2), 4-[3-(4-benzyloxy-phenyl)-5-methyl-isoxazole-4-carbonyl]-1H-pyrrole-2-carboxylic acid (intermediate 11) was synthesized from 4-[3-(4-benzyloxy-phenyl)-5-methyl-isoxazole-4-carbonyl]-1H-pyrrole-2-carboxylic acid methyl ester through saponification with LiOH.H$_2$O. The title compound was obtained in 80% yield as light-yellow solid.

Intermediate 12

4-(5-Ethyl-3-phenyl-isoxazole-4-carbonyl)-1H-pyrrole-2-carboxylic acid

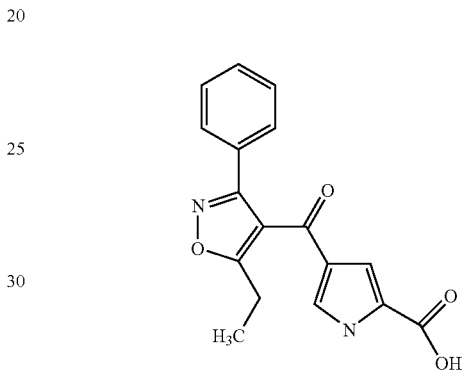

a) Step 1:

5-Ethyl-3-phenyl-isoxazole-4-carboxylic acid

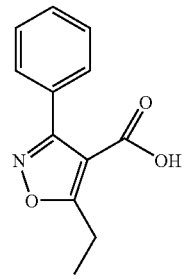

8.0 g (34 mmol) of 5-Ethyl-3-phenyl-isoxazole-4-carboxylic acid methyl ester (prepared according to: Synthesis 2003; 1347-1356) was dissolved in 50 mL of THF, to which 7.2 g (170 mmol) LiOH.H$_2$O in 25 ml of H$_2$O was added in one portion. The reaction mixture was refluxed for 12 h. After evaporation of THF, the aqueous solution was acidified with 2N HCl to pH=2. After extraction with ethyl acetate (3×100 mL), the combined organic extracts were dried over Na$_2$SO$_4$ and evaporated to dryness to give 5-Ethyl-3-phenyl-isoxazole-4-carboxylic acid (6.32 g) in 72.3% yield as a red solid. (m/e): 216.2 (M−; 100%).

b) Step 2:

4-(Ethyl-3-phenyl-isoxazole-4-carbonyl)-1H-pyrrole-2-carboxylic acid methyl ester

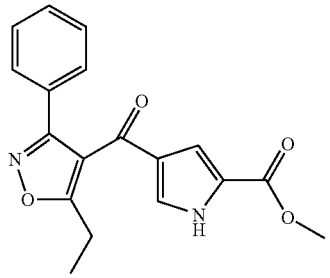

According to the procedure described for the synthesis of 4-(5-methyl-3-phenyl-isoxazole-4-carbonyl)-1H-pyrrole-2-carboxylic acid methyl ester (Example 1, step 1), 4-(ethyl-3-phenyl-isoxazole-4-carbonyl)-1H-pyrrole-2-carboxylic acid methyl ester was obtained as light yellow solid in 55% yield. (m/e): 325.2 (M$^+$; 100%).

c) Step 3:

According to the procedure described for the synthesis of 4-(5-methyl-3-phenyl-isoxazole-4-carbonyl)-1H-pyrrole-2-carboxylic acid (intermediate 1, step 2), 4-[5-ethyl-3-phenyl-isoxazole-4-carbonyl]-1H-pyrrole-2-carboxylic acid (intermediate 12) was synthesized from 4-(5-methyl-3-phenyl-isoxazole-4-carbonyl)-1H-pyrrole-2-carboxylic acid methyl ester through saponification with LiOH.H$_2$O. The title compound was obtained in 75.6% yield as red solid. (m/e):309.3 (M$^-$; 100%).

Intermediate 13

4-[3-(4-Fluoro-phenyl)-5-methoxymethyl-isoxazole-4-carbonyl]-1H-pyrrole-2-carboxylic acid

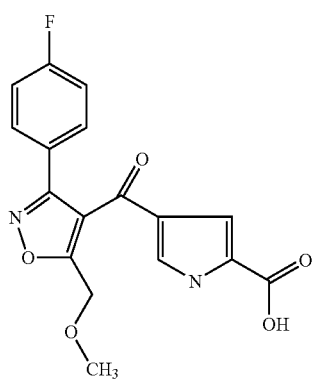

a) Step 1:

5-Methoxymethyl-3-(4-Fluoro-phenyl)-isoxazole-4-carboxylic acid

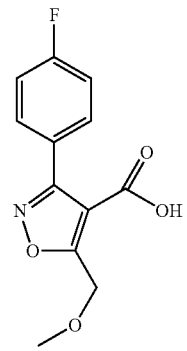

According to the procedure described for the synthesis of 5-ethyl-3-phenyl-isoxazole-4-carboxylic acid (intermediate 12, step 1), 5-methoxymethyl-3-(4-Fluoro-phenyl)-isoxazole-4-carboxylic acid was synthesised from 5-methoxymethyl-3-(4-Fluoro-phenyl)-isoxazole-4-carboxylic acid methyl ester (prepared according to: Synthesis 2003; 1347-1356) in 72% yield as light yellow solid. (m/e): 250.2 (M$^-$; 100%).

b) Step 2:

According to the procedure described for the synthesis of 4-(5-methyl-3-phenyl-isoxazole-4-carbonyl)-1H-pyrrole-2-carboxylic acid methyl ester (Example 1, step 1), 4-[3-(4-fluoro-phenyl)-5-methoxymethyl-isoxazole-4-carbonyl]-1H-pyrrole-2-carboxylic acid methyl ester was obtained in 16% yield as light yellow solid. (m/e): 359.1 (M$^+$; 100%).

c) Step 3:

According to the procedure described for the synthesis of 4-(5-methyl-3-phenyl-isoxazole-4-carbonyl)-1H-pyrrole-2-carboxylic acid (intermediate 1, step 2), 4-[3-(4-fluoro-phenyl)-5-methoxymethyl-isoxazole-4-carbonyl]-1H-pyrrole-2-carboxylic acid (intermediate 13) was synthesized from 4-[3-(4-fluoro-phenyl)-5-methoxymethyl-isoxazole-4-carbonyl]-1H-pyrrole-2-carboxylic acid methyl ester through saponification with LiOH.H$_2$O. The title compound was obtained in 81% yield as red solid. (m/e): 343.2 (M$^-$; 100%).

Intermediate 14

4-(3,5-Diphenyl-isoxazole-4-carbonyl)-1H-pyrrole-2-carboxylic acid

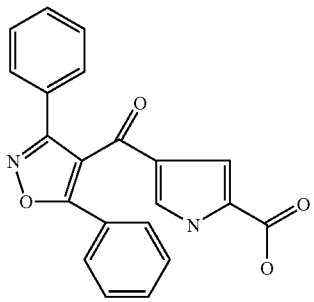

a) Step 1:

4-(1-Oxo-4-phenyl-but-2-ynyl)-1H-pyrrole-2-carboxylic acid methyl ester

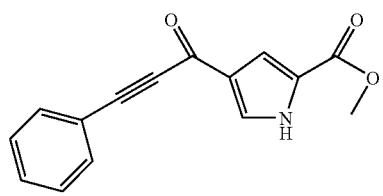

According to the procedure described for the synthesis of 4-(1-oxo-but-2-ynyl)-1H-pyrrole-2-carboxylic acid methyl ester (intermediate 2, step 1), 4-(1-oxo-4-phenyl-but-2-ynyl)-1H-pyrrole-2-carboxylic acid methyl ester was synthesized by the reaction of phenyl propynoyl chloride (J. Org. Chem. 68; 2003; 6810-6813) with 5-methyl-3-phenyl-isoxazole-4-carboxylic acid (commercially available) in 54% yield as light yellow solid. (m/e): 254.2 (M+; 100%).

b) Step 2:

4-(3,5-Diphenyl-isoxazole-4-carbonyl)-1H-pyrrole-2-carboxylic acid methyl ester

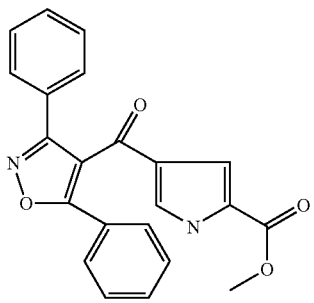

According to the procedure described for the synthesis of 4-(3-(4-bromo-phenyl)-5-methyl-isoxazole-4-carbonyl)-1H-pyrrole-2-carboxylic acid methyl ester (intermediate 2, step 2), 4-(3,5-diphenyl-isoxazole-4-carbonyl)-1H-pyrrole-2-carboxylic acid methyl ester was obtained from 4-(1-oxo-4-phenyl-but-2-ynyl)-1H-pyrrole-2-carboxylic acid methyl ester and N-hydroxybenzenecarboxymidoyl chloride (commercially available) in 61% yield as white solid. (m/e): 371.4 (M−; 100%).

c) Step 3:

According to the procedure described for the synthesis of 4-(5-methyl-3-phenyl-isoxazole-4-carbonyl)-1H-pyrrole-2-carboxylic acid (intermediate 1, step 2), 4-(3,5-diphenyl-isoxazole-4-carbonyl)-1H-pyrrole-2-carboxylic acid (intermediate 14) was synthesized from 4-(3,5-diphenyl-isoxazole-4-carbonyl)-1H-pyrrole-2-carboxylic acid methyl ester through saponification with LiOH.H$_2$O. The title compound was obtained in 81% yield as yellow solid.

Intermediate 15

4-[3-(4-Bromo-phenyl)-5-methyl-isoxazole-4-carbonyl]-1-methyl-1H-pyrrole-2-carboxylic acid

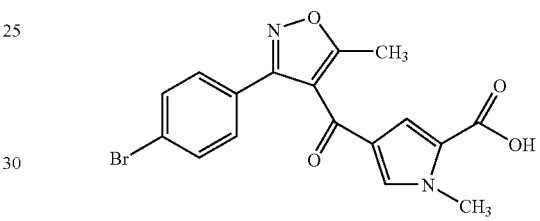

a) Step 1:

4-[3-(4-Bromo-phenyl)-5-methyl-isoxazole-4-carbonyl]-1-methyl-1H-pyrrole-2-carboxylic acid methyl ester

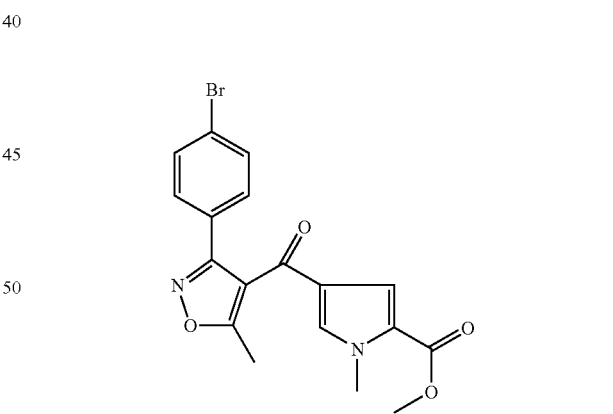

A mixture of 212 mg (0.5 mmol) 4-[3-(4-bromo-phenyl)-5-methyl-isoxazole-4-carbonyl]-1H-pyrrole-2-carboxylic acid methyl ester (intermediate 2, step 2), 28 mg (0.66 mmol) NaH and 116 mg (0.65 mmol) iodomethane was stirred at room temperature for 24 h. The mixture was then diluted with water and the product extracted with ethyl acetate. The combined organic extracts were then dried with Na$_2$SO$_4$ and evaporated to yield 133 mg (61%) of the title compound as a light yellow solid after purification by chromatography on silica gel eluting with ethyl acetate/heptane. (m/e): 403.3/405.2 (M+H, 100%).

b) Step 2:

According to the procedure described for the synthesis of 4-(5-methyl-3-phenyl-isoxazole-4-carbonyl)-1H-pyrrole-2-carboxylic acid (intermediate 1), 4-[3-(4-bromo-phenyl)-5-methyl-isoxazole-4-carbonyl]-1-methyl-1H-pyrrole-2-carboxylic acid was synthesised from 4-[3-(4-bromo-phenyl)-5-methyl-isoxazole-4-carbonyl]-1-methyl-1H-pyrrole-2-carboxylic acid methyl ester through saponification with LiOH.H$_2$O. The title compound was obtained in 90% yield as white solid. (m/e): 387.0/389.1 (M-H; 100%).

EXAMPLE 229

4-(5-Methyl-3-(4-Fluorophenyl)-isoxazole-4-carbonyl)-1-methyl-pyrrole-2-carboxylic acid (cyclopropylmethyl)-amide

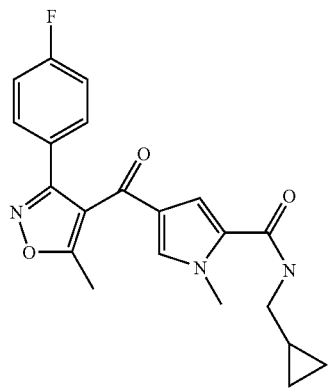

a) Step 1:

4-(5-methyl-3-(4-fluorophenyl)-isoxazole-4-carbonyl)-2-trichloroacetyl-1H-pyrrole

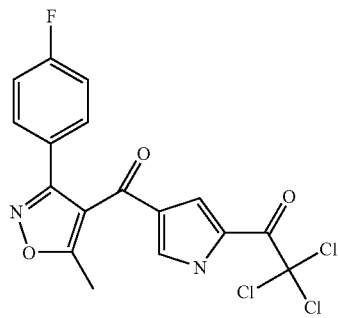

To a solution of 2.1 g (10 mmol) of 2-trichloroacetyl-1H-pyrrole (commercially available) in CH$_2$Cl$_2$ (35 mL) and nitromethane (17.5 mL), 1.66 g (12.5 mmol) of AlCl$_3$ was added in one portion. Then 2.96 g (12.5 mmol) of 5-methyl-3-(4-fluoro-phenyl)-isoxazole-4-carboxylic acid chloride (example 2, step 1) in 5 mL of CH$_2$Cl$_2$ was added dropwise. The reaction mixture was stirred at room temperature for 18 h before poured onto ice-water. The organic phase was separated, and the aqueous phase was extracted with diethyl ether. The combined organic solution was dried over Na$_2$SO$_4$, and evaporated to dryness. The obtained solid was washed extensively with petroleum ether to give 2.93 g 4-(5-methyl-3-phenyl-isoxazole-4-carbonyl)-2-trichloroacetyl-1H-pyrrole in 70% yield as yellow solid. (m/e): 414.8 (M$^+$; 100%).

b) Step 2:

4-(5-Methyl-3-(4-fluorophenyl)-isoxazole-4-carbonyl)-1H-pyrrole-2-carboxylic acid (cyclopropylmethyl)-amide

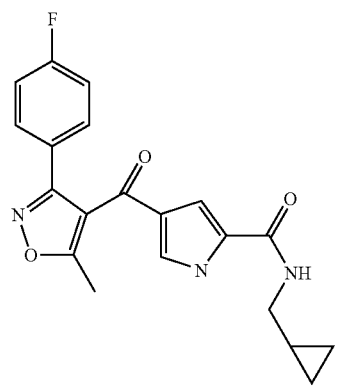

A mixture of 103.8 mg (0.25 mmol) 4-(5-methyl-3-(4-fluoro-phenyl)-isoxazole-4-carbonyl)-2-trichloroacetyl-1H-pyrrole, 18 mg (0.25 mmol) cyclpropyl-methylamine, and 25 mg (0.25 mmol) triethylamine was stirred overnight at 60° C. After cooling to room temperature, the reaction mixture was evaporated to dryness to afford 86.5 mg of the title compound in 94.3% yield as yellow solid. (m/e): 368.1 (M$^+$; 100%).

c) Step 3:

To a solution of 121 mg (0.33 mmol) 4-(5-methyl-3-(4-phenyl)-isoxazole-4-carbonyl)-1H-pyrrole-2-carboxylic acid cyclopropylmethyl-amide in dry DMF (2 mL) was added 48.71 mg (0.4 mmol) KOt-Bu and the mixture was stirred at room temperature for 30 minutes. The reaction was cooled to 0° C. and 70.24 mg (0.50 mmol) methyl iodide was added. The resulting mixture was stirred at room temperature for 8 h. Preparative HPLC (acetonitrile/water) purification gave 45 mg of 4-(5-methyl-3-(4-fluorophenyl)-isoxazole-4-carbonyl)-1-methyl-pyrrole-2-carboxylic acid (cyclopropylmethyl)-amide in 35.7% yield as white solid. (m/e): 382.1 (M$^+$; 100%).

EXAMPLE 230

4-(5-Methyl-3-(4-fluorophenyl)-isoxazole-4-carbonyl)-1-methyl-pyrrole-2-carboxylic acid (cyclopentyl)-amide

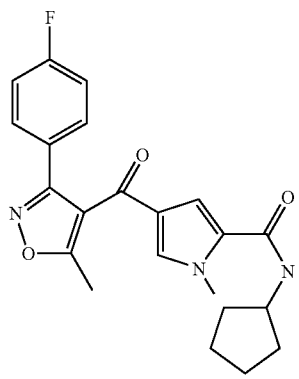

a) Step 1:

4-(5-Methyl-3-(4-fluorophenyl)-isoxazole-4-carbo-nyl)-1H-pyrrole-2-carboxylic acid (cyclopentyl)-amide

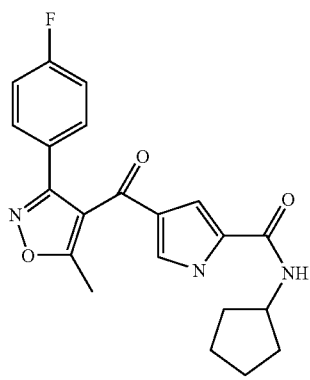

According to the procedure described for the synthesis of 4-(5-methyl-3-(4-fluorophenyl)-isoxazole-4-carbonyl)-1H-pyrrole-2-carboxylic acid (cyclopropylmethyl)-amide (Example 229, step 2), 4-(5-methyl-3-(4-fluorophenyl)-isoxazole-4-carbonyl)-1H-pyrrole-2-carboxylic acid (cyclopentyl)-amide was synthesized from 4-(5-methyl-3-(4-fluorophenyl)-isoxazole-4-carbonyl)-2-trichloroacetyl-1H-pyrrole and cyclopentylamine (commercially available) in 96% yield as white solid. (m/e): 382.1 ($M^+$; 100%).

b) Step 2

According to the procedure described for the synthesis of 4-(5-methyl-3-(4-fluorophenyl)-isoxazole-4-carbonyl)-1-methyl-pyrrole-2-carboxylic acid (cyclopropylmethyl)-amide (Example 229, step 3), 4-(5-methyl-3-(4-fluorophenyl)-isoxazole-4-carbonyl)-1-methyl-pyrrole-2-carboxylic acid (cyclopentyl)-amide was synthesized from 4-(5-methyl-3-(4-fluorophenyl)-isoxazole-4-carbonyl)-1H-pyrrole-2-carboxylic acid (cyclopentyl)-amide and methyl iodide in 29% yield as white solid. (m/e): 396.1 ($M^+$; 100%).

According to the procedure described for the synthesis of Example 2 further Aryl-isoxazole-4-carbonyl-pyrrole-2-carboxylic acid amide derivatives have been synthesised from the respective intermediates mentioned in table 1 and the respective amines mentioned in table 1.

The compounds are compiled in table 1 and comprise Example 3 to Example 237.

TABLE 1

| Example No. | Name | Structure | Starting materials | MW found [MH+] |
|---|---|---|---|---|
| 1 | 4-(5-Methyl-3-phenyl-isoxazole-4-carbonyl)-1H-pyrrole-2-carboxylic acid (3-morpholin-4-yl-propyl)-amide | 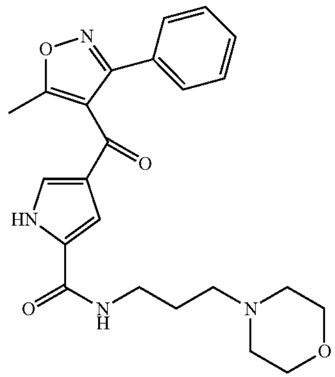 | 4-(5-Methyl-3-phenyl-isoxazole-4-carbonyl)-1H-pyrrole-2-carboxylic acid (intermediate 1) | 423.3 |
| 2 | 4-(5-Methyl-3-phenyl-isoxazole-4-carbonyl)-1H-pyrrole-2-carboxylic acid (pyridin-2-ylmethyl)-amide | 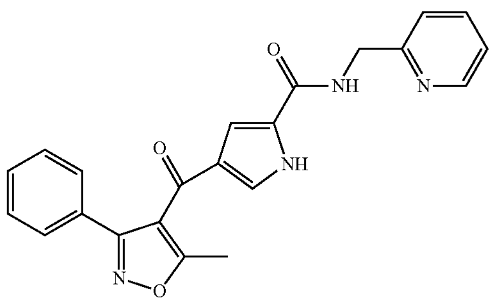 | 4-(5-Methyl-3-phenyl-isoxazole-4-carbonyl)-1H-pyrrole-2-carboxylic acid (intermediate 1) and pyridin-2-ylmethyl)-amine (commercially available) | 387.2 |

TABLE 1-continued

| Example No. | Structure | Name | Starting materials | MW found [MH+] |
|---|---|---|---|---|
| 3 | (structure) | 4-(5-Methyl-3-phenyl-isoxazole-4-carbonyl)-1H-pyrrole-2-carboxylic acid (pyridin-4-ylmethyl)-amide | 4-(5-Methyl-3-phenyl-isoxazole-4-carbonyl)-1H-pyrrole-2-carboxylic acid (intermediate 1) and pyridin-4-ylmethyl-amine (commercially available) | 387.4 |
| 4 | (structure) | 4-(5-Methyl-3-phenyl-isoxazole-4-carbonyl)-1H-pyrrole-2-carboxylic acid (pyridin-3-ylmethyl)-amide | 4-(5-Methyl-3-phenyl-isoxazole-4-carbonyl)-1H-pyrrole-2-carboxylic acid (intermediate 1) and pyridin-3-ylmethyl-amine (commercially available) | 387.4 |
| 5 | (structure) | 4-(5-Methyl-3-phenyl-isoxazole-4-carbonyl)-1H-pyrrole-2-carboxylic acid (2-morpholin-4-yl-ethyl)-amide | 4-(5-Methyl-3-phenyl-isoxazole-4-carbonyl)-1H-pyrrole-2-carboxylic acid (intermediate 1) and 2-morpholin-4-yl-ethyl-amine (commercially available) | 409.3 |

TABLE 1-continued

| Example No. | Name | Structure | Starting materials | MW found [MH+] |
|---|---|---|---|---|
| 6 | 1-[4-(5-Methyl-3-phenyl-isoxazole-4-carbonyl)-1H-pyrrole-2-carbonyl]piperidine-2-carboxylic acid ethyl ester | 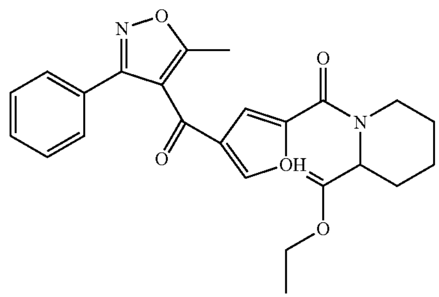 | 4-(5-Methyl-3-phenyl-isoxazole-4-carbonyl)-1H-pyrrole-2-carboxylic acid (intermediate 1) and piperidine-2-carboxylic acid ethyl ester (commercially available) | 436.4 |
| 7 | (2,6-Dimethyl-morpholin-4-yl)-[4-(5-methyl-3-phenyl-isoxazole-4-carbonyl)-1H-pyrrol-2-yl]-methanone | 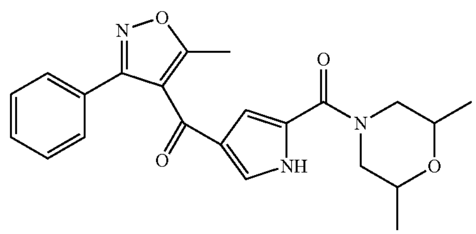 | 4-(5-Methyl-3-phenyl-isoxazole-4-carbonyl)-1H-pyrrole-2-carboxylic acid (intermediate 1) and 2,6-dimethyl-morpholine (commercially available) | 394.3 |
| 8 | (3-Hydroxy-pyrrolidin-1-yl)-[4-(5-methyl-3-phenyl-isoxazole-4-carbonyl)-1H-pyrrol-2-yl]-methanone | 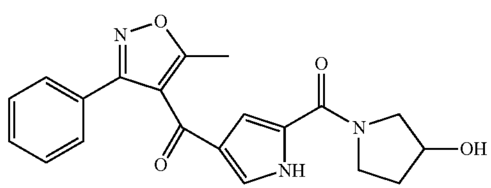 | 4-(5-Methyl-3-phenyl-isoxazole-4-carbonyl)-1H-pyrrole-2-carboxylic acid (intermediate 1) and 3-hydroxy-pyrrolidine (commercially available) | 464.3 |
| 9 | N-{1-[4-(5-Methyl-3-phenyl-isoxazole-4-carbonyl)-1H-pyrrole-2-carbonyl]-pyrrolidin-3-yl}-acetamide | 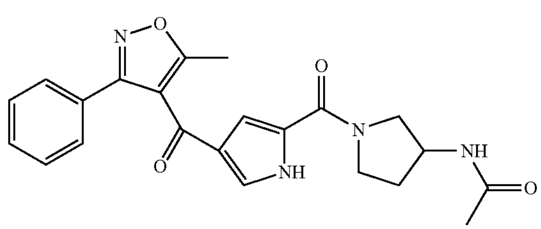 | 4-(5-Methyl-3-phenyl-isoxazole-4-carbonyl)-1H-pyrrole-2-carboxylic acid (intermediate 1) and N-pyrrolidin-3-yl-acetamide (commercially available) | 407.3 |

TABLE 1-continued

| Example No. | Structure | Name | Starting materials | MW found [MH+] |
|---|---|---|---|---|
| 10 | 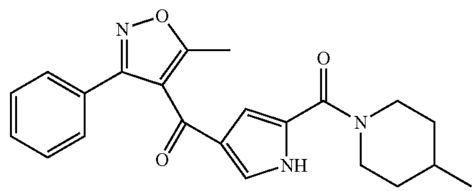 | [4-(5-Methyl-3-phenyl-isoxazole-4-carbonyl)-1H-pyrrol-2-yl]-(4-methyl-piperidin-1-yl)-methanone | 4-(5-Methyl-3-phenyl-isoxazole-4-carbonyl)-1H-pyrrole-2-carboxylic acid (intermediate 1) and 4-methyl-piperidine (commercially available) | 378.3 |
| 11 | 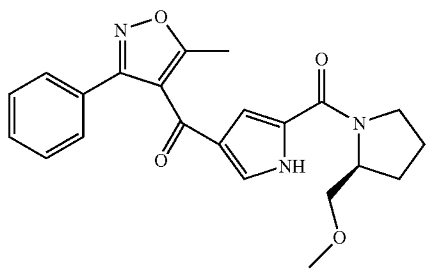 | ((R)-2-Methoxymethyl-pyrrolidin-1-yl)-[4-(5-methyl-3-phenyl-isoxazole-4-carbonyl)-1H-pyrrol-2-yl]-methanone | 4-(5-Methyl-3-phenyl-isoxazole-4-carbonyl)-1H-pyrrole-2-carboxylic acid (intermediate 1) and (R)-2-methoxymethyl-pyrrolidine (commercially available) | 394.3 |
| 12 | 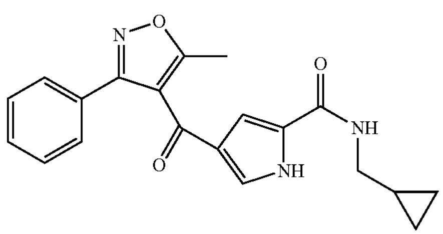 | 4-(5-Methyl-3-phenyl-isoxazole-4-carbonyl)-1H-pyrrole-2-carboxylic acid cyclopropylmethyl-amide | 4-(5-Methyl-3-phenyl-isoxazole-4-carbonyl)-1H-pyrrole-2-carboxylic acid (intermediate 1) and cyclopropylmethyl-amine (commercially available) | 350.3 |
| 13 | 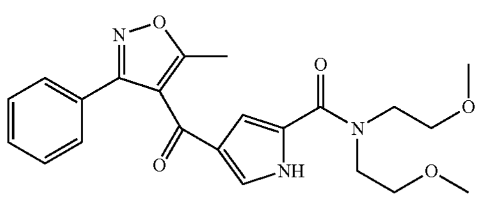 | 4-(5-Methyl-3-phenyl-isoxazole-4-carbonyl)-1H-pyrrole-2-carboxylic acid bis-(2-methoxy-ethyl)-amide | 4-(5-Methyl-3-phenyl-isoxazole-4-carbonyl)-1H-pyrrole-2-carboxylic acid (intermediate 1) and bis-(2-methoxy-ethyl)-amine (commercially available) | 412.4 |

TABLE 1-continued

| Example No. | Structure | Name | Starting materials | MW found [MH+] |
|---|---|---|---|---|
| 14 | 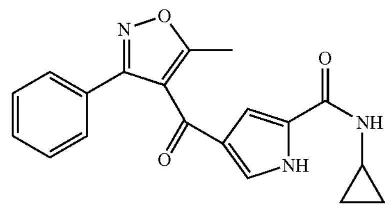 | 4-(5-Methyl-3-phenyl-isoxazole-4-carbonyl)-1H-pyrrole-2-carboxylic acid cyclopropylamide | 4-(5-Methyl-3-phenyl-isoxazole-4-carbonyl)-1H-pyrrole-2-carboxylic acid (intermediate 1) and cyclopropylamine (commercially available) | 336.3 |
| 15 | 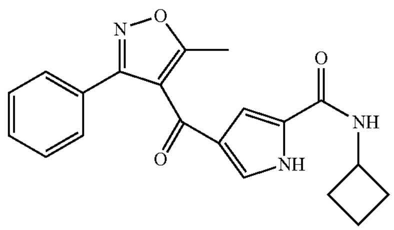 | 4-(5-Methyl-3-phenyl-isoxazole-4-carbonyl)-1H-pyrrole-2-carboxylic acid cyclobutylamide | 4-(5-Methyl-3-phenyl-isoxazole-4-carbonyl)-1H-pyrrole-2-carboxylic acid (intermediate 1) and cyclobutylamine (commercially available) | 350.3 |
| 16 | 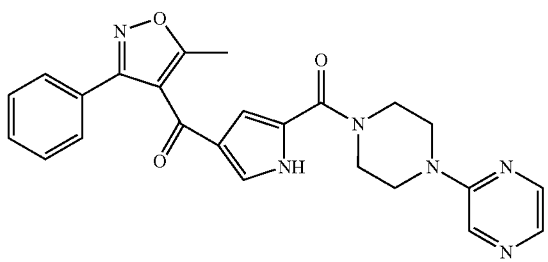 | [4-(5-Methyl-3-phenyl-isoxazole-4-carbonyl)-1H-pyrrole-2-yl]-(2,3,5,6-tetrahydro-[1,2']bipyrazinyl-4-yl)-methanone | 4-(5-Methyl-3-phenyl-isoxazole-4-carbonyl)-1H-pyrrole-2-carboxylic acid (intermediate 1) and 3,4,5,6-tetrahydro-2H-[1,2']bipyrazine (commercially available) | 443.3 |

TABLE 1-continued

| Example No. | Structure | Name | Starting materials | MW found [MH+] |
|---|---|---|---|---|
| 17 | 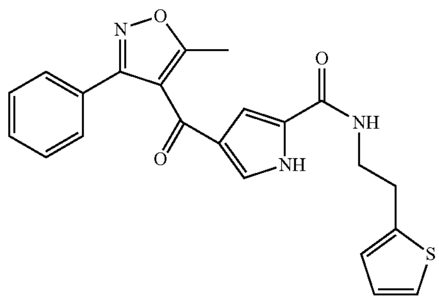 | 4-(5-Methyl-3-phenyl-isoxazole-4-carbonyl)-1H-pyrrole-2-carboxylic acid (2-thiophen-2-yl-ethyl)-amide | 4-(5-Methyl-3-phenyl-isoxazole-4-carbonyl)-1H-pyrrole-2-carboxylic acid (intermediate 1) and 2-thiophen-2-yl-ethyl-amine (commercially available) | 406.3 |
| 18 | 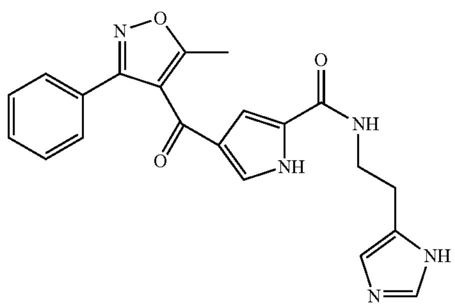 | 4-(5-Methyl-3-phenyl-isoxazole-4-carbonyl)-1H-pyrrole-2-carboxylic acid [2-(1H-imidazol-4-yl)-ethyl]-amide | 4-(5-Methyl-3-phenyl-isoxazole-4-carbonyl)-1H-pyrrole-2-carboxylic acid (intermediate 1) and 2-(1H-imidazol-4-yl)-ethyl-amine (commercially available) | 390.3 |
| 19 | 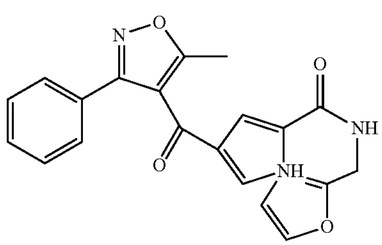 | 4-(5-Methyl-3-phenyl-isoxazole-4-carbonyl)-1H-pyrrole-2-carboxylic acid (furan-2-ylmethyl)-amide | 4-(5-Methyl-3-phenyl-isoxazole-4-carbonyl)-1H-pyrrole-2-carboxylic acid (intermediate 1) and furan-2-ylmethyl-amine (commercially available) | 376.2 |

TABLE 1-continued

| Example No. | Structure | Name | Starting materials | MW found [MH+] |
|---|---|---|---|---|
| 20 | 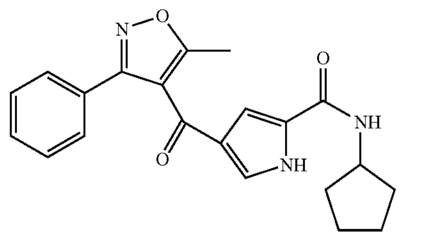 | 4-(5-Methyl-3-phenyl-isoxazole-4-carbonyl)-1H-pyrrole-2-carboxylic acid cyclopentylamide | 4-(5-Methyl-3-phenyl-isoxazole-4-carbonyl)-1H-pyrrole-2-carboxylic acid (intermediate 1) and cyclopentylamine (commercially available) | 364.3 |
| 21 | 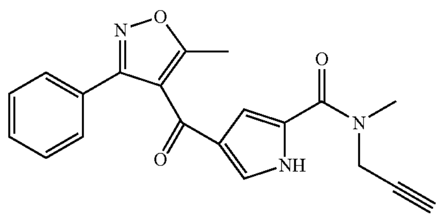 | 4-(5-Methyl-3-phenyl-isoxazole-4-carbonyl)-1H-pyrrole-2-carboxylic acid methyl-prop-2-ynyl-amide | 4-(5-Methyl-3-phenyl-isoxazole-4-carbonyl)-1H-pyrrole-2-carboxylic acid (intermediate 1) and methyl-prop-2-ynyl-amine (commercially available) | 348.2 |
| 22 | 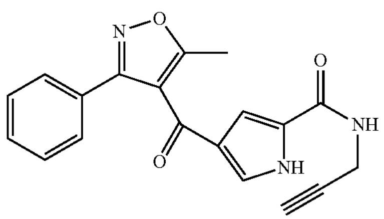 | 4-(5-Methyl-3-phenyl-isoxazole-4-carbonyl)-1H-pyrrole-2-carboxylic acid prop-2-ynylamide | 4-(5-Methyl-3-phenyl-isoxazole-4-carbonyl)-1H-pyrrole-2-carboxylic acid (intermediate 1) and prop-2-ynylami (commercially available) | 334.3 |
| 23 | 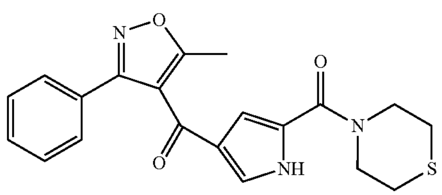 | [4-(5-Methyl-3-phenyl-isoxazole-4-carbonyl)-1H-pyrrol-2-yl]-thiomorpholin-4-yl-methanone | 4-(5-Methyl-3-phenyl-isoxazole-4-carbonyl)-1H-pyrrole-2-carboxylic acid (intermediate 1) and thiomorpholine (commercially available) | 382.2 |

TABLE 1-continued

| Example No. | Structure | Name | Starting materials | MW found [MH+] |
|---|---|---|---|---|
| 24 | 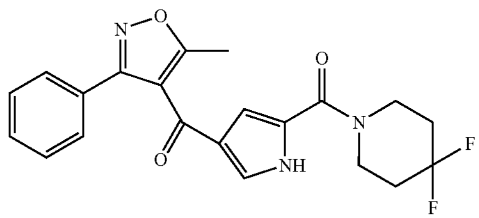 | (4,4-Difluoro-piperidin-1-yl)-[4-(5-methyl-3-phenyl-isoxazole-4-carbonyl)-1H-pyrrol-2-yl]-methanone | 4-(5-Methyl-3-phenyl-isoxazole-4-carbonyl)-1H-pyrrole-2-carboxylic acid (intermediate 1) and 4,4-difluoro-piperidine (commercially available) | 400.3 |
| 25 | 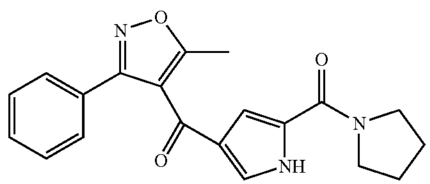 | [4-(5-Methyl-3-phenyl-isoxazole-4-carbonyl)-1H-pyrrol-2-yl]-pyrrolidin-1-yl-methanone | 4-(5-Methyl-3-phenyl-isoxazole-4-carbonyl)-1H-pyrrole-2-carboxylic acid (intermediate 1) and pyrrolidine (commercially available) | 350.3 |
| 26 | 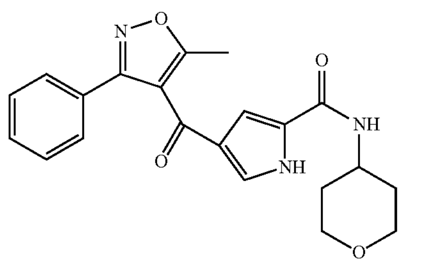 | 4-(5-Methyl-3-phenyl-isoxazole-4-carbonyl)-1H-pyrrole-2-carboxylic acid (tetrahydro-pyran-4-yl)-amide | 4-(5-Methyl-3-phenyl-isoxazole-4-carbonyl)-1H-pyrrole-2-carboxylic acid (intermediate 1) and tetrahydro-pyran-4-yl-amine (commercially available) | 380.3 |
| 27 | 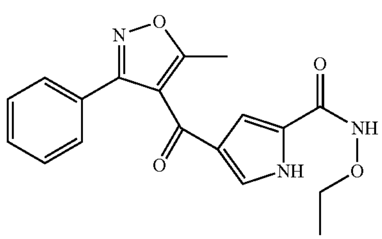 | 4-(5-Methyl-3-phenyl-isoxazole-4-carbonyl)-1H-pyrrole-2-carboxylic acid ethoxy-amide | 4-(5-Methyl-3-phenyl-isoxazole-4-carbonyl)-1H-pyrrole-2-carboxylic acid (intermediate 1) and ethoxy-amine (commercially available) | 340 |

TABLE 1-continued

| Example No. | Structure | Name | Starting materials | MW found [MH+] |
|---|---|---|---|---|
| 28 | 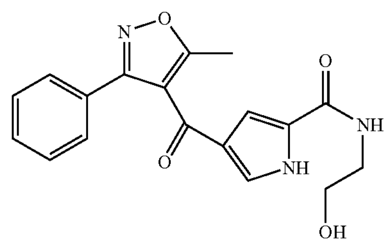 | 4-(5-Methyl-3-phenyl-isoxazole-4-carbonyl)-1H-pyrrole-2-carboxylic acid (2-hydroxy-ethyl)-amide | 4-(5-Methyl-3-phenyl-isoxazole-4-carbonyl)-1H-pyrrole-2-carboxylic acid (intermediate 1) and 2-hydroxy-ethyl-amine (commercially available) | 340.1 |
| 29 | 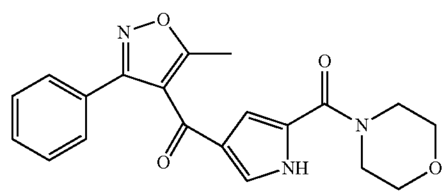 | [4-(5-Methyl-3-phenyl-isoxazole-4-carbonyl)-1H-pyrrol-2-yl]-morpholin-4-yl-methanone | 4-(5-Methyl-3-phenyl-isoxazole-4-carbonyl)-1H-pyrrole-2-carboxylic acid (intermediate 1) and morpholine (commercially available) | 366.2 |
| 30 | 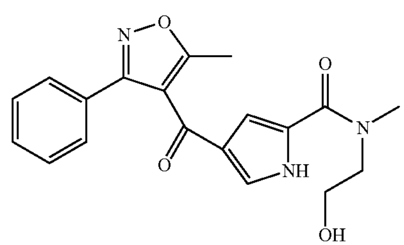 | 4-(5-Methyl-3-phenyl-isoxazole-4-carbonyl)-1H-pyrrole-2-carboxylic acid (2-hydroxy-ethyl)-methyl-amide | 4-(5-Methyl-3-phenyl-isoxazole-4-carbonyl)-1H-pyrrole-2-carboxylic acid (intermediate 1) and 2-hydroxy-ethyl)-methyl-amine (commercially available) | 354.3 |
| 31 | 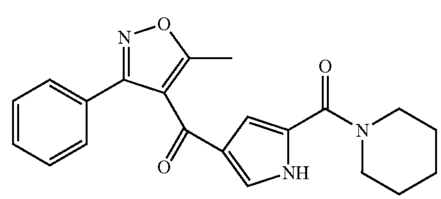 | [4-(5-Methyl-3-phenyl-isoxazole-4-carbonyl)-1H-pyrrol-2-yl]-piperidin-1-yl-methanone | 4-(5-Methyl-3-phenyl-isoxazole-4-carbonyl)-1H-pyrrole-2-carboxylic acid (intermediate 1) and piperidine (commercially available) | 364.3 |

TABLE 1-continued

| Example No. | Structure | Name | Starting materials | MW found [MH+] |
|---|---|---|---|---|
| 32 | 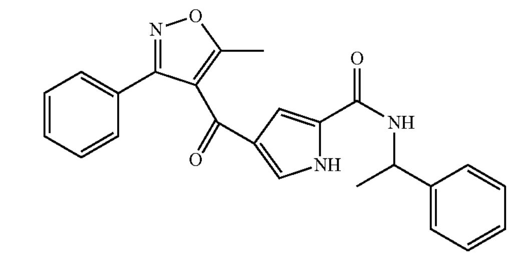 | 4-(5-Methyl-3-phenyl-isoxazole-4-carbonyl)-1H-pyrrole-2-carboxylic acid (1-phenyl-ethyl)-amide | 4-(5-Methyl-3-phenyl-isoxazole-4-carbonyl)-1H-pyrrole-2-carboxylic acid (intermediate 1) and 1-phenyl-ethyl-amine (commercially available) | 400.3 |
| 33 | 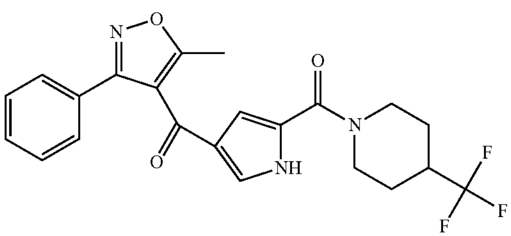 | [4-(5-Methyl-3-phenyl-isoxazole-4-carbonyl)-1H-pyrrol-2-yl]-(4-trifluoromethyl-piperidin-1-yl)-methanone | 4-(5-Methyl-3-phenyl-isoxazole-4-carbonyl)-1H-pyrrole-2-carboxylic acid (intermediate 1) and 4-triflouromethyl-piperidine (commercially available) | 432.3 |
| 34 | 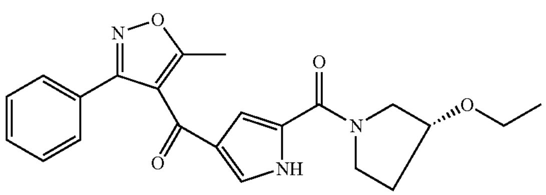 | ((R)-3-Ethoxy-pyrrolidin-1-yl)-[4-(5-methyl-3-phenyl-isoxazole-4-carbonyl)-1H-pyrrol-2-yl]-methanone | 4-(5-Methyl-3-phenyl-isoxazole-4-carbonyl)-1H-pyrrole-2-carboxylic acid (intermediate 1) and (R)-3-Ethoxy-pyrrolidine (commercially available) | 394.2 |
| 35 | 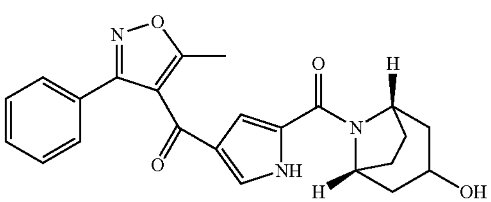 | ((1S,5R)-3-Hydroxy-8-aza-bicyclo[3.2.1]oct-8-yl)-[4-(5-methyl-3-phenyl-isoxazole-4-carbonyl)-1H-pyrrol-2-yl]-methanone | 4-(5-Methyl-3-phenyl-isoxazole-4-carbonyl)-1H-pyrrole-2-carboxylic acid (intermediate 1) and (1S,5R)-3-hydroxy-8-aza-bicyclo[3.2.1]octane (commercially available) | 406.4 |

TABLE 1-continued

| Example No. | Structure | Name | Starting materials | MW found [MH+] |
|---|---|---|---|---|
| 36 | 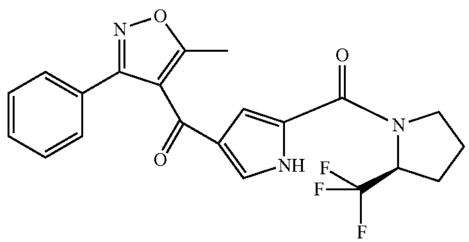 | [4-(5-Methyl-3-phenyl-isoxazole-4-carbonyl)-1H-pyrrol-2-yl]-[(S)-2-trifluoromethyl-pyrrolidin-1-yl]-methanone | 4-(5-Methyl-3-phenyl-isoxazole-4-carbonyl)-1H-pyrrole-2-carboxylic acid (intermediate 1) and (S)-2-trifluoromethyl-pyrrolidine (commercially available) | 418.1 |
| 37 | 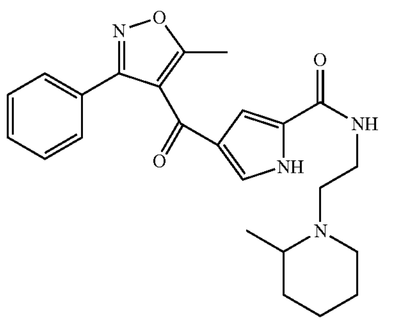 | 4-(5-Methyl-3-phenyl-isoxazole-4-carbonyl)-1H-pyrrole-2-carboxylic acid [2-(2-methyl-piperidin-1-yl)-ethyl]-amide | 4-(5-Methyl-3-phenyl-isoxazole-4-carbonyl)-1H-pyrrole-2-carboxylic acid (intermediate 1) and 2-(2-methyl-piperidin-1-yl)-ethyl]-amine (commercially available) | 421 |
| 38 | 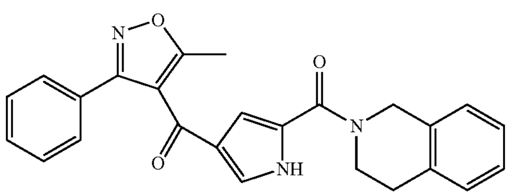 | (3,4-Dihydro-1H-isoquinolin-2-yl)-[4-(5-methyl-3-phenyl-isoxazole-4-carbonyl)-1H-pyrrol-2-yl]-methanone | 4-(5-Methyl-3-phenyl-isoxazole-4-carbonyl)-1H-pyrrole-2-carboxylic acid (intermediate 1) and 3,4-dihydro-1H-isoquinoline (commercially available) | 412.1 |

TABLE 1-continued

| Example No. | Structure | Name | Starting materials | MW found [MH+] |
|---|---|---|---|---|
| 39 | 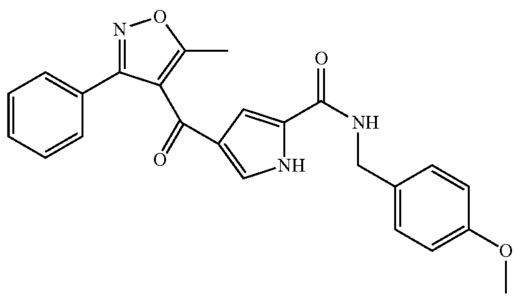 | 4-(5-Methyl-3-phenyl-isoxazole-4-carbonyl)-1H-pyrrole-2-carboxylic acid 4-methoxy-benzylamide | 4-(5-Methyl-3-phenyl-isoxazole-4-carbonyl)-1H-pyrrole-2-carboxylic acid (intermediate 1) and 4-methoxy-benzylamine (commercially available) | 416.1 |
| 40 | 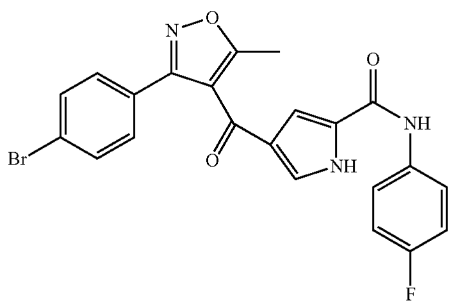 | 4-[3-(4-Bromo-phenyl)-5-methyl-isoxazole-4-carbonyl]-1H-pyrrole-2-carboxylic acid (4-fluoro-phenyl)-amide | 4-[3-(4-Bromo-phenyl)-5-methyl-isoxazole-4-carbonyl]-1H-pyrrole-2-carboxylic acid (intermediate 2) and 4-fluoro-aniline (commercially available) | 466 |
| 41 | 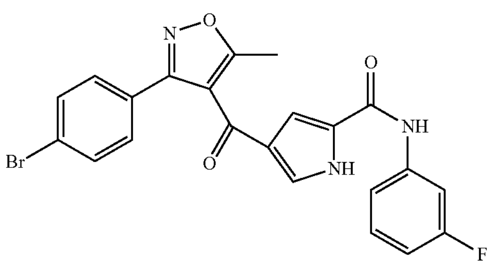 | 4-[3-(4-Bromo-phenyl)-5-methyl-isoxazole-4-carbonyl]-1H-pyrrole-2-carboxylic acid (3-fluoro-phenyl)-amide | 4-[3-(4-Bromo-phenyl)-5-methyl-isoxazole-4-carbonyl]-1H-pyrrole-2-carboxylic acid (intermediate 2) and 3-fluoro-aniline (commercially available) | 466 |

TABLE 1-continued

| Example No. | Structure | Name | Starting materials | MW found [MH+] |
|---|---|---|---|---|
| 42 | 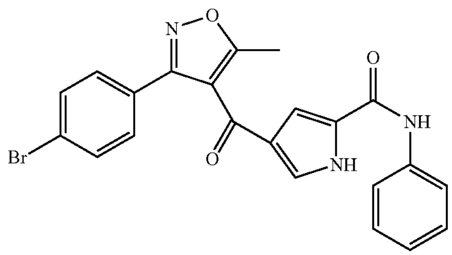 | 4-[3-(4-Bromo-phenyl)-5-methyl-isoxazole-4-carbonyl]-1H-pyrrole-2-carboxylic acid phenylamide | 4-[3-(4-Bromo-phenyl)-5-methyl-isoxazole-4-carbonyl]-1H-pyrrole-2-carboxylic acid (intermediate 2) and aniline (commercially available) | 448 |
| 43 | 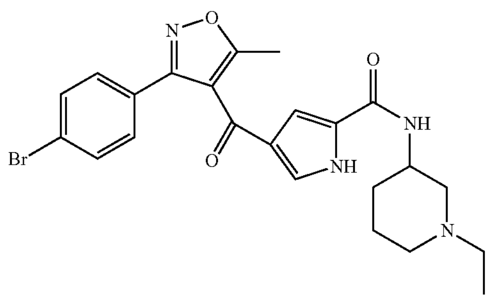 | 4-[3-(4-Bromo-phenyl)-5-methyl-isoxazole-4-carbonyl]-1H-pyrrole-2-carboxylic acid (1-ethyl-piperidin-3-yl)-amide | 4-[3-(4-Bromo-phenyl)-5-methyl-isoxazole-4-carbonyl]-1H-pyrrole-2-carboxylic acid (intermediate 2) and 1-ethyl-piperidin-3-yl)-amine (commercially available) | 487.2 |
| 44 | 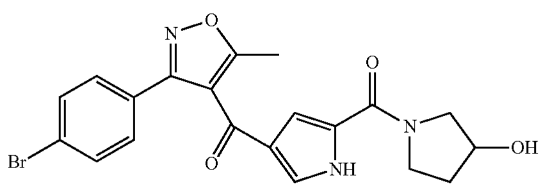 | [3-(4-Bromo-phenyl)-5-methyl-isoxazol-4-yl]-[5-(3-hydroxy-pyrrolidine-1-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and 3-hydroxy-pyrrolidine (commercially available) | 444.2 |
| 45 | 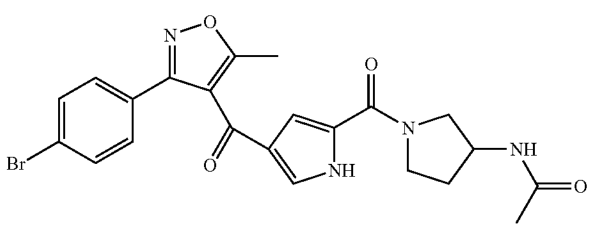 | N-(1-{4-[3-(4-Bromo-phenyl)-5-methyl-isoxazole-4-carbonyl]-1H-pyrrole-2-carbonyl}-pyrrolidin-3-yl)-acetamide | 4-[3-(4-Bromo-phenyl)-5-methyl-isoxazole-4-carbonyl]-1H-pyrrole-2-carboxylic acid (intermediate 2) and N-pyrrolidin-3-yl-acetamide (commercially available) | 485.2 |

TABLE 1-continued

| Example No. | Structure | Name | Starting materials | MW found [MH+] |
|---|---|---|---|---|
| 46 | 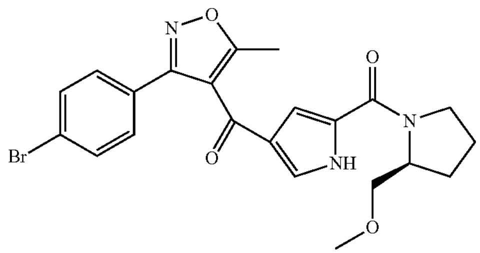 | [3-(4-Bromo-phenyl)-5-methyl-isoxazol-4-yl]-[5-((R)-2-methoxymethyl-pyrrolidine-1-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and (R)-2-methoxymethyl-pyrrolidine (commercially available) | 472.2 |
| 47 | 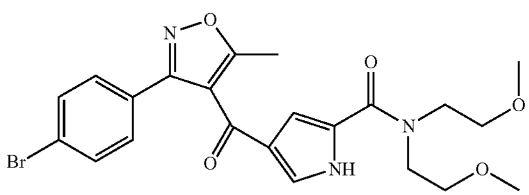 | 4-[3-(4-Bromo-phenyl)-5-methyl-isoxazole-4-carbonyl]-1H-pyrrole-2-carboxylic acid bis-(2-methoxy-ethyl)-amide | 4-[3-(4-Bromo-phenyl)-5-methyl-isoxazole-4-carbonyl]-1H-pyrrole-2-carboxylic acid (intermediate 2) and 2-methoxy-ethyl-amine (commercially available) | 490.1 |
| 48 | 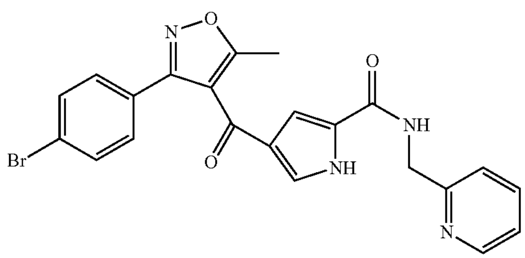 | 4-[3-(4-Bromo-phenyl)-5-methyl-isoxazole-4-carbonyl]-1H-pyrrole-2-carboxylic acid (pyridin-2-ylmethyl)-amide | 4-[3-(4-Bromo-phenyl)-5-methyl-isoxazole-4-carbonyl]-1H-pyrrole-2-carboxylic acid (intermediate 2) and pyridin-2-ylmethyl-amine (commercially available) | 463.1 |
| 49 | 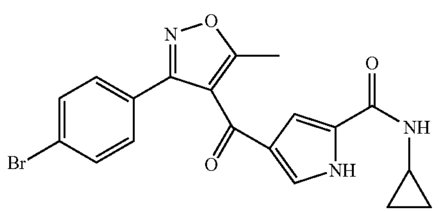 | 4-[3-(4-Bromo-phenyl)-5-methyl-isoxazole-4-carbonyl]-1H-pyrrole-2-carboxylic acid cyclopropylamide | 4-[3-(4-Bromo-phenyl)-5-methyl-isoxazole-4-carbonyl]-1H-pyrrole-2-carboxylic acid (intermediate 2) and cyclopropylamine (commercially available) | 416.2 |

TABLE 1-continued

| Example No. | Structure | Name | Starting materials | MW found [MH+] |
|---|---|---|---|---|
| 50 | 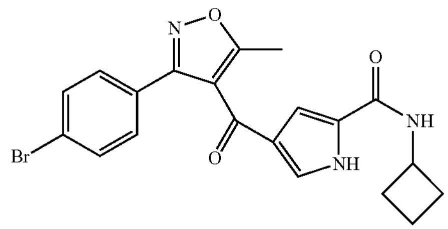 | 4-[3-(4-Bromo-phenyl)-5-methyl-isoxazol-4-yl]-carbonyl]-1H-pyrrole-2-carboxylic acid cyclobutylamide | 4-[3-(4-Bromo-phenyl)-5-methyl-isoxazole-4-carbo-nyl]-1H-pyrrole-2-carboxylic acid (intermediate 2) and cyclobutylamine (commercially available) | 428.2 |
| 51 | 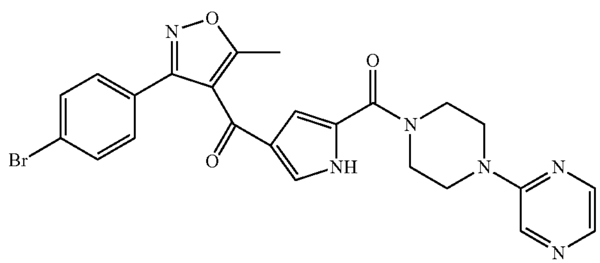 | [3-(4-Bromo-phenyl)-5-methyl-isoxazol-4-yl]-[5-(2,3,5,6-tetrahydro-[1,2']bipyrazinyl-4-carbonyl)-1H-pyrrol-3-yl]-methanone | 4-[3-(4-Bromo-phenyl)-5-methyl-isoxazole-4-carbo-nyl]-1H-pyrrole-2-carboxylic acid (intermediate 2) and 3,4,5,6-tetrahydro-2H-[1,2']bipyrazine (commercially available) | 523.3 |
| 52 | 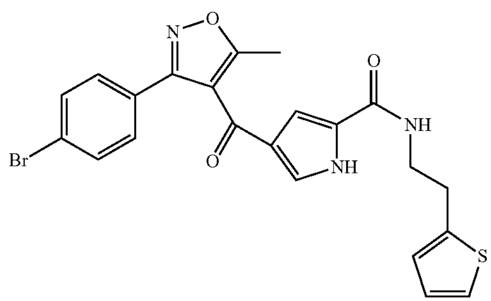 | 4-[3-(4-Bromo-phenyl)-5-methyl-isoxazole-4-carbonyl]-1H-pyrrole-2-carboxylic acid (2-thiophen-2-yl-ethyl)-amide | 4-[3-(4-Bromo-phenyl)-5-methyl-isoxazole-4-carbonyl]-1H-pyrrole-2-carboxylic acid (intermediate 2) and 2-thiophen-2-yl-ethyl-amine (commercially available) | 484.2 |

TABLE 1-continued

| Example No. | Structure | Name | Starting materials | MW found [MH+] |
|---|---|---|---|---|
| 53 | 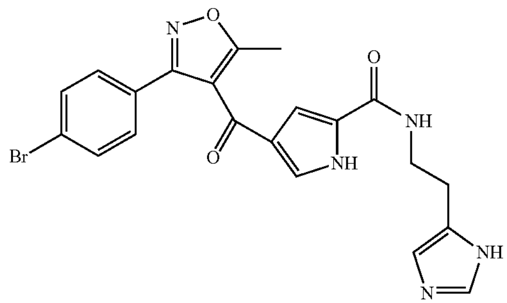 | 4-[3-(4-Bromo-phenyl)-5-methyl-isoxazole-4-carbonyl]-1H-pyrrole-2-carboxylic acid [2-(1H-imidazol-4-yl)-ethyl]-amide | 4-[3-(4-Bromo-phenyl)-5-methyl-isoxazole-4-carbonyl]-1H-pyrrole-2-carboxylic acid (intermediate 2) and 2-(1H-imidazol-4-yl)-ethyl-amine (commercially available) | 468.2 |
| 54 | 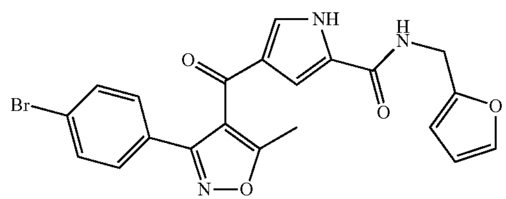 | 4-[3-(4-Bromo-phenyl)-5-methyl-isoxazole-4-carbonyl]-1H-pyrrole-2-carboxylic acid (furan-2-ylmethyl)-amide | 4-[3-(4-Bromo-phenyl)-5-methyl-isoxazole-4-carbonyl]-1H-pyrrole-2-carboxylic acid (intermediate 2) and furan-2-ylmethyl-amine (commercially available) | 465.1 |
| 55 | 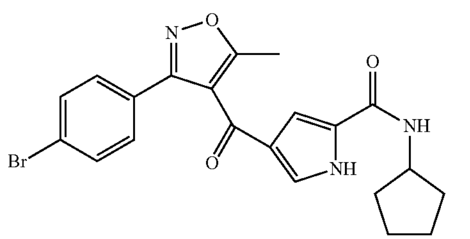 | 4-[3-(4-Bromo-phenyl)-5-methyl-isoxazole-4-carbonyl]-1H-pyrrole-2-carboxylic acid cyclopentylamide | 4-[3-(4-Bromo-phenyl)-5-methyl-isoxazole-4-carbonyl]-1H-pyrrole-2-carboxylic acid (intermediate 2) and cyclopentylamine (commercially available) | 442.3 |
| 56 | 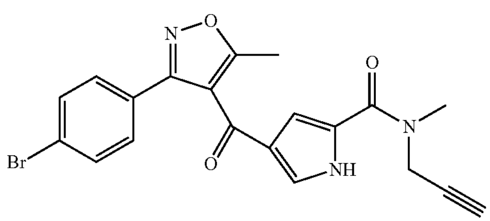 | 4-[3-(4-Bromo-phenyl)-5-methyl-isoxazole-4-carbonyl]-1H-pyrrole-2-carboxylic acid methyl-prop-2-ynyl-amide | 4-[3-(4-Bromo-phenyl)-5-methyl-isoxazole-4-carbonyl]-1H-pyrrole-2-carboxylic acid (intermediate 2) and methyl-prop-2-ynyl-amine (commercially available) | 428.1 |

TABLE 1-continued

| Example No. | Name | Starting materials | MW found [MH+] |
|---|---|---|---|
| 57 | 4-[3-(4-Bromo-phenyl)-5-methyl-isoxazol-4-carbonyl]-1H-pyrrole-2-carboxylic acid prop-2-ynylamide | 4-[3-(4-Bromo-phenyl)-5-methyl-isoxazole-4-carbonyl]-1H-pyrrole-2-carboxylic acid (intermediate 2) and prop-2-ynylami (commercially available) | 414.2 |
| 58 | [3-(4-Bromo-phenyl)-5-methyl-isoxazol-4-yl]-[5-(thiomorpholine-4-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and thiomorpholine (commercially available) | 462.1 |
| 59 | [3-(4-Bromo-phenyl)-5-methyl-isoxazol-4-yl]-[5-(4,4-difluoro-piperidine-1-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and 4,4-Difluoro-piperidine (commercially available) | 478.1 |
| 60 | [3-(4-Bromo-phenyl)-5-methyl-isoxazol-4-yl]-[5-(pyrrolidine-1-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and pyrrolidine (commercially available) | 430.2 |

TABLE 1-continued

| Example No. | Structure | Name | Starting materials | MW found [MH+] |
|---|---|---|---|---|
| 61 | 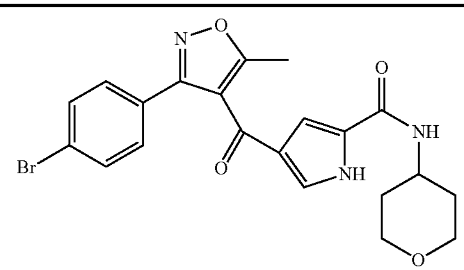 | 4-[3-(4-Bromo-phenyl)-5-methyl-isoxazole-4-carbonyl]-1H-pyrrole-2-carboxylic acid (tetrahydro-pyran-4-yl)-amide | 4-[3-(4-Bromo-phenyl)-5-methyl-isoxazole-4-carbonyl]-1H-pyrrole-2-carboxylic acid (intermediate 2) and tetrahydro-pyran-4-yl-amine (commercially available) | 458.2 |
| 62 | 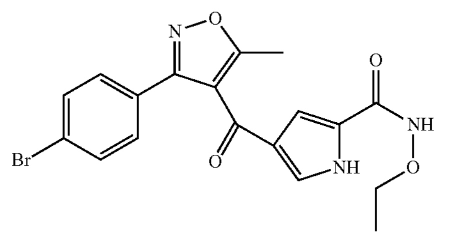 | 4-[3-(4-Bromo-phenyl)-5-methyl-isoxazole-4-carbonyl]-1H-pyrrole-2-carboxylic acid ethoxy-amide | 4-[3-(4-Bromo-phenyl)-5-methyl-isoxazole-4-carbonyl]-1H-pyrrole-2-carboxylic acid (intermediate 2) and ethoxy-amine (commercially available) | 420.1 |
| 63 | 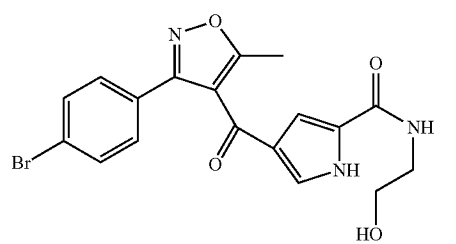 | 4-[3-(4-Bromo-phenyl)-5-methyl-isoxazole-4-carbonyl]-1H-pyrrole-2-carboxylic acid (2-hydroxy-ethyl)-amide | 4-[3-(4-Bromo-phenyl)-5-methyl-isoxazole-4-carbonyl]-1H-pyrrole-2-carboxylic acid (intermediate 2) and 2-hydroxy-ethyl-amine (commercially available) | 418.1 |
| 64 | 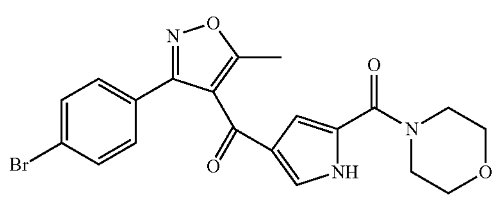 | [3-(4-Bromo-phenyl)-5-methyl-isoxazole-4-yl]-[5-(morpholine-4-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and morpholine (commercially available) | 444.2 |

TABLE 1-continued

| Example No. | Structure | Name | Starting materials | MW found [MH+] |
|---|---|---|---|---|
| 65 | 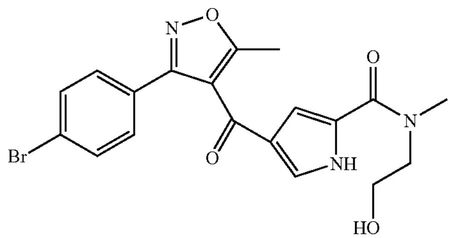 | 4-[3-(4-Bromo-phenyl)-5-methyl-isoxazole-4-carbonyl]-1H-pyrrole-2-carboxylic acid (2-hydroxy-ethyl)-methyl-amide | 4-[3-(4-Bromo-phenyl)-5-methyl-isoxazole-4-carbonyl]-1H-pyrrole-2-carboxylic acid (intermediate 2) and 2-hydroxy-ethyl-methyl-amine (commercially available) | 432.2 |
| 66 | 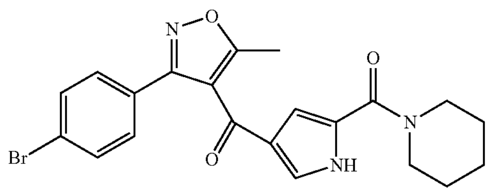 | [3-(4-Bromo-phenyl)-5-methyl-isoxazole-4-yl]-[5-(piperidine-1-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and piperidine (commercially available) | 444.2 |
| 67 | 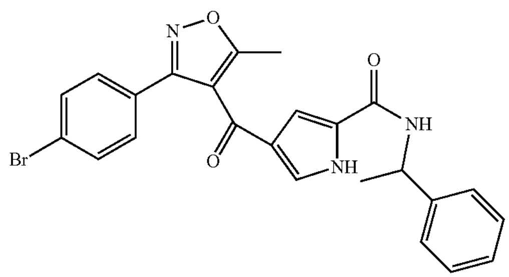 | 4-[3-(4-Bromo-phenyl)-5-methyl-isoxazole-4-carbonyl]-1H-pyrrole-2-carboxylic acid (1-phenyl-ethyl)-amide | 4-[3-(4-Bromo-phenyl)-5-methyl-isoxazole-4-carbonyl]-1H-pyrrole-2-carboxylic acid (intermediate 2) and 1-phenyl-ethyl-amine (commercially available) | 478.1 |
| 68 | 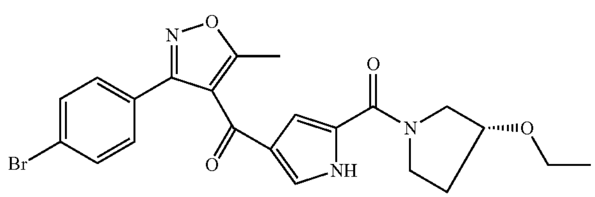 | [3-(4-Bromo-phenyl)-5-methyl-isoxazol-4-yl]-[5-((R)-3-ethoxy-pyrrolidine-1-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and (R)-3-ethoxy-pyrrolidine (commercially available) | 474.1 |

TABLE 1-continued

| Example No. | Structure | Name | Starting materials | MW found [MH⁺] |
|---|---|---|---|---|
| 69 | 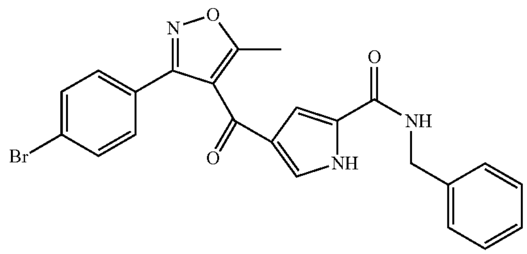 | 4-[3-(4-Bromo-phenyl)-5-methyl-isoxazole-4-carbonyl]-1H-pyrrole-2-carboxylic acid benzylamide | 4-[3-(4-Bromo-phenyl)-5-methyl-isoxazole-4-carbonyl]-1H-pyrrole-2-carboxylic acid (intermediate 2) and benzylamine (commercially available) | 464.1 |
| 70 | 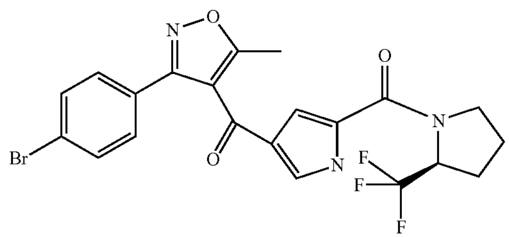 | [3-(4-Bromo-phenyl)-5-methyl-isoxazol-4-yl]-[5-((S)-2-trifluoromethyl-pyrrolidine-1-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and (S)-2-trifluoro-methyl-pyrrolidine (commercially available) | 496.2 |
| 71 | 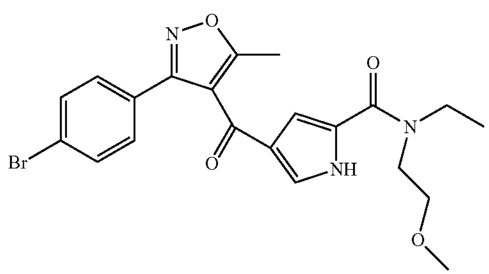 | 4-[3-(4-Bromo-phenyl)-5-methyl-isoxazole-4-carbonyl]-1H-pyrrole-2-carboxylic acid ethyl-(2-methoxy-ethyl)-amide | 4-[3-(4-Bromo-phenyl)-5-methyl-isoxazole-4-carbonyl]-1H-pyrrole-2-carboxylic acid (intermediate 2) and 2-methoxy-ethyl-amine (commercially available) | 462.2 |

TABLE 1-continued

| Example No. | Structure | Name | Starting materials | MW found [MH+] |
|---|---|---|---|---|
| 72 | 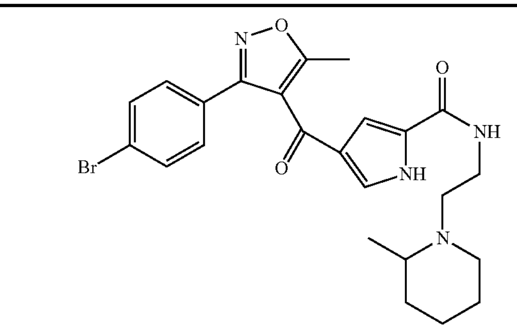 | 4-[3-(4-Bromo-phenyl)-5-methyl-isoxazole-4-carbonyl]-1H-pyrrole-2-carboxylic acid [2-(2-methyl-piperidin-1-yl)-ethyl]-amide | 4-[3-(4-Bromo-phenyl)-5-methyl-isoxazole-4-carbonyl]-1H-pyrrole-2-carboxylic acid (intermediate 2) and 2-(2-methyl-piperidin-1-yl)-ethyl]-amine (commercially available) | 499.1 |
| 73 | 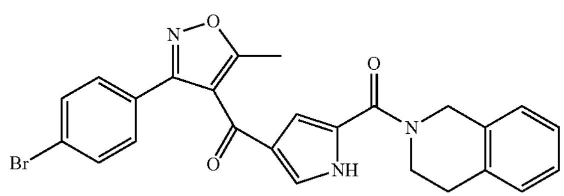 | [3-(4-Bromo-phenyl)-5-methyl-isoxazol-4-yl]-[5-(3,4-dihydro-1H-isoquinoline-2-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and 3,4-dihydro-1H-isoquinoline (commercially available) | 409.1 |
| 74 | 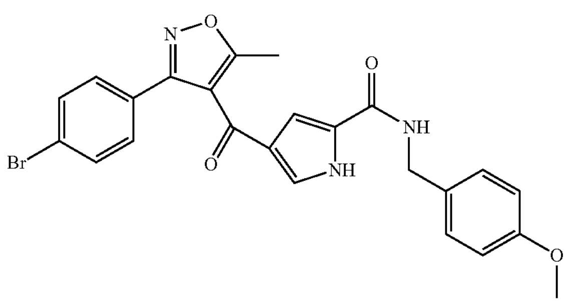 | 4-[3-(4-Bromo-phenyl)-5-methyl-isoxazole-4-carboxylic acid 4-methoxy-benzylamide | 4-[3-(4-Bromo-phenyl)-5-methyl-isoxazole-4-carbonyl]-1H-pyrrole-2-carboxylic acid (intermediate 2) and 4-methoxy-benzyl-amine (commercially available) | 492.1 |

TABLE 1-continued

| Example No. | Structure | Name | Starting materials | MW found [MH+] |
|---|---|---|---|---|
| 75 | 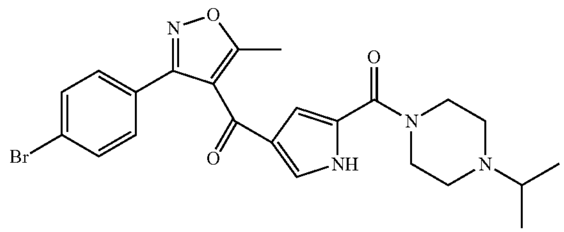 | [3-(4-Bromo-phenyl)-5-methyl-isoxazol-4-yl]-[5-(4-isopropyl-piperazine-1-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and iso-propyl piperazine (commercially available) | 483.3 |
| 76 | 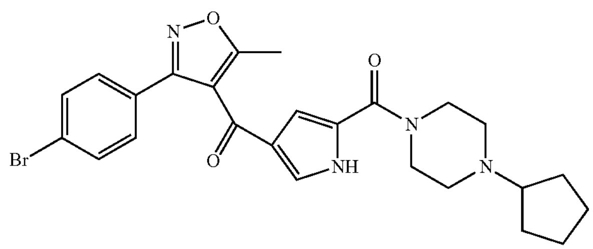 | [3-(4-Bromo-phenyl)-5-methyl-isoxazol-4-yl]-[5-(4-cyclopentyl-piperazine-1-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and cyclopentyl-piperazine (commercially available) | 509.2 |
| 77 | 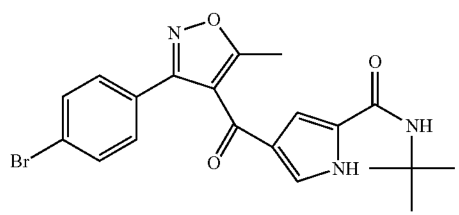 | 4-[3-(4-Bromo-phenyl)-5-methyl-isoxazole-4-carbonyl]-1H-pyrrole-2-carboxylic acid tert-butylamide | 4-[3-(4-Bromo-phenyl)-5-methyl-isoxazole-4-carbonyl]-1H-pyrrole-2-carboxylic acid (intermediate 2) and tert-butylamine (commercially available) | 428.2 |
| 78 | 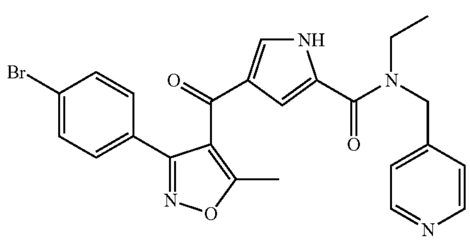 | 4-[3-(4-Bromo-phenyl)-5-methyl-isoxazole-4-carbonyl]-1H-pyrrole-2-carboxylic acid ethyl-pyridin-4-ylmethyl-amide | 4-[3-(4-Bromo-phenyl)-5-methyl-isoxazole-4-carbonyl]-1H-pyrrole-2-carboxylic acid (intermediate 2) and ethyl-pyridin-4-ylmethyl-amine (commercially available) | 491.1 |

TABLE 1-continued

| Example No. | Structure | Name | Starting materials | MW found [MH+] |
|---|---|---|---|---|
| 79 | 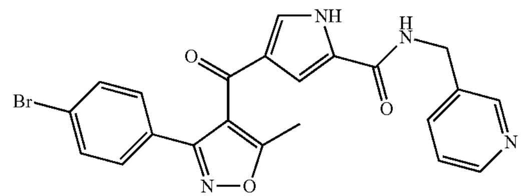 | 4-[3-(4-Bromo-phenyl)-5-methyl-isoxazole-4-carbonyl]-1H-pyrrole-2-carboxylic acid (pyridin-3-ylmethyl)-amide | 4-[3-(4-Bromo-phenyl)-5-methyl-isoxazole-4-carbonyl]-1H-pyrrole-2-carboxylic acid (intermediate 2) and pyridin-3-ylmethyl-amine (commercially available) | 463 |
| 80 | 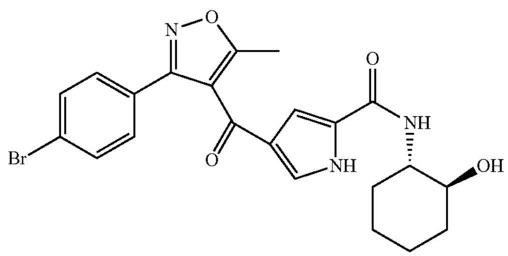 | 4-[3-(4-Bromo-phenyl)-5-methyl-isoxazole-4-carbonyl]-1H-pyrrole-2-carboxylic acid ((trans)-2-hydroxy-cyclohexyl)-amide | 4-[3-(4-Bromo-phenyl)-5-methyl-isoxazole-4-carbonyl]-1H-pyrrole-2-carboxylic acid (intermediate 2) and trans-2-hydroxy-cyclohexyl-amine (commercially available) | 470 |
| 81 | 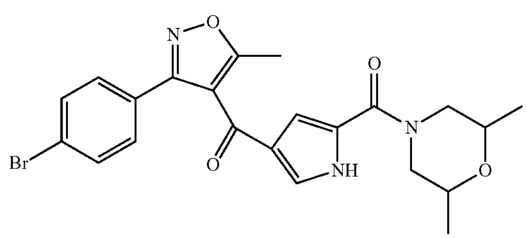 | [3-(4-Bromo-phenyl)-5-methyl-isoxazol-4-yl]-[5-(2,6-dimethyl-morpholine-4-carbonyl)-1H-pyrrol-3-yl]-methanone | 4-[3-(4-Bromo-phenyl)-5-methyl-isoxazole-4-carbonyl]-1H-pyrrole-2-carboxylic acid (intermediate 2) and 2,6-dimethyl-morpholine (commercially available) | 472.1 |
| 82 | 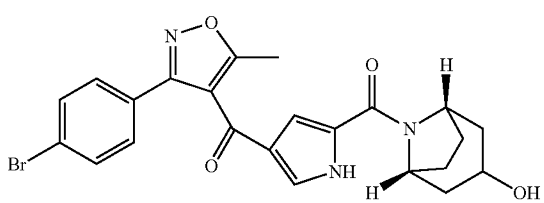 | {4-[3-(4-Bromo-phenyl)-5-methyl-isoxazole-4-carbonyl]-1H-pyrrol-2-yl}-((1S,5R)-3-hydroxy-8-aza-bicyclo[3.2.1]oct-8-yl)-methanone | 4-[3-(4-Bromo-phenyl)-5-methyl-isoxazole-4-carbonyl]-1H-pyrrole-2-carboxylic acid (intermediate 2) and (1S,5R)-3-hydroxy-8-aza-bicyclo[3.2.1]octane (commercially available) | 484.2 |

TABLE 1-continued

| Example No. | Name | Structure | Starting materials | MW found [MH+] |
|---|---|---|---|---|
| 83 | 4-[3-(4-Bromo-phenyl)-5-methyl-isoxazole-4-carbonyl]-1H-pyrrole-2-carboxylic acid (3-morpholin-4-yl-propyl)-amide | 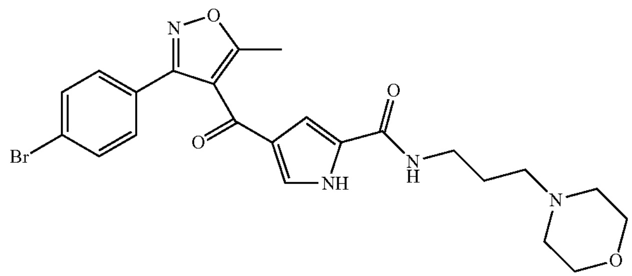 | 4-[3-(4-Bromo-phenyl)-5-methyl-isoxazole-4-carbonyl]-1H-pyrrole-2-carboxylic acid (intermediate 2) and 3-morpholin-4-yl-propyl-amine commercially available | 501.0/503.0 |
| 84 | 4-[3-(4-Bromo-phenyl)-5-methyl-isoxazole-4-carbonyl]-1H-pyrrole-2-carboxylic acid isopropylamide | 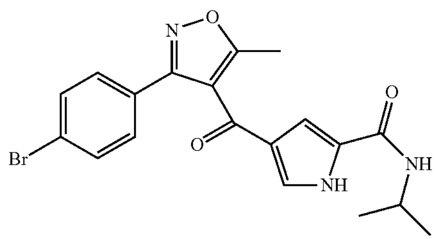 | 4-[3-(4-Bromo-phenyl)-5-methyl-isoxazole-4-carbonyl]-1H-pyrrole-2-carboxylic acid (intermediate 2) and isopropylamine (commercially available) | 416.2 |
| 85 | 4-[3-(4-Bromo-phenyl)-5-methyl-isoxazole-4-carbonyl]-1H-pyrrole-2-carboxylic acid cyclopropylmethyl-amide | 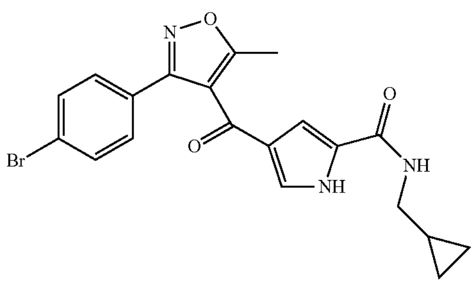 | 4-[3-(4-Bromo-phenyl)-5-methyl-isoxazole-4-carbonyl]-1H-pyrrole-2-carboxylic acid (intermediate 2) and cyclopropylmethyl-amine (commercially available) | 430.2 |

TABLE 1-continued

| Example No. | Structure | Name | Starting materials | MW found [MH+] |
|---|---|---|---|---|
| 86 | (structure) | 4-[3-(4-Bromo-phenyl)-5-methyl-isoxazole-4-carbonyl]-1H-pyrrole-2-carboxylic acid ((R)-sec-butyl)-amide | 4-[3-(4-Bromo-phenyl)-5-methyl-isoxazole-4-carbonyl]-1H-pyrrole-2-carboxylic acid (intermediate 2) and (R)-sec-butyl-amine (commercially available) | 432.3 |
| 87 | (structure) | 4-[3-(4-Bromo-phenyl)-5-methyl-isoxazole-4-carbonyl]-1H-pyrrole-2-carboxylic acid butylamide | 4-[3-(4-Bromo-phenyl)-5-methyl-isoxazole-4-carbonyl]-1H-pyrrole-2-carboxylic acid (intermediate 2) and butylamine (commercially available) | 430.3 |
| 88 | (structure) | 4-[3-(4-Bromo-phenyl)-5-methyl-isoxazole-4-carbonyl]-1H-pyrrole-2-carboxylic acid isobutyl-amide | 4-[3-(4-Bromo-phenyl)-5-methyl-isoxazole-4-carbonyl]-1H-pyrrole-2-carboxylic acid (intermediate 2) and isobutylamine (commercially available) | 432.3 |

TABLE 1-continued

| Example No. | Structure | Name | Starting materials | MW found [MH+] |
|---|---|---|---|---|
| 89 | 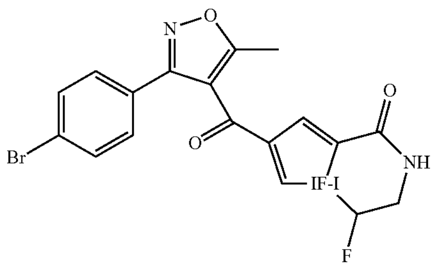 | 4-[3-(4-Bromo-phenyl)-5-methyl-isoxazole-4-carbonyl]-1H-pyrrole-2-carboxylic acid (2,2-difluoro-ethyl)-amide | 4-[3-(4-Bromo-phenyl)-5-methyl-isoxazole-4-carbonyl]-1H-pyrrole-2-carboxylic acid (intermediate 2) and 2,2-difluoro-ethyl-amine (commercially available) | 440.1 |
| 90 | 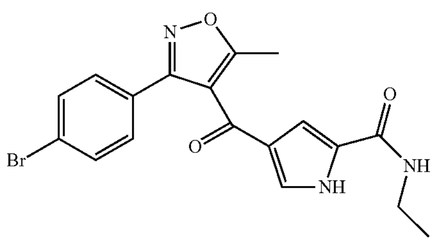 | 4-[3-(4-Bromo-phenyl)-5-methyl-isoxazole-4-carbonyl]-1H-pyrrole-2-carboxylic acid ethylamide | 4-[3-(4-Bromo-phenyl)-5-methyl-isoxazole-4-carbonyl]-1H-pyrrole-2-carboxylic acid (intermediate 2) and ethylamine (commercially available) | 402.2 |
| 91 | 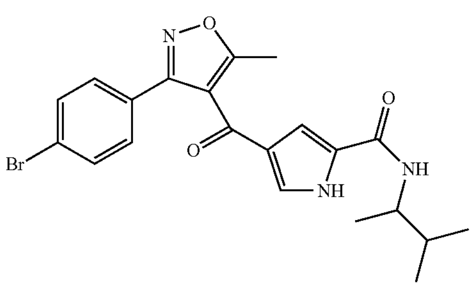 | 4-[3-(4-Bromo-phenyl)-5-methyl-isoxazole-4-carbonyl]-1H-pyrrole-2-carboxylic acid (1,2-dimethyl-propyl)-amide | 4-[3-(4-Bromo-phenyl)-5-methyl-isoxazole-4-carbonyl]-1H-pyrrole-2-carboxylic acid (intermediate 2) and 1,2-dimethyl-propyl-amine (commercially available) | 444.2 |

TABLE 1-continued

| Example No. | Structure | Name | Starting materials | MW found [MH⁺] |
|---|---|---|---|---|
| 92 | 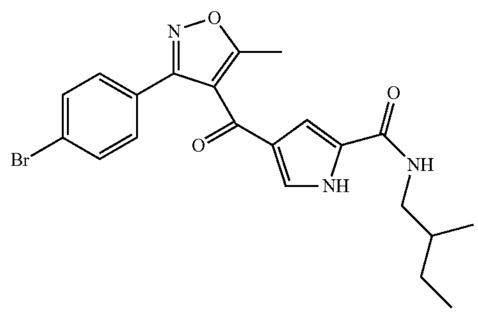 | 4-[3-(4-Bromo-phenyl)-5-methyl-isoxazole-4-carbonyl]-1H-pyrrole-2-carboxylic acid (2-methyl-butyl)-amide | 4-[3-(4-Bromo-phenyl)-5-methyl-isoxazole-4-carbonyl]-1H-pyrrole-2-carboxylic acid (intermediate 2) and 2-methyl-butyl-amine (commercially available) | 444.2 |
| 93 | 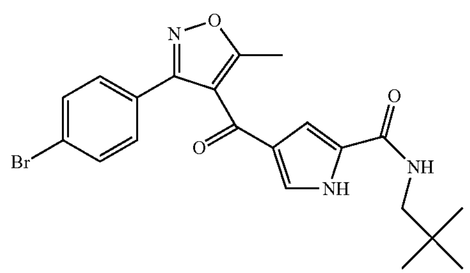 | 4-[3-(4-Bromo-phenyl)-5-methyl-isoxazole-4-carbonyl]-1H-pyrrole-2-carboxylic acid (2,2-dimethyl-propyl)-amide | 4-[3-(4-Bromo-phenyl)-5-methyl-isoxazole-4-carbonyl]-1H-pyrrole-2-carboxylic acid (intermediate 2) and 2,2-dimethyl-propyl-amine (commercially available) | 444.2 |
| 94 | 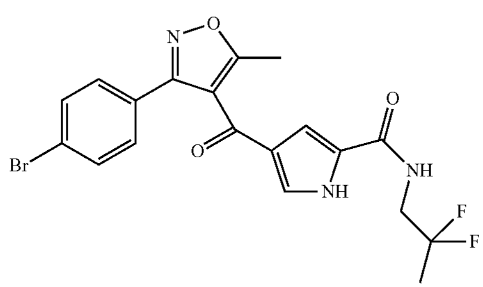 | 4-[3-(4-Bromo-phenyl)-5-methyl-isoxazole-4-carbonyl]-1H-pyrrole-2-carboxylic acid (2,2-difluoro-propyl)-amide | 4-[3-(4-Bromo-phenyl)-5-methyl-isoxazole-4-carbonyl]-1H-pyrrole-2-carboxylic acid (intermediate 2) and 2,2-difluoro-propyl-amine (commercially available) | 454.1 |

TABLE 1-continued

| Example No. | Structure | Name | Starting materials | MW found [MH+] |
|---|---|---|---|---|
| 95 | 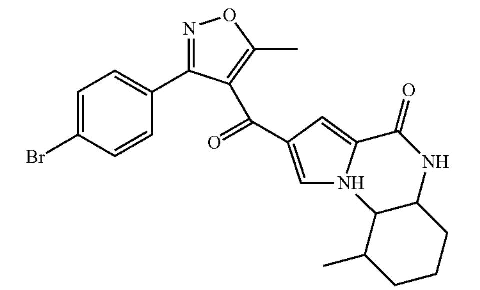 | 4-[3-(4-Bromo-phenyl)-5-methyl-isoxazole-4-carbonyl]-1H-pyrrole-2-carboxylic acid (2,3-dimethyl-cyclohexyl)-amide | 4-[3-(4-Bromo-phenyl)-5-methyl-isoxazole-4-carbonyl]-1H-pyrrole-2-carboxylic acid (intermediate 2) and 2,3-dimethyl-cyclohexyl-amine (commercially available) | 484.3 |
| 96 | 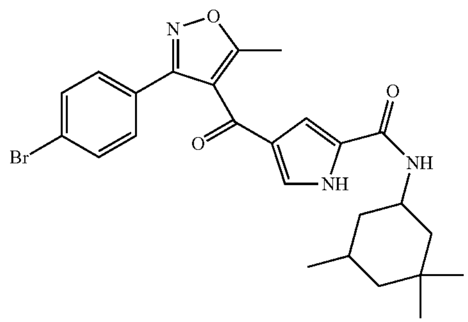 | 4-[3-(4-Bromo-phenyl)-5-methyl-isoxazole-4-carbonyl]-1H-pyrrole-2-carboxylic acid (3,3,5-trimethyl-cyclohexyl)-amide | 4-[3-(4-Bromo-phenyl)-5-methyl-isoxazole-4-carbonyl]-1H-pyrrole-2-carboxylic acid (intermediate 2) and 3,3,5-trimethyl-cyclohexyl-amine (commercially available) | 498.3 |
| 97 | 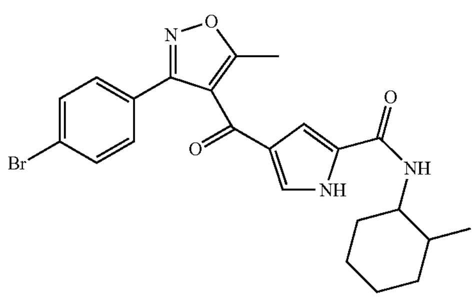 | 4-[3-(4-Bromo-phenyl)-5-methyl-isoxazole-4-carbonyl]-1H-pyrrole-2-carboxylic acid (2-methyl-cyclohexyl)-amide | 4-[3-(4-Bromo-phenyl)-5-methyl-isoxazole-4-carbonyl]-1H-pyrrole-2-carboxylic acid (intermediate 2) and 2-methyl-cyclohexyl-amine (commercially available) | 472.2 |

TABLE 1-continued

| Example No. | Structure | Name | Starting materials | MW found [MH+] |
|---|---|---|---|---|
| 98 | 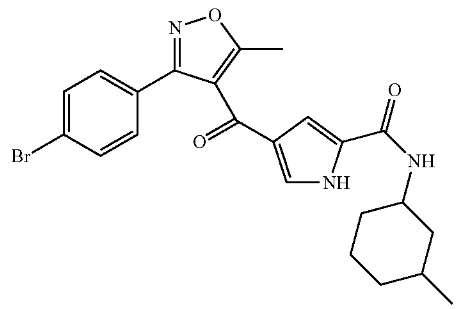 | 4-[3-(4-Bromo-phenyl)-5-methyl-isoxazole-4-carbonyl]-1H-pyrrole-2-carboxylic acid (3-methyl-cyclohexyl)-amide | 4-[3-(4-Bromo-phenyl)-5-methyl-isoxazole-4-carbonyl]-1H-pyrrole-2-carboxylic acid (intermediate 2) and 3-methyl-cyclohexyl-amine (commercially available) | 470.2 |
| 99 | 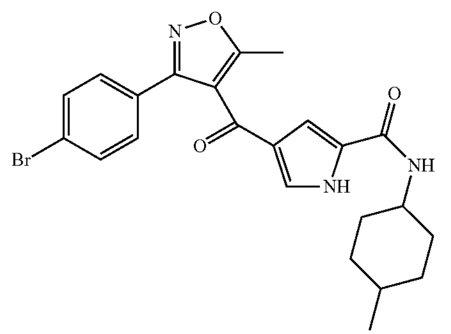 | 4-[3-(4-Bromo-phenyl)-5-methyl-isoxazole-4-carbonyl]-1H-pyrrole-2-carboxylic acid (4-methyl-cyclohexyl)-amide | 4-[3-(4-Bromo-phenyl)-5-methyl-isoxazole-4-carbonyl]-1H-pyrrole-2-carboxylic acid (intermediate 2) and 4-methyl-cyclohexyl-amine (commercially available) | 470.3 |
| 100 | 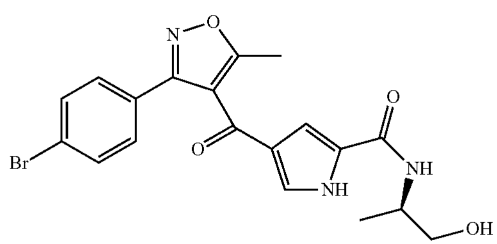 | 4-[3-(4-Bromo-phenyl)-5-methyl-isoxazole-4-carbonyl]-1H-pyrrole-2-carboxylic acid ((R)-2-hydroxy-1-methyl-ethyl)-amide | 4-[3-(4-Bromo-phenyl)-5-methyl-isoxazole-4-carbonyl]-1H-pyrrole-2-carboxylic acid (intermediate 2) and (R)-2-hydroxy-1-methyl-ethyl-amine (commercially available) | 432.2 |

TABLE 1-continued

| Example No. | Structure | Name | Starting materials | MW found [MH+] |
|---|---|---|---|---|
| 101 | 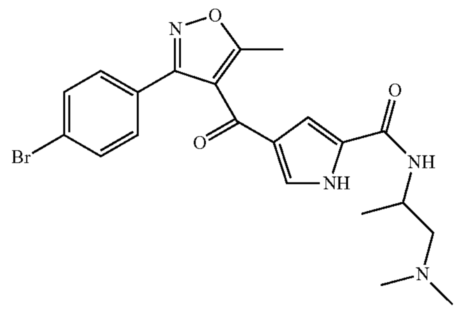 | 4-[3-(4-Bromo-phenyl)-5-methyl-isoxazole-4-carbonyl]-1H-pyrrole-2-carboxylic acid (2-dimethylamino-1-methyl-ethyl)-amide | 4-[3-(4-Bromo-phenyl)-5-methyl-isoxazole-4-carbonyl]-1H-pyrrole-2-carboxylic acid (intermediate 2) and 2-dimethylamino-1-methyl-ethyl-amine (commercially available) | 459.2 |
| 102 | 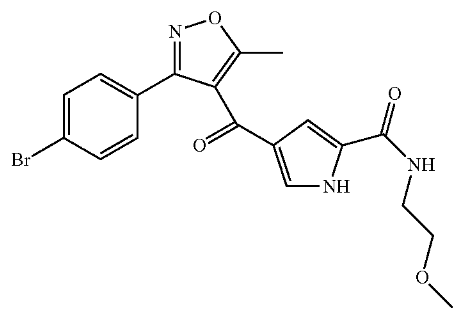 | 4-[3-(4-Bromo-phenyl)-5-methyl-isoxazole-4-carbonyl]-1H-pyrrole-2-carboxylic acid (2-methoxy-ethyl)-amide | 4-[3-(4-Bromo-phenyl)-5-methyl-isoxazole-4-carbonyl]-1H-pyrrole-2-carboxylic acid (intermediate 2) and 2-methoxy-ethyl-amine (commercially available) | 432.2 |
| 103 | 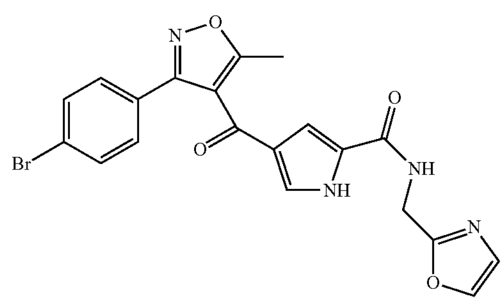 | 4-[3-(4-Bromo-phenyl)-5-methyl-isoxazole-4-carbonyl]-1H-pyrrole-2-carboxylic acid (oxazol-2-ylmethyl)-amide | 4-[3-(4-Bromo-phenyl)-5-methyl-isoxazole-4-carbonyl]-1H-pyrrole-2-carboxylic acid (intermediate 2) and oxazol-2-ylmethyl-amine (commercially available) | 455.1 |

TABLE 1-continued

| Example No. | Structure | Name | Starting materials | MW found [MH+] |
|---|---|---|---|---|
| 104 | 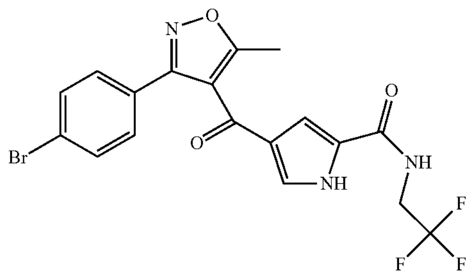 | 4-[3-(4-Bromo-phenyl)-5-methyl-isoxazole-4-carbonyl]-1H-pyrrole-2-carboxylic acid (2,2,2-trifluoro-ethyl)-amide | 4-[3-(4-Bromo-phenyl)-5-methyl-isoxazole-4-carbonyl]-1H-pyrrole-2-carboxylic acid (intermediate 2) and 2,2,2-trifluoro-ethyl-amine (commercially available) | 456.1 |
| 105 | 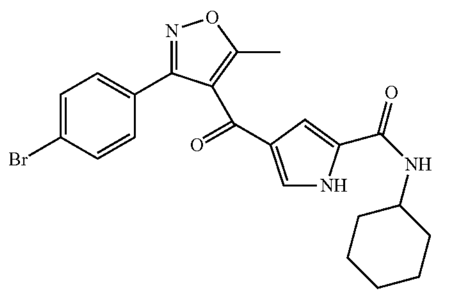 | 4-[3-(4-Bromo-phenyl)-5-methyl-isoxazole-4-carbonyl]-1H-pyrrole-2-carboxylic acid cyclohexylamide | 4-[3-(4-Bromo-phenyl)-5-methyl-isoxazole-4-carbonyl]-1H-pyrrole-2-carboxylic acid (intermediate 2) and cyclohexylamine (commercially available) | 456.2 |
| 106 | 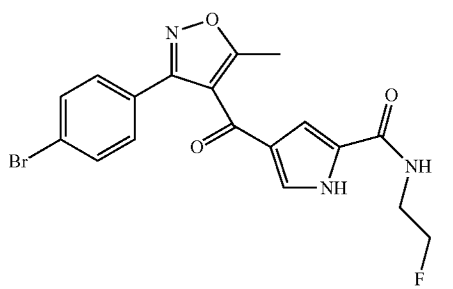 | 4-[3-(4-Bromo-phenyl)-5-methyl-isoxazole-4-carbonyl]-1H-pyrrole-2-carboxylic acid (2-fluoro-ethyl)-amide | 4-[3-(4-Bromo-phenyl)-5-methyl-isoxazole-4-carbonyl]-1H-pyrrole-2-carboxylic acid (intermediate 2) and 2-fluoro-ethyl-amine (commercially available) | 422.1 |

TABLE 1-continued

| Example No. | Structure | Name | Starting materials | MW found [MH+] |
|---|---|---|---|---|
| 107 | 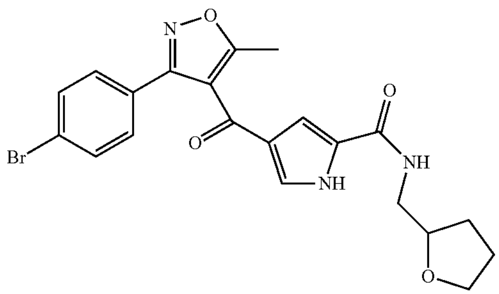 | 4-[3-(4-Bromo-phenyl)-5-methyl-isoxazole-4-carbonyl]-1H-pyrrole-2-carboxylic acid (tetrahydro-furan-2-ylmethyl)-amide | 4-[3-(4-Bromo-phenyl)-5-methyl-isoxazole-4-carbonyl]-1H-pyrrole-2-carboxylic acid (intermediate 2) and tetrahydro-furan-2-ylmethyl-amine (commercially available) | 458.2 |
| 108 | 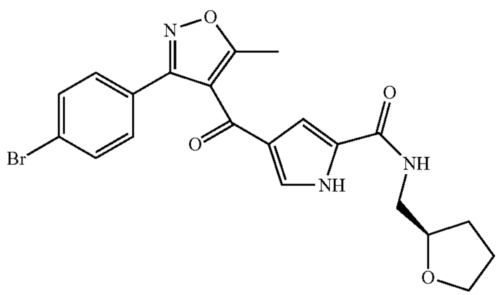 | 4-[3-(4-Bromo-phenyl)-5-methyl-isoxazole-4-carbonyl]-1H-pyrrole-2-carboxylic acid [(R)-1-(tetrahydro-furan-2-yl)methyl]-amide | 4-[3-(4-Bromo-phenyl)-5-methyl-isoxazole-4-carbonyl]-1H-pyrrole-2-carboxylic acid (intermediate 2) and (R)-1-(tetrahydro-furan-2-yl)methyl-amine (commercially available) | 458.2 |
| 109 | 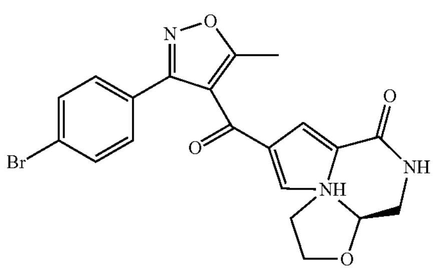 | 4-[3-(4-Bromo-phenyl)-5-methyl-isoxazole-4-carbonyl]-1H-pyrrole-2-carboxylic acid [(S)-1-(tetrahydro-furan-2-yl)methyl]-amide | 4-[3-(4-Bromo-phenyl)-5-methyl-isoxazole-4-carbonyl]-1H-pyrrole-2-carboxylic acid (intermediate 2) and (S)-1-(tetrahydro-furan-2-yl)methyl-amine (commercially available) | 458.2 |

TABLE 1-continued

| Example No. | Structure | Name | Starting materials | MW found [MH+] |
|---|---|---|---|---|
| 110 | 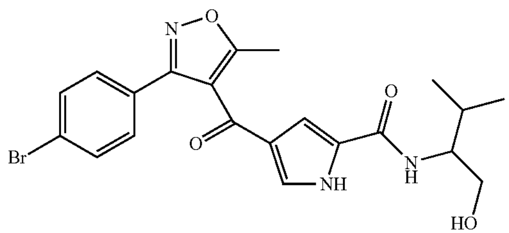 | 4-[3-(4-Bromo-phenyl)-5-methyl-isoxazole-4-carbonyl]-1H-pyrrole-2-carboxylic acid (1-hydroxymethyl-2-methyl-propyl)-amide | 4-[3-(4-Bromo-phenyl)-5-methyl-isoxazole-4-carbonyl]-1H-pyrrole-2-carboxylic acid (intermediate 2) and 1-hydroxymethyl-2-methyl-propyl-amine (commercially available) | 462.2 |
| 111 | 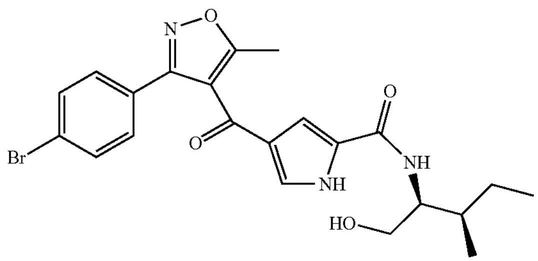 | 4-[3-(4-Bromo-phenyl)-5-methyl-isoxazole-4-carbonyl]-1H-pyrrole-2-carboxylic acid ((1S,2S)-1-hydroxymethyl-2-methyl-butyl)-amide | 4-[3-(4-Bromo-phenyl)-5-methyl-isoxazole-4-carbonyl]-1H-pyrrole-2-carboxylic acid (intermediate 2) and (1S,2S)-1-hydroxymethyl-2-methyl-butyl-amine (commercially available) | 474.1 |
| 112 | 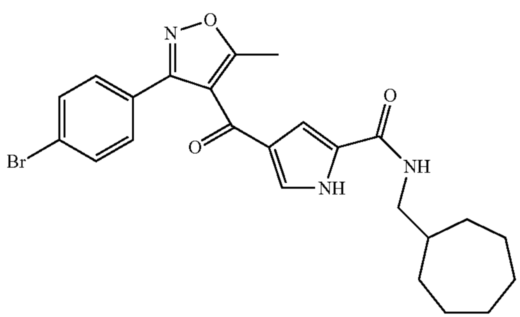 | 4-[3-(4-Bromo-phenyl)-5-methyl-isoxazole-4-carbonyl]-1H-pyrrole-2-carboxylic acid cycloheptylmethyl-amide | 4-[3-(4-Bromo-phenyl)-5-methyl-isoxazole-4-carbonyl]-1H-pyrrole-2-carboxylic acid (intermediate 2) and cycloheptylmethyl-amine (commercially available) | 484.3 |

TABLE 1-continued

| Example No. | Structure | Name | Starting materials | MW found [MH+] |
|---|---|---|---|---|
| 113 | 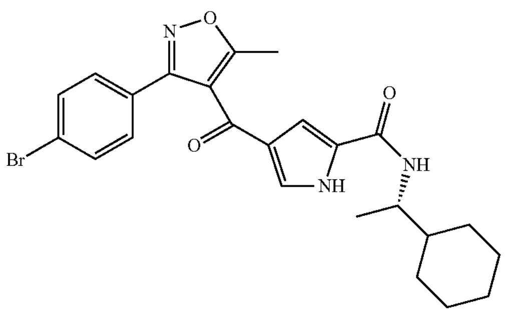 | 4-[3-(4-Bromo-phenyl)-5-methyl-isoxazole-4-carbonyl]-1H-pyrrole-2-carboxylic acid ((S)-1-cyclohexyl-ethyl)-amide | 4-[3-(4-Bromo-phenyl)-5-methyl-isoxazole-4-carbonyl]-1H-pyrrole-2-carboxylic acid (intermediate 2) and (S)-1-cyclohexyl-ethyl-amine (commercially available) | 484.2 |
| 114 | 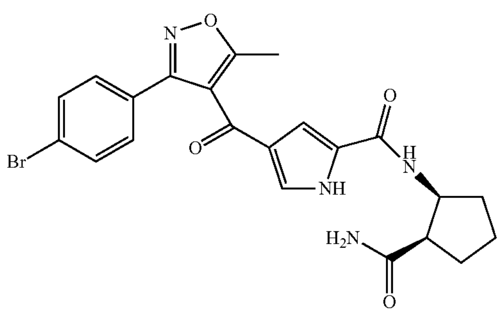 | 4-[3-(4-Bromo-phenyl)-5-methyl-isoxazole-4-carbonyl]-1H-pyrrole-2-carboxylic acid ((1S,2R)-2-carbamoyl-cyclopentyl)-amide | 4-[3-(4-Bromo-phenyl)-5-methyl-isoxazole-4-carbonyl]-1H-pyrrole-2-carboxylic acid (intermediate 2) and (1S,2R)-2-carba-moyl-cyclopentyl-amine (commercially available) | 485.2 |
| 115 | 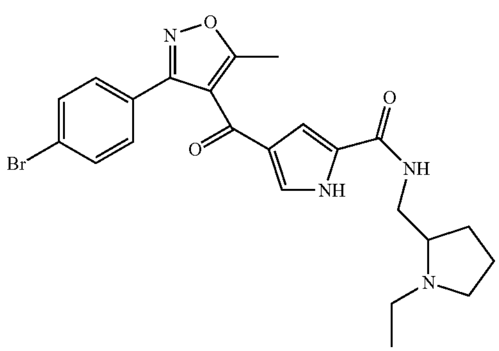 | 4-[3-(4-Bromo-phenyl)-5-methyl-isoxazole-4-carbonyl]-1H-pyrrole-2-carboxylic acid (1-ethyl-pyrrolidin-2-ylmethyl)-amide | 4-[3-(4-Bromo-phenyl)-5-methyl-isoxazole-4-carbonyl]-1H-pyrrole-2-carboxylic acid (intermediate 2) and 1-ethyl-pyrrolidin-2-ylmethyl-amine (commercially available) | 485.2 |

TABLE 1-continued

| Example No. | Structure | Name | Starting materials | MW found [MH+] |
|---|---|---|---|---|
| 116 | 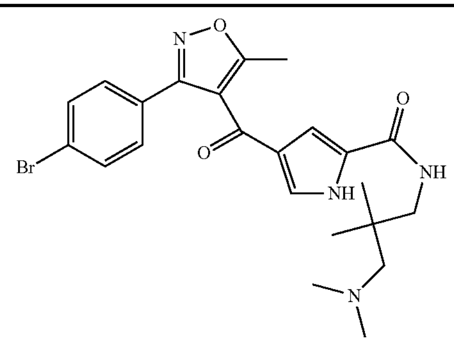 | 4-[3-(4-Bromo-phenyl)-5-methyl-isoxazole-4-carbonyl]-1H-pyrrole-2-carboxylic acid (3-dimethylamino-2,2-dimethyl-propyl)-amide | 4-[3-(4-Bromo-phenyl)-5-methyl-isoxazole-4-carbonyl]-1H-pyrrole-2-carboxylic acid (intermediate 2) and 3-dimethylamino-2,2-dimethyl-propyl-amine (commercially available) | 487.2 |
| 117 | 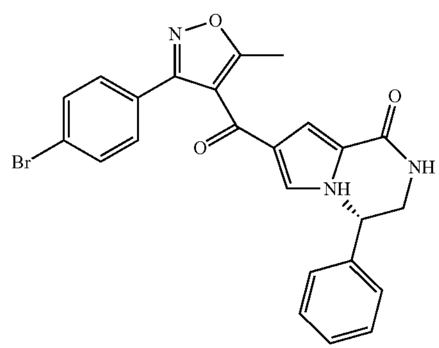 | 4-[3-(4-Bromo-phenyl)-5-methyl-isoxazole-4-carbonyl]-1H-pyrrole-2-carboxylic acid ((S)-2-phenyl-propyl)-amide | 4-[3-(4-Bromo-phenyl)-5-methyl-isoxazole-4-carboxylic acid (intermediate 2) and (S)-2-phenyl-propyl-amine (commercially available) | 494.2 |
| 118 | 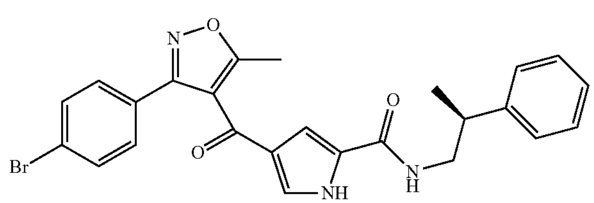 | 4-[3-(4-Bromo-phenyl)-5-methyl-isoxazole-4-carbonyl]-1H-pyrrole-2-carboxylic acid ((R)-2-phenyl-propyl)-amide | 4-[3-(4-Bromo-phenyl)-5-methyl-isoxazole-4-carboxylic acid (intermediate 2) and (R)-2-phenyl-propyl-amine (commercially available) | 494.2 |

TABLE 1-continued

| Example No. | Structure | Name | Starting materials | MW found [MH+] |
|---|---|---|---|---|
| 119 | 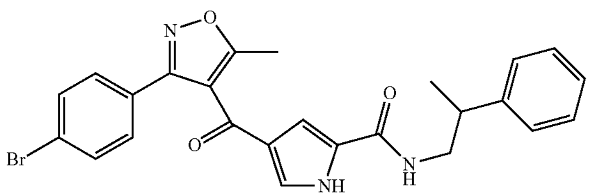 | 4-[3-(4-Bromo-phenyl)-5-methyl-isoxazole-4-carbonyl]-1H-pyrrole-2-carboxylic acid (2-phenyl-propyl)-amide | 4-[3-(4-Bromo-phenyl)-5-methyl-isoxazole-4-carbonyl]-1H-pyrrole-2-carboxylic acid (intermediate 2) and (2-phenyl-propyl)-amine (commercially available) | 494.2 |
| 120 | 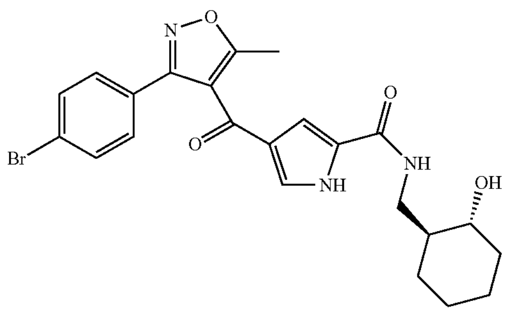 | 4-[3-(4-Bromo-phenyl)-5-methyl-isoxazole-4-carbonyl]-1H-pyrrole-2-carboxylic acid ((1S,2R)-2-hydroxy-cyclohexylmethyl)-amide | 4-[3-(4-Bromo-phenyl)-5-methyl-isoxazole-4-carbonyl]-1H-pyrrole-2-carboxylic acid (intermediate 2) and (1S,2R)-2-hydroxy-cyclohexylmethyl-amine (commercially available) | 488.3 |
| 121 | 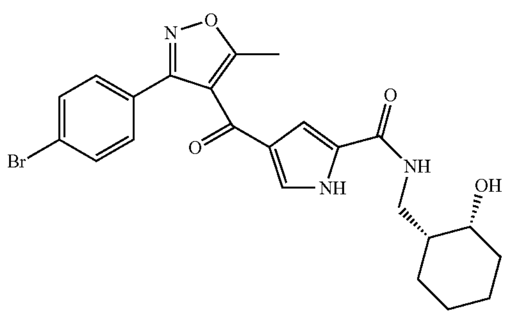 | 4-[3-(4-Bromo-phenyl)-5-methyl-isoxazole-4-carbonyl]-1H-pyrrole-2-carboxylic acid ((1R,2R)-2-hydroxy-cyclohexylmethyl)-amide | 4-[3-(4-Bromo-phenyl)-5-methyl-isoxazole-4-carbonyl]-1H-pyrrole-2-carboxylic acid (intermediate 2) and (1R,2R)-2-hydroxy-cyclohexylmethyl-amine (commercially available) | 488.3 |

TABLE 1-continued

| Example No. | Structure | Name | Starting materials | MW found [MH+] |
|---|---|---|---|---|
| 122 | 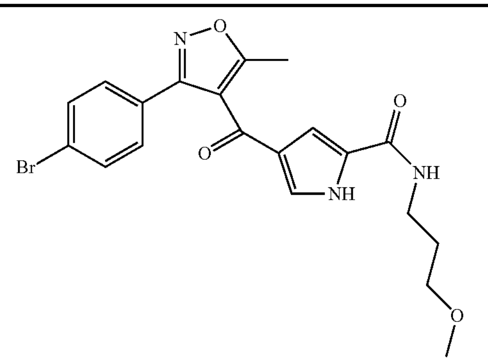 | 4-[3-(4-Bromo-phenyl)-5-methyl-isoxazole-4-carbonyl]-1H-pyrrole-2-carboxylic acid (3-methoxy-propyl)-amide | 4-[3-(4-Bromo-phenyl)-5-methyl-isoxazole-4-carbonyl]-1H-pyrrole-2-carboxylic acid (intermediate 2) and 3-methoxy-propyl-amine (commercially available) | 446.2 |
| 123 | 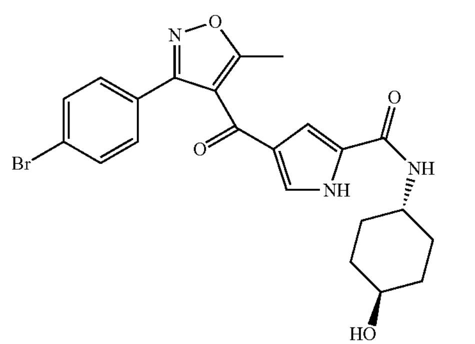 | 4-[3-(4-Bromo-phenyl)-5-methyl-isoxazole-4-carbonyl]-1H-pyrrole-2-carboxylic acid (4-hydroxy-cyclohexyl)-amide | 4-[3-(4-Bromo-phenyl)-5-methyl-isoxazole-4-carbonyl]-1H-pyrrole-2-carboxylic acid (intermediate 2) and 4-hydroxy-cyclohexyl-amine (commercially available) | 472.2 |
| 124 | 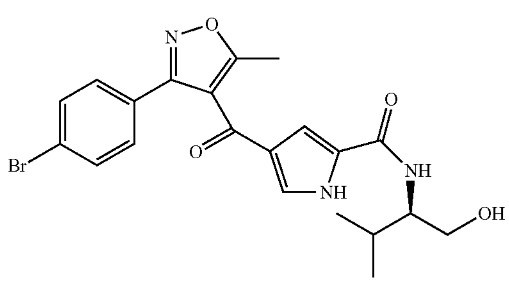 | 4-[3-(4-Bromo-phenyl)-5-methyl-isoxazole-4-carbonyl]-1H-pyrrole-2-carboxylic acid ((R)-1-hydroxymethyl-2-methyl-propyl)-amide | 4-[3-(4-Bromo-phenyl)-5-methyl-isoxazole-4-carbonyl]-1H-pyrrole-2-carboxylic acid (intermediate 2) and (R)-1-hydroxymethyl-2-methyl-propyl-amine (commercially available) | 462.2 |

TABLE 1-continued

| Example No. | Structure | Name | Starting materials | MW found [MH⁺] |
|---|---|---|---|---|
| 125 | 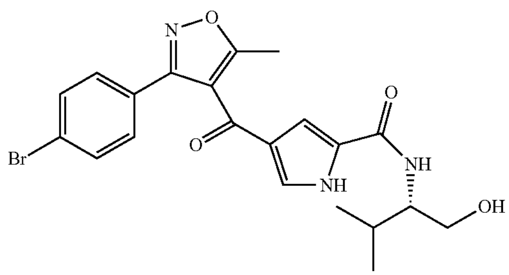 | 4-[3-(4-Bromo-phenyl)-5-methyl-isoxazole-4-carbonyl]-1H-pyrrole-2-carboxylic acid ((S)-1-hydroxymethyl-2-methyl-propyl)-amide | 4-[3-(4-Bromo-phenyl)-5-methyl-isoxazole-4-carbonyl]-1H-pyrrole-2-carboxylic acid (intermediate 2) and (S)-1-hydroxymethyl-2-methyl-propyl-amine (commercially available) | 462.2 |
| 126 | 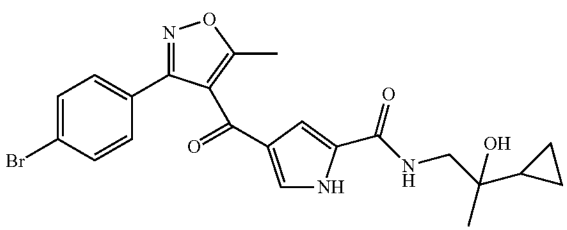 | 4-[3-(4-Bromo-phenyl)-5-methyl-isoxazole-4-carbonyl]-1H-pyrrole-2-carboxylic acid (2-cyclopropyl-2-hydroxy-propyl)-amide | 4-[3-(4-Bromo-phenyl)-5-methyl-isoxazole-4-carbonyl]-1H-pyrrole-2-carboxylic acid (intermediate 2) and 2-cyclopropyl-2-hydroxy-propyl-amine (commercially available) | 470.2/472.0 |
| 127 | 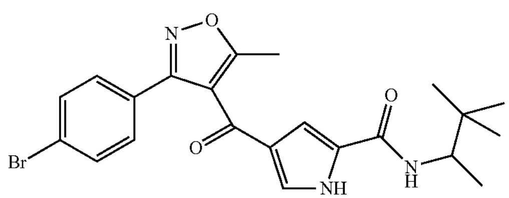 | 4-[3-(4-Bromo-phenyl)-5-methyl-isoxazole-4-carbonyl]-1H-pyrrole-2-carboxylic acid (1,2,2-trimethyl-propyl)-amide | 4-[3-(4-Bromo-phenyl)-5-methyl-isoxazole-4-carbonyl]-1H-pyrrole-2-carboxylic acid (intermediate 2) and 1,2,2-trimethyl-propyl-amine (commercially available) | 455.9/458.0 |
| 128 | 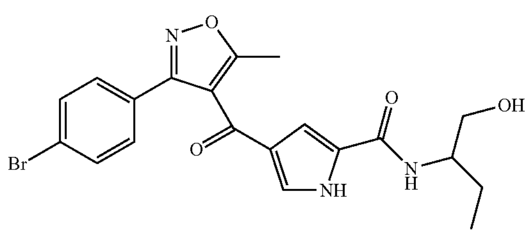 | 4-[3-(4-Bromo-phenyl)-5-methyl-isoxazole-4-carbonyl]-1H-pyrrole-2-carboxylic acid (1-hydroxymethyl-propyl)-amide | 4-[3-(4-Bromo-phenyl)-5-methyl-isoxazole-4-carbonyl]-1H-pyrrole-2-carboxylic acid (intermediate 2) and 1-hydroxymethyl-propyl-amine (commercially available) | 444.2/446.1 |

TABLE 1-continued

| Example No. | Structure | Name | Starting materials | MW found [MH+] |
|---|---|---|---|---|
| 129 | 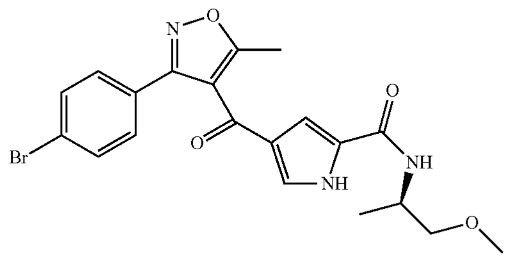 | 4-[3-(4-Bromo-phenyl)-5-methyl-isoxazole-4-carbonyl]-1H-pyrrole-2-carboxylic acid ((R)-2-methoxy-1-methyl-ethyl)-amide | 4-[3-(4-Bromo-phenyl)-5-methyl-isoxazole-4-carbonyl]-1H-pyrrole-2-carboxylic acid (intermediate 2) and (R)-2-methoxy-1-methyl-ethyl-amine (commercially available) | 444.2/446.0 |
| 130 | 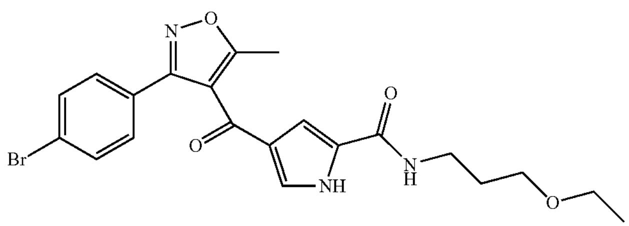 | 4-[3-(4-Bromo-phenyl)-5-methyl-isoxazole-4-carbonyl]-1H-pyrrole-2-carboxylic acid (3-ethoxy-propyl)-amide | 4-[3-(4-Bromo-phenyl)-5-methyl-isoxazole-4-carbonyl]-1H-pyrrole-2-carboxylic acid (intermediate 2) and 3-ethoxy-propyl-amine (commercially available) | 460.1/458.2 |
| 131 | 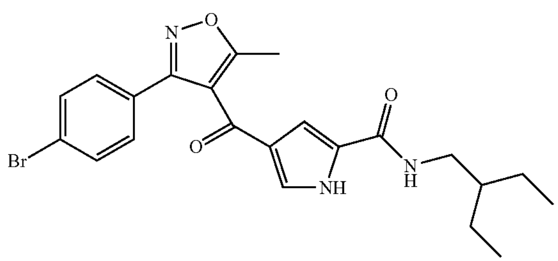 | 4-[3-(4-Bromo-phenyl)-5-methyl-isoxazole-4-carbonyl]-1H-pyrrole-2-carboxylic acid (2-ethyl-butyl)-amide | 4-[3-(4-Bromo-phenyl)-5-methyl-isoxazole-4-carbonyl]-1H-pyrrole-2-carboxylic acid (intermediate 2) and 2-ethyl-butyl-amine (commercially available) | 456.2/458.2 |
| 132 | 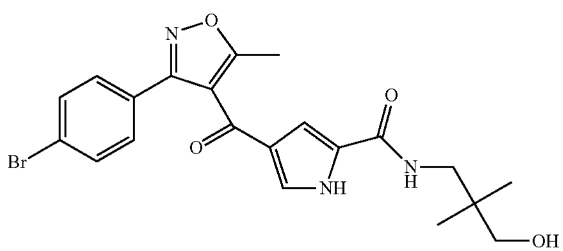 | 4-[3-(4-Bromo-phenyl)-5-methyl-isoxazole-4-carbonyl]-1H-pyrrole-2-carboxylic acid (3-hydroxy-2,2-dimethyl-propyl)-amide | 4-[3-(4-Bromo-phenyl)-5-methyl-isoxazole-4-carbonyl]-1H-pyrrole-2-carboxylic acid (intermediate 2) and 3-hydroxy-2,2-dimethyl-propyl-amine (commercially available) | 458.2/460.1 |

TABLE 1-continued

| Example No. | Structure | Name | Starting materials | MW found [MH+] |
|---|---|---|---|---|
| 133 | 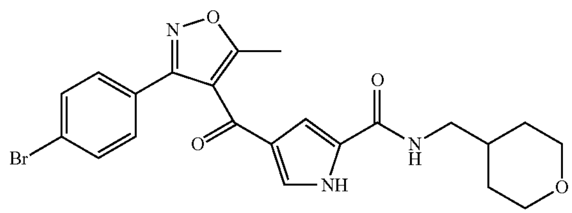 | 4-[3-(4-Bromo-phenyl)-5-methyl-isoxazole-4-carbonyl]-1H-pyrrole-2-carboxylic acid (tetrahydro-pyran-4-ylmethyl)-amide | 4-[3-(4-Bromo-phenyl)-5-methyl-isoxazole-4-carbonyl]-1H-pyrrole-2-carboxylic acid (intermediate 2) and tetrahydro-pyran-4-ylmethyl-amine (commercially available) | 470.2/472.0 |
| 134 | 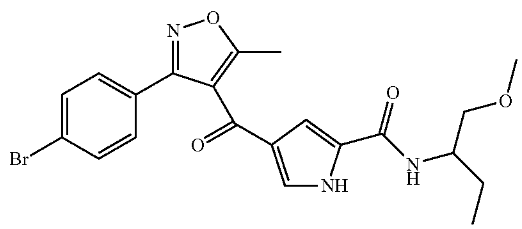 | 4-[3-(4-Bromo-phenyl)-5-methyl-isoxazole-4-carbonyl]-1H-pyrrole-2-carboxylic acid (1-methoxymethyl-propyl)-amide | 4-[3-(4-Bromo-phenyl)-5-methyl-isoxazole-4-carbonyl]-1H-pyrrole-2-carboxylic acid (intermediate 2) and 1-methoxymethyl-propyl-amine (commercially available) | 458.2/460.1 |
| 135 | 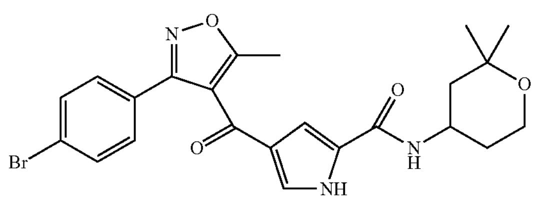 | 4-[3-(4-Bromo-phenyl)-5-methyl-isoxazole-4-carbonyl]-1H-pyrrole-2-carboxylic acid (2,2-dimethyl-tetrahydro-pyran-4-yl)-amide | 4-[3-(4-Bromo-phenyl)-5-methyl-isoxazole-4-carbonyl]-1H-pyrrole-2-carboxylic acid (intermediate 2) and 2,2-dimethyl-tetrahydro-pyran-4-yl-amine (commercially available) | 484.2/486.2 |
| 136 | 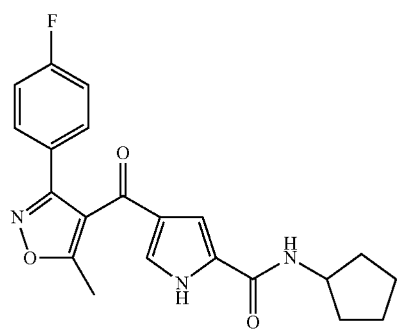 | 4-[3-(4-Fluoro-phenyl)-5-methyl-isoxazole-4-carbonyl]-1H-pyrrole-2-carboxylic acid cyclopentylamide | 4-[3-(4-Fluoro-phenyl)-5-methyl-isoxazole-4-carbonyl]-1H-pyrrole-2-carboxylic acid (intermediate 3) and cyclopentyl-amine (commercially available) | 382.2 |

TABLE 1-continued

| Example No. | Structure | Name | Starting materials | MW found [MH+] |
|---|---|---|---|---|
| 137 | 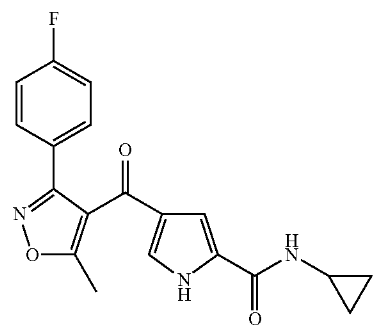 | 4-[3-(4-Fluoro-phenyl)-5-methyl-isoxazole-4-carbonyl]-1H-pyrrole-2-carboxylic acid cyclopropylamide | 4-[3-(4-Fluoro-phenyl)-5-methyl-isoxazole-4-carbonyl]-1H-pyrrole-2-carboxylic acid (intermediate 3) and cyclopropyl-amine (commercially available) | 354.2 |
| 138 | 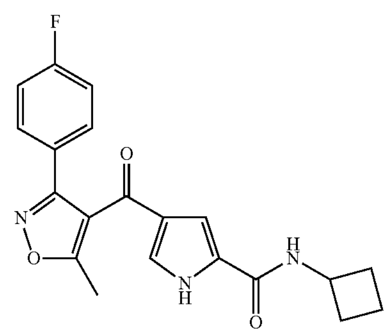 | 4-[3-(4-Fluoro-phenyl)-5-methyl-isoxazole-4-carbonyl]-1H-pyrrole-2-carboxylic acid cyclobutylamide | 4-[3-(4-Fluoro-phenyl)-5-methyl-isoxazole-4-carbonyl]-1H-pyrrole-2-carboxylic acid (intermediate 3) and cyclobutyl-amine (commercially available) | 368.1 |

TABLE 1-continued

| Example No. | Name | Starting materials | MW found [MH+] |
|---|---|---|---|
| 139 | 4-[3-(4-Fluoro-phenyl)-5-methyl-isoxazole-4-carbonyl]-1H-pyrrole-2-carboxylic acid (3-fluoro-phenyl)-amide | 4-[3-(4-Fluoro-phenyl)-5-methyl-isoxazole-4-carbonyl]-1H-pyrrole-2-carboxylic acid (intermediate 3) and 3-fluoro-phenyl-amine (commercially available) | 408.1 |
| 140 | 4-[3-(4-Fluoro-phenyl)-5-methyl-isoxazole-4-carbonyl]-1H-pyrrole-2-carboxylic acid (2-hydroxy-ethyl)-amide | 4-[3-(4-Fluoro-phenyl)-5-methyl-isoxazole-4-carbonyl]-1H-pyrrole-2-carboxylic acid (intermediate 3) and 2-hydroxy-ethyl-amine (commercially available) | 358.1 |
| 141 | 4-[3-(4-Fluoro-phenyl)-5-methyl-isoxazole-4-carbonyl]-1H-pyrrole-2-carboxylic acid [2-(1H-imidazol-4-yl)-ethyl]-amide | 4-[3-(4-Fluoro-phenyl)-5-methyl-isoxazole-4-carbonyl]-1H-pyrrole-2-carboxylic acid (intermediate 3) and 2-(1H-imidazol-4-yl)-ethyl-amine (commercially available) | 408.1 |

| Example No. | Structure | Name | Starting materials | MW found [MH+] |
|---|---|---|---|---|
| 142 | 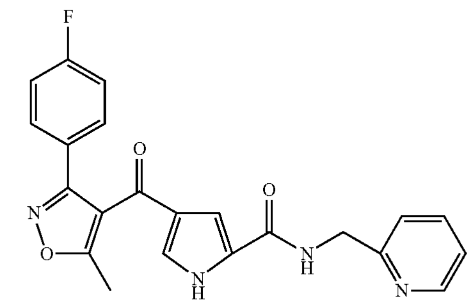 | 4-[3-(4-Fluoro-phenyl)-5-methyl-isoxazole-4-carbonyl]-1H-pyrrole-2-carboxylic acid (pyridin-2-ylmethyl)-amide | 4-[3-(4-Fluoro-phenyl)-5-methyl-isoxazole-4-carbo-nyl]-1H-pyrrole-2-carboxylic acid (intermediate 3) and pyridin-2-ylmethyl-amine (commercially available) | 405.1 |
| 143 | 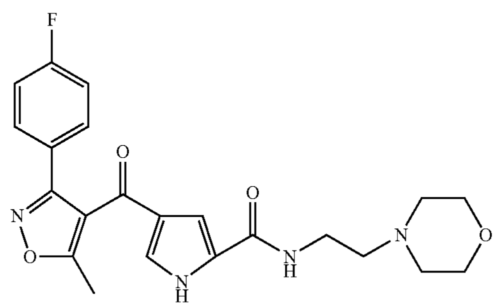 | 4-[3-(4-Fluoro-phenyl)-5-methyl-isoxazole-4-carbonyl]-1H-pyrrole-2-carboxylic acid (2-morpholin-4-yl-ethyl)-amide | 4-[3-(4-Fluoro-phenyl)-5-methyl-isoxazole-4-carbo-nyl]-1H-pyrrole-2-carboxylic acid (intermediate 3) and 2-morpholin-4-yl-ethyl-amine (commercially available) | 427.1 |
| 144 | 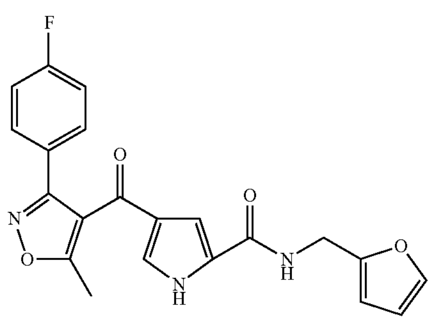 | 4-[3-(4-Fluoro-phenyl)-5-methyl-isoxazole-4-carbonyl]-1H-pyrrole-2-carboxylic acid (furan-2-ylmethyl)-amide | 4-[3-(4-Fluoro-phenyl)-5-methyl-isoxazole-4-carbonyl]-1H-pyrrole-2-carboxylic acid (intermediate 3) and furan-2-ylmethyl-amine (commercially available) | 394.1 |

TABLE 1-continued

| Example No. | Structure | Name | Starting materials | MW found [MH+] |
|---|---|---|---|---|
| 145 | 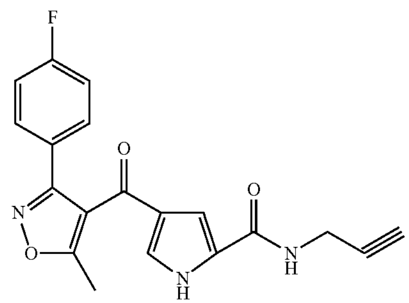 | 4-[3-(4-Fluoro-phenyl)-5-methyl-isoxazole-4-carbonyl]-1H-pyrrole-2-carboxylic acid prop-2-ynylamide | 4-[3-(4-Fluoro-phenyl)-5-methyl-isoxazole-4-carbonyl]-1H-pyrrole-2-carboxylic acid (intermediate 3) and prop-2-ynyl-amine (commercially available) | 352.1 |
| 146 | 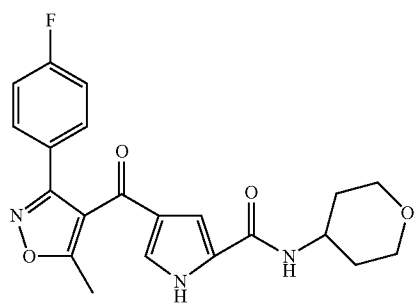 | 4-[3-(4-Fluoro-phenyl)-5-methyl-isoxazole-4-carbonyl]-1H-pyrrole-2-carboxylic acid (tetrahydro-pyran-4-yl)-amide | 4-[3-(4-Fluoro-phenyl)-5-methyl-isoxazole-4-carbonyl]-1H-pyrrole-2-carboxylic acid (intermediate 3) and tetrahydro-pyran-4-yl-amine (commercially available) | 398.1 |
| 147 | 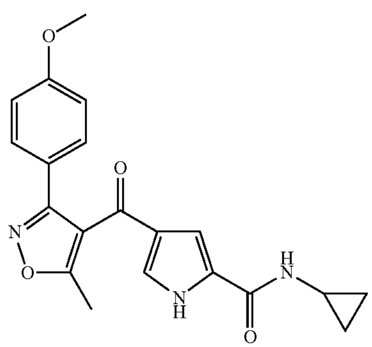 | 4-[3-(4-Methoxy-phenyl)-5-methyl-isoxazole-4-carbonyl]-1H-pyrrole-2-carboxylic acid cyclopropylamide | 4-[3-(4-Methoxy-phenyl)-5-methyl-isoxazole-4-carbonyl]-1H-pyrrole-2-carboxylic acid (intermediate 4) and cyclopropyl-amine (commercially available) | 366.2 |

TABLE 1-continued

| Example No. | Structure | Name | Starting materials | MW found [MH+] |
|---|---|---|---|---|
| 148 | 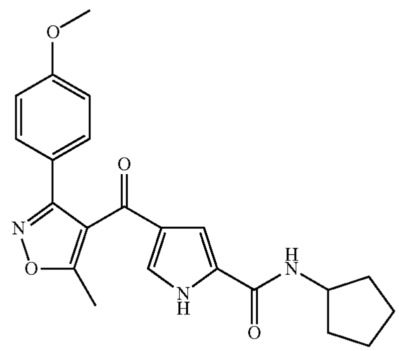 | 4-[3-(4-Methoxy-phenyl)-5-methyl-isoxazole-4-carbonyl]-1H-pyrrole-2-carboxylic acid cyclopentylamide | 4-[3-(4-Methoxy-phenyl)-5-methyl-isoxazole-4-carbonyl]-1H-pyrrole-2-carboxylic acid (intermediate 4) and cyclopentyl-amine (commercially available) | 394.2 |
| 149 | 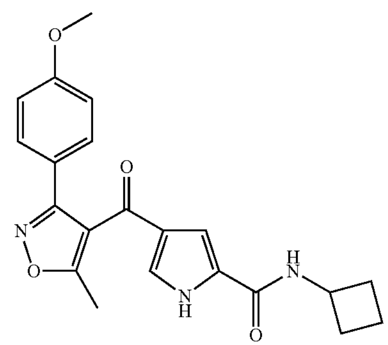 | 4-[3-(4-Methoxy-phenyl)-5-methyl-isoxazole-4-carbonyl]-1H-pyrrole-2-carboxylic acid cyclobutylamide | 4-[3-(4-Methoxy-phenyl)-5-methyl-isoxazole-4-carbonyl]-1H-pyrrole-2-carboxylic acid (intermediate 4) and cyclobutyl-amine (commercially available) | 380.2 |

TABLE 1-continued

| Example No. | Structure | Name | Starting materials | MW found [MH+] |
|---|---|---|---|---|
| 150 | 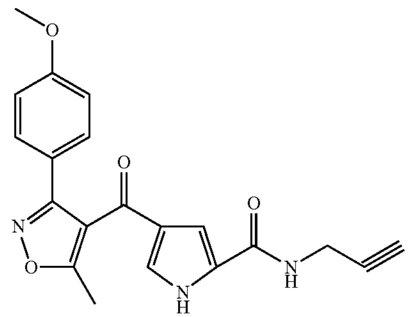 | 4-[3-(4-Methoxy-phenyl)-5-methyl-isoxazole-4-carbonyl]-1H-pyrrole-2-carboxylic acid prop-2-ynylamide | 4-[3-(4-Methoxy-phenyl)-5-methyl-isoxazole-4-carbonyl]-1H-pyrrole-2-carboxylic acid (intermediate 4) and prop-2-ynyl-amine (commercially available) | 364.1 |
| 151 | 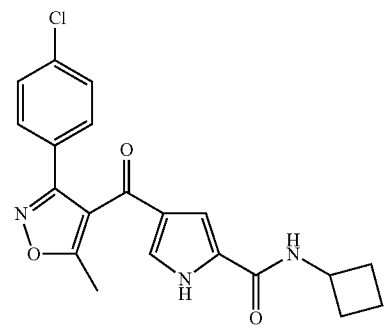 | 4-[3-(4-Chloro-phenyl)-5-methyl-isoxazole-4-carbonyl]-1H-pyrrole-2-carboxylic acid cyclobutylamide | 4-[3-(4-Chloro-phenyl)-5-methyl-isoxazole-4-carbonyl]-1H-pyrrole-2-carboxylic acid (intermediate 5) and cyclobutyl-amine (commercially available) | 384.0 |
| 152 | 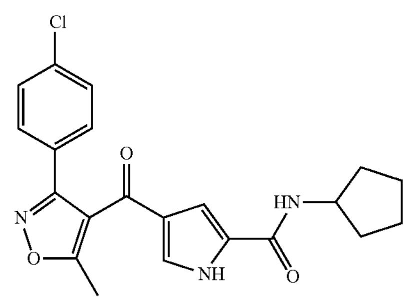 | 4-[3-(4-Chloro-phenyl)-5-methyl-isoxazole-4-carbonyl]-1H-pyrrole-2-carboxylic acid cyclopentylamide | 4-[3-(4-Chloro-phenyl)-5-methyl-isoxazole-4-carbonyl]-1H-pyrrole-2-carboxylic acid (intermediate 5) and cyclopentyl-amine (commercially available) | 398.1 |

TABLE 1-continued

| Example No. | Name | Structure | Starting materials | MW found [MH+] |
|---|---|---|---|---|
| 153 | 4-[3-(4-Chloro-phenyl)-5-methyl-isoxazole-4-carbonyl]-1H-pyrrole-2-carboxylic acid (2-hydroxy-ethyl)-amide | 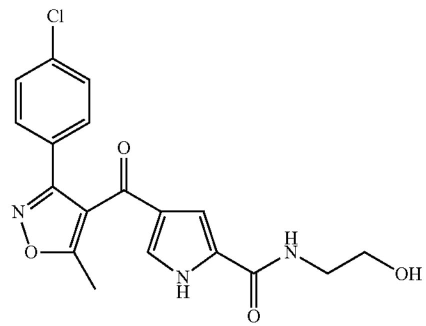 | 4-[3-(4-Chloro-phenyl)-5-methyl-isoxazole-4-carbonyl]-1H-pyrrole-2-carboxylic acid (intermediate 5) and 2-hydroxy-ethyl-amine (commercially available) | 374.1 |
| 154 | 4-[3-(4-Chloro-phenyl)-5-methyl-isoxazole-4-carbonyl]-1H-pyrrole-2-carboxylic acid cyclopropylamide | 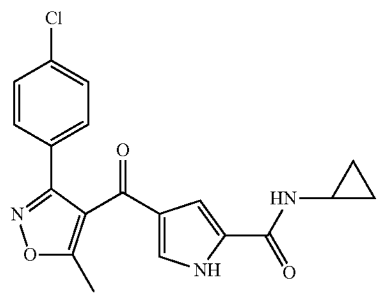 | 4-[3-(4-Chloro-phenyl)-5-methyl-isoxazole-4-carbonyl]-1H-pyrrole-2-carboxylic acid (intermediate 5) and cyclopropyl-amine (commercially available) | 370.1 |
| 155 | 4-[3-(4-Chloro-phenyl)-5-methyl-isoxazole-4-carbonyl]-1H-pyrrole-2-carboxylic acid (3-fluoro-phenyl)-amide | 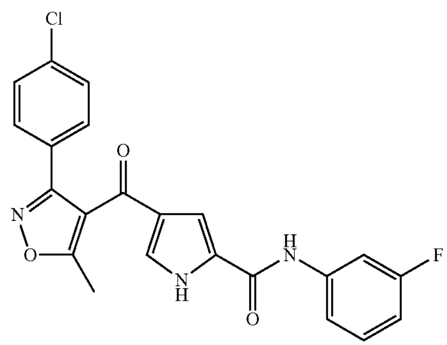 | 4-[3-(4-Chloro-phenyl)-5-methyl-isoxazole-4-carbonyl]-1H-pyrrole-2-carboxylic acid (intermediate 5) and 3-fluoro-phenyl-amine (commercially available) | 424.1 |

TABLE 1-continued

| Example No. | Structure | Name | Starting materials | MW found [MH+] |
|---|---|---|---|---|
| 156 | 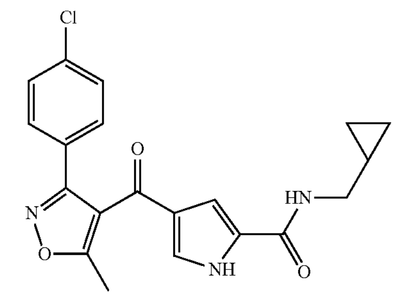 | 4-[3-(4-Chloro-phenyl)-5-methyl-isoxazole-4-carbonyl]-1H-pyrrole-2-carboxylic acid cyclopropylmethyl-amide | 4-[3-(4-Chloro-phenyl)-5-methyl-isoxazole-4-carbonyl]-1H-pyrrole-2-carboxylic acid (intermediate 5) and cyclopropylmethyl-amine (commercially available) | 384.0 |
| 157 | 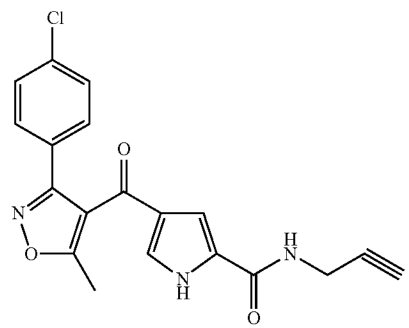 | 4-[3-(4-Chloro-phenyl)-1H-pyrrole-2-carboxylic acid prop-2-ynylamide | 4-[3-(4-Chloro-phenyl)-5-methyl-isoxazole-4-carbo-nyl]-1H-pyrrole-2-carboxylic acid (intermediate 5) and prop-2-ynyl-amine (commercially available) | 368.0 |
| 158 | 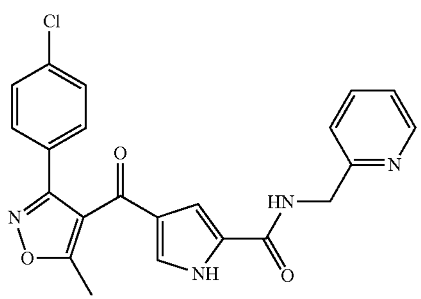 | 4-[3-(4-Chloro-phenyl)-5-methyl-isoxazole-4-carbonyl]-1H-pyrrole-2-carboxylic acid (pyridin-2-ylmethyl)-amide | 4-[3-(4-Chloro-phenyl)-1H-pyrrole-2-carboxylic acid (intermediate 5) and pyridin-2-ylmethyl-amine (commercially available) | 421.0 |

TABLE 1-continued

| Example No. | Structure | Name | Starting materials | MW found [MH+] |
|---|---|---|---|---|
| 159 | 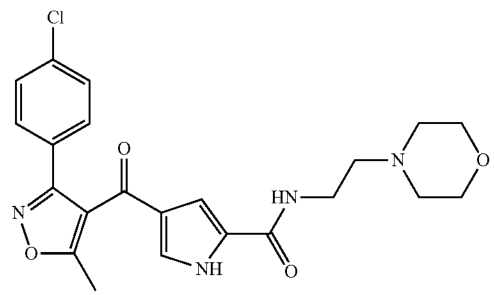 | 4-[3-(4-Chloro-phenyl)-5-methyl-isoxazole-4-carbonyl]-1H-pyrrole-2-carboxylic acid (2-morpholin-4-yl-ethyl)-amide | 4-[3-(4-Chloro-phenyl)-5-methyl-isoxazole-4-carbonyl]-1H-pyrrole-2-carboxylic acid (intermediate 5) and 2-morpholin-4-yl-ethyl-amine (commercially available) | 443.1 |
| 160 | 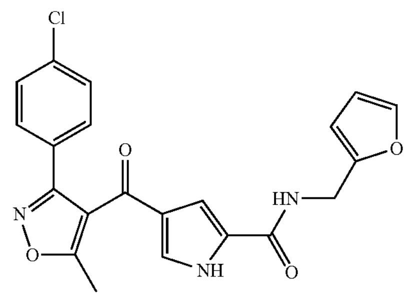 | 4-[3-(4-Chloro-phenyl)-5-methyl-isoxazole-4-carbonyl]-1H-pyrrole-2-carboxylic acid (furan-2-ylmethyl)-amide | 4-[3-(4-Chloro-phenyl)-5-methyl-isoxazole-4-carbonyl]-1H-pyrrole-2-carboxylic acid (intermediate 5) and furan-2-ylmethyl-amine (commercially available) | 410.0 |
| 161 | 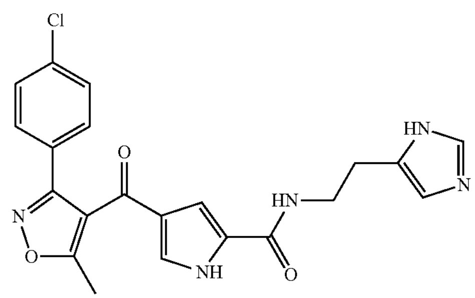 | 4-[3-(4-Chloro-phenyl)-5-methyl-isoxazole-4-carbonyl]-1H-pyrrole-2-carboxylic acid [2-(1H-imidazol-4-yl)-ethyl]-amide | 4-[3-(4-Chloro-phenyl)-5-methyl-isoxazole-4-carbonyl]-1H-pyrrole-2-carboxylic acid (intermediate 5) and 2-(1H-imidazol-4-yl)-ethyl-amine (commercially available) | 424.2 |

TABLE 1-continued

| Example No. | Structure | Name | Starting materials | MW found [MH+] |
|---|---|---|---|---|
| 162 | 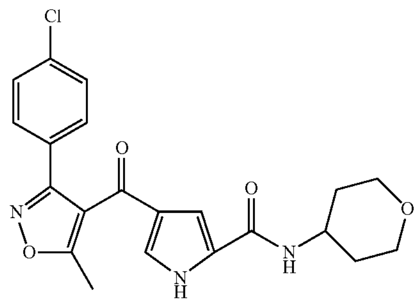 | 4-[3-(4-Chloro-phenyl)-5-methyl-isoxazole-4-carbonyl]-1H-pyrrole-2-carboxylic acid (tetrahydro-pyran-4-yl)-amide | 4-[3-(4-Chloro-phenyl)-5-methyl-isoxazole-4-carbonyl]-1H-pyrrole-2-carboxylic acid (intermediate 5) and tetrahydro-pyran-4-yl)-amine (commercially available) | 414.0 |
| 163 | 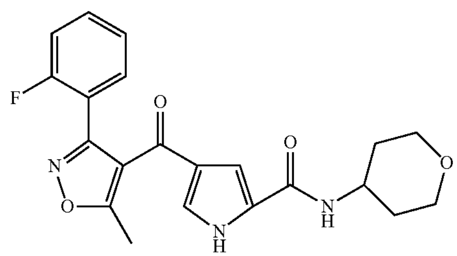 | 4-[3-(2-Fluoro-phenyl)-5-methyl-isoxazole-4-carbonyl]-1H-pyrrole-2-carboxylic acid (tetrahydro-pyran-4-yl)-amide | 4-[3-(2-Fluoro-phenyl)-5-methyl-isoxazole-4-carbonyl]-1H-pyrrole-2-carboxylic acid (intermediate 6) and tetrahydro-pyran-4-yl)-amine (commercially available) | 398.1 |
| 164 | 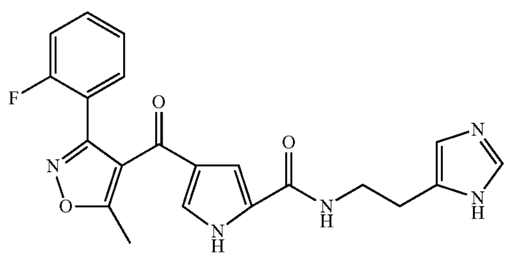 | 4-[3-(2-Fluoro-phenyl)-5-methyl-isoxazole-4-carbonyl]-1H-pyrrole-2-carboxylic acid [2-(1H-imidazol-4-yl)-ethyl]-amide | 4-[3-(2-Fluoro-phenyl)-5-methyl-isoxazole-4-carbonyl]-1H-pyrrole-2-carboxylic acid (intermediate 6) and 2-(1H-imidazol-4-yl)-ethyl-amine (commercially available) | 408.1 |

TABLE 1-continued

| Example No. | Structure | Name | Starting materials | MW found [MH+] |
|---|---|---|---|---|
| 165 | 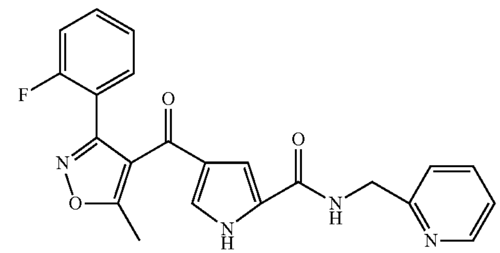 | 4-[3-(2-Fluoro-phenyl)-5-methyl-isoxazole-4-carbonyl]-1H-pyrrole-2-carboxylic acid (pyridin-2-ylmethyl)-amide | 4-[3-(2-Fluoro-phenyl)-5-methyl-isoxazole-4-carbonyl]-1H-pyrrole-2-carboxylic acid (intermediate 6) and pyridin-2-ylmethyl-amine (commercially available) | 405.1 |
| 166 | 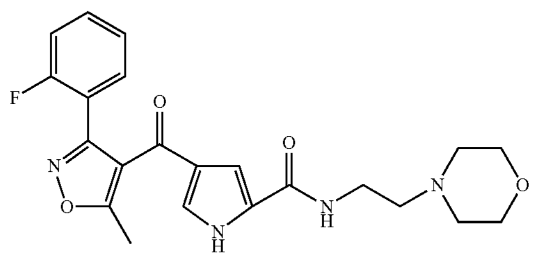 | 4-[3-(2-Fluoro-phenyl)-5-methyl-isoxazole-4-carbonyl]-1H-pyrrole-2-carboxylic acid (2-morpholin-4-yl-ethyl)-amide | 4-[3-(2-Fluoro-phenyl)-5-methyl-isoxazole-4-carbonyl]-1H-pyrrole-2-carboxylic acid (intermediate 6) and 2-morpholin-4-yl-ethyl-amine (commercially available) | 427.1 |
| 167 | 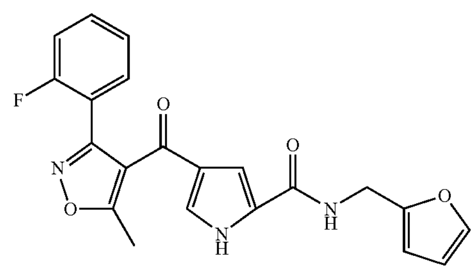 | 4-[3-(2-Fluoro-phenyl)-5-methyl-isoxazole-4-carbonyl]-1H-pyrrole-2-carboxylic acid (furan-2-ylmethyl)-amide | 4-[3-(2-Fluoro-phenyl)-5-methyl-isoxazole-4-carbonyl]-1H-pyrrole-2-carboxylic acid (intermediate 6) and furan-2-ylmethyl-amine (commercially available) | 394.1 |

TABLE 1-continued

| Example No. | Structure | Name | Starting materials | MW found [MH+] |
|---|---|---|---|---|
| 168 | 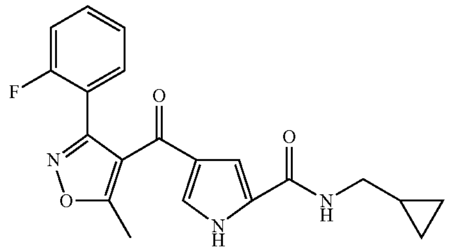 | 4-[3-(2-Fluoro-phenyl)-5-methyl-isoxazole-4-carbonyl]-1H-pyrrole-2-carboxylic acid cyclopropylmethyl-amide | 4-[3-(2-Fluoro-phenyl)-5-methyl-isoxazole-4-carbonyl]-1H-pyrrole-2-carboxylic acid (intermediate 6) and cyclopropylmethyl-amine (commercially available) | 368.1 |
| 169 | 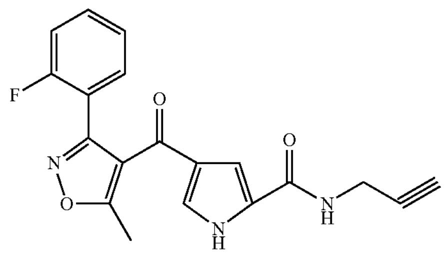 | 4-[3-(2-Fluoro-phenyl)-5-methyl-isoxazole-4-carbonyl]-1H-pyrrole-2-carboxylic acid prop-2-ynylamide | 4-[3-(2-Fluoro-phenyl)-5-methyl-isoxazole-4-carbonyl]-1H-pyrrole-2-carboxylic acid (intermediate 6) and prop-2-ynyl-amine (commercially available) | 352.1 |
| 170 | 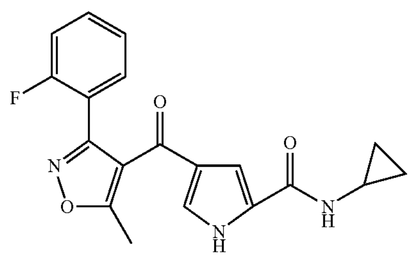 | 4-[3-(2-Fluoro-phenyl)-5-methyl-isoxazole-4-carbonyl]-1H-pyrrole-2-carboxylic acid cyclopropylamide | 4-[3-(2-Fluoro-phenyl)-5-methyl-isoxazole-4-carbonyl]-1H-pyrrole-2-carboxylic acid (intermediate 6) and cyclopropyl-amine (commercially available) | 354.1 |

TABLE 1-continued

| Example No. | Name | Starting materials | MW found [MH+] |
|---|---|---|---|
| 171 | 4-[3-(2-Fluoro-phenyl)-5-methyl-isoxazole-4-carbonyl]-1H-pyrrole-2-carboxylic acid (2-hydroxy-ethyl)-amide | 4-[3-(2-Fluoro-phenyl)-5-methyl-isoxazole-4-carbonyl]-1H-pyrrole-2-carboxylic acid (intermediate 6) and 2-hydroxy-ethyl-amine (commercially available) | 358.1 |
| 172 | 4-[3-(2-Fluoro-phenyl)-5-methyl-isoxazole-4-carbonyl]-1H-pyrrole-2-carboxylic acid cyclobutylamide | 4-[3-(2-Fluoro-phenyl)-5-methyl-isoxazole-4-carbonyl]-1H-pyrrole-2-carboxylic acid (intermediate 6) and cyclobutyl-amine (commercially available) | 368.1 |
| 173 | 4-[3-(2-Fluoro-phenyl)-5-methyl-isoxazole-4-carbonyl]-1H-pyrrole-2-carboxylic acid cyclopentylamide | 4-[3-(2-Fluoro-phenyl)-5-methyl-isoxazole-4-carbonyl]-1H-pyrrole-2-carboxylic acid (intermediate 6) and cyclopentyl-amine (commercially available) | 382.1 |

TABLE 1-continued

| Example No. | Structure | Name | Starting materials | MW found [MH+] |
|---|---|---|---|---|
| 174 | 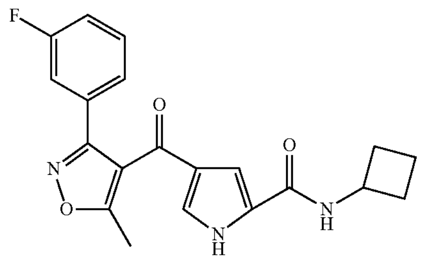 | 4-[3-(3-Fluoro-phenyl)-5-methyl-isoxazole-4-carbonyl]-1H-pyrrole-2-carboxylic acid cyclobutylamide | 4-[3-(3-Fluoro-phenyl)-5-methyl-isoxazole-4-carbonyl]-1H-pyrrole-2-carboxylic acid (intermediate 7) and cyclobutyl-amine (commercially available) | 368.2 |
| 175 | 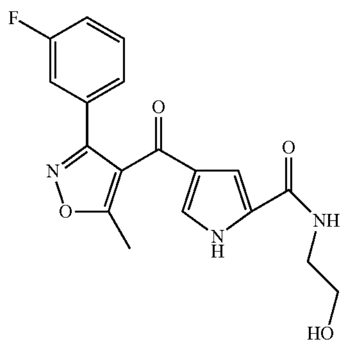 | 4-[3-(3-Fluoro-phenyl)-5-methyl-isoxazole-4-carbonyl]-1H-pyrrole-2-carboxylic acid (2-hydroxy-ethyl)-amide | 4-[3-(3-Fluoro-phenyl)-5-methyl-isoxazole-4-carbonyl]-1H-pyrrole-2-carboxylic acid (intermediate 7) and 2-hydroxy-ethyl-amine (commercially available) | 358.1 |
| 176 | 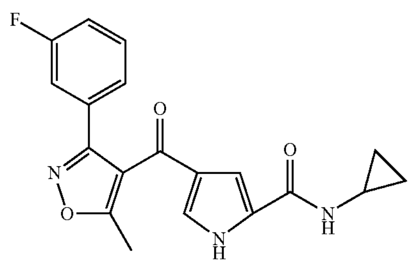 | 4-[3-(3-Fluoro-phenyl)-5-methyl-isoxazole-4-carbonyl]-1H-pyrrole-2-carboxylic acid cyclopropylamide | 4-[3-(3-Fluoro-phenyl)-5-methyl-isoxazole-4-carbonyl]-1H-pyrrole-2-carboxylic acid (intermediate 7) and cyclopropyl-amine (commercially available) | 354.1 |

TABLE 1-continued

| Example No. | Structure | Name | Starting materials | MW found [MH+] |
|---|---|---|---|---|
| 177 | 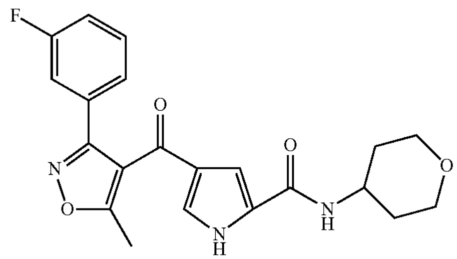 | 4-[3-(3-Fluoro-phenyl)-5-methyl-isoxazole-4-carbonyl]-1H-pyrrole-2-carboxylic acid (tetrahydro-pyran-4-yl)-amide | 4-[3-(3-Fluoro-phenyl)-5-methyl-isoxazole-4-carbonyl]-1H-pyrrole-2-carboxylic acid (intermediate 7) and tetrahydro-pyran-4-yl-amine (commercially available) | 398.1 |
| 178 | 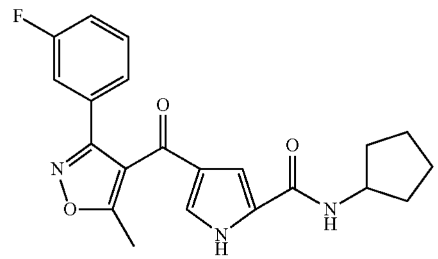 | 4-[3-(3-Fluoro-phenyl)-5-methyl-isoxazole-4-carbonyl]-1H-pyrrole-2-carboxylic acid cyclopentylamide | 4-[3-(3-Fluoro-phenyl)-5-methyl-isoxazole-4-carbonyl]-1H-pyrrole-2-carboxylic acid (intermediate 7) and cyclopentyl-amine (commercially available) | 382.1 |
| 179 | 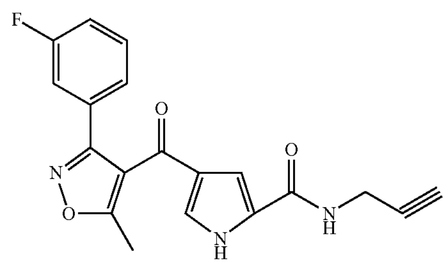 | 4-[3-(3-Fluoro-phenyl)-5-methyl-isoxazole-4-carbonyl]-1H-pyrrole-2-carboxylic acid prop-2-ynylamide | 4-[3-(3-Fluoro-phenyl)-5-methyl-isoxazole-4-carbonyl]-1H-pyrrole-2-carboxylic acid (intermediate 7) and prop-2-ynyl-amine (commercially available) | 352.1 |

TABLE 1-continued

| Example No. | Name | Structure | Starting materials | MW found [MH+] |
|---|---|---|---|---|
| 180 | 4-[3-(3-Fluoro-phenyl)-5-methyl-isoxazole-4-carbonyl]-1H-pyrrole-2-carboxylic acid cyclopropylmethyl-amide | 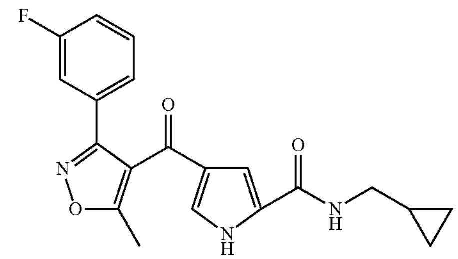 | 4-[3-(3-Fluoro-phenyl)-5-methyl-isoxazole-4-carbonyl]-1H-pyrrole-2-carboxylic acid (intermediate 7) and cyclopropylmethyl-amine (commercially available) | 368.1 |
| 181 | 4-[3-(3-Fluoro-phenyl)-5-methyl-isoxazole-4-carbonyl]-1H-pyrrole-2-carboxylic acid (furan-2-ylmethyl)-amide | 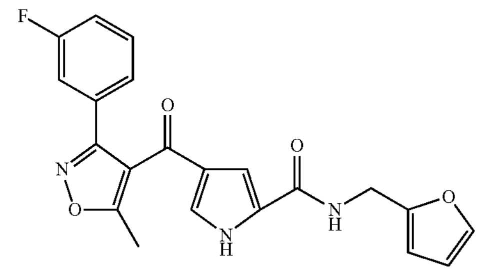 | 4-[3-(3-Fluoro-phenyl)-5-methyl-isoxazole-4-carbonyl]-1H-pyrrole-2-carboxylic acid (intermediate 7) and furan-2-ylmethyl-amine (commercially available) | 394.1 |
| 182 | 4-[3-(3-Fluoro-phenyl)-5-methyl-isoxazole-4-carbonyl]-1H-pyrrole-2-carboxylic acid (pyridin-2-ylmethyl)-amide | 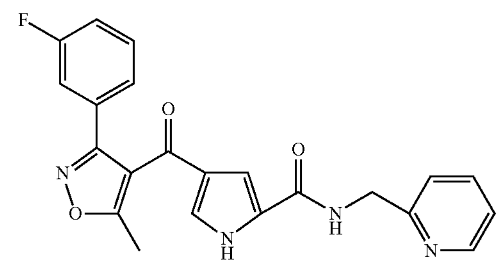 | 4-[3-(3-Fluoro-phenyl)-5-methyl-isoxazole-4-carbonyl]-1H-pyrrole-2-carboxylic acid (intermediate 7) and pyridin-2-ylmethyl-amine (commercially available) | 405.2 |

TABLE 1-continued

| Example No. | Structure | Name | Starting materials | MW found [MH+] |
|---|---|---|---|---|
| 183 | 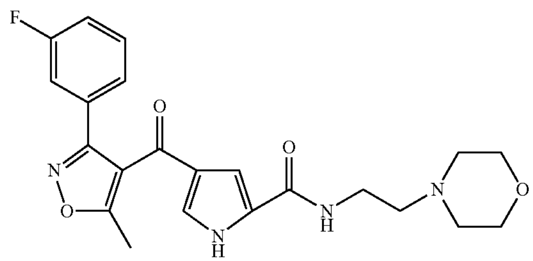 | 4-[3-(3-Fluoro-phenyl)-5-methyl-isoxazole-4-carbonyl]-1H-pyrrole-2-carboxylic acid (2-morpholin-4-yl-ethyl)-amide | 4-[3-(3-Fluoro-phenyl)-5-methyl-isoxazole-4-carbonyl]-1H-pyrrole-2-carboxylic acid (intermediate 7) and 2-morpholin-4-yl-ethyl-amine (commercially available) | 427.1 |
| 184 | 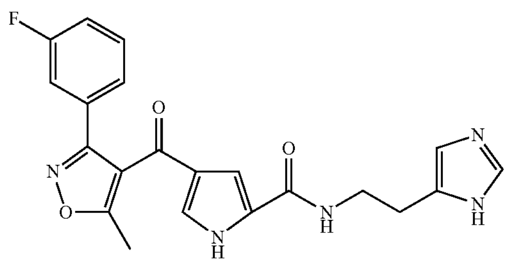 | 4-[3-(3-Fluoro-phenyl)-5-methyl-isoxazole-4-carbonyl]-1H-pyrrole-2-carboxylic acid [2-(1H-imidazol-4-yl)-ethyl]-amide | 4-[3-(3-Fluoro-phenyl)-5-methyl-isoxazole-4-carbonyl]-1H-pyrrole-2-carboxylic acid (intermediate 7) and 2-(1H-imidazol-4-yl)-ethyl-amine (commercially available) | 408.1 |
| 185 | 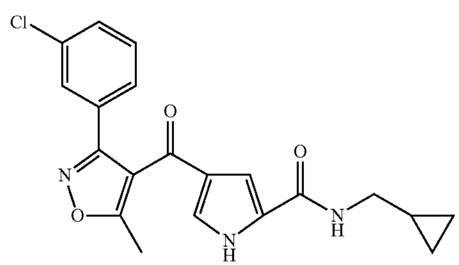 | 4-[3-(3-Chloro-phenyl)-5-methyl-isoxazole-4-carbonyl]-1H-pyrrole-2-carboxylic acid cyclopropylmethyl-amide | 4-[3-(3-Chloro-phenyl)-5-methyl-isoxazole-4-carbonyl]-1H-pyrrole-2-carboxylic acid (intermediate 8) and cyclopropylmethyl-amine (commercially available) | 384.0 |

TABLE 1-continued

| Example No. | Structure | Name | Starting materials | MW found [MH+] |
|---|---|---|---|---|
| 186 | 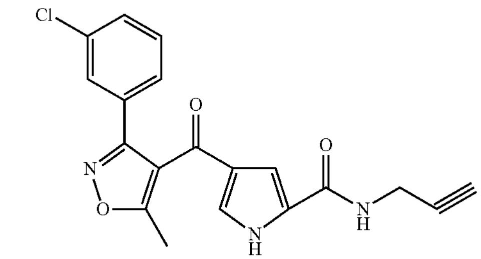 | 4-[3-(3-Chloro-phenyl)-5-methyl-isoxazole-4-carbonyl]-1H-pyrrole-2-carboxylic acid prop-2-ynylamide | 4-[3-(3-Chloro-phenyl)-5-methyl-isoxazole-4-carbonyl]-1H-pyrrole-2-carboxylic acid (intermediate 8) and prop-2-ynyl-amine (commercially available) | 368.0 |
| 187 | 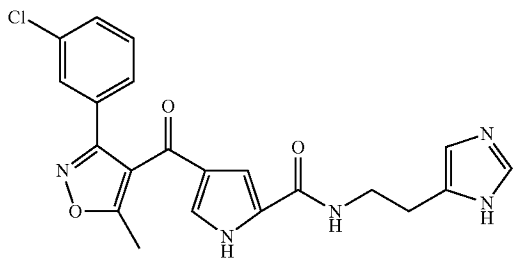 | 4-[3-(3-Chloro-phenyl)-5-methyl-isoxazole-4-carbonyl]-1H-pyrrole-2-carboxylic acid [2-(1H-imidazol-4-yl)-ethyl]-amide | 4-[3-(3-Chloro-phenyl)-5-methyl-isoxazole-4-carbonyl]-1H-pyrrole-2-carboxylic acid (intermediate 8) and 2-(1H-imidazol-4-yl)-ethyl-amine (commercially available) | 424.0 |
| 188 | 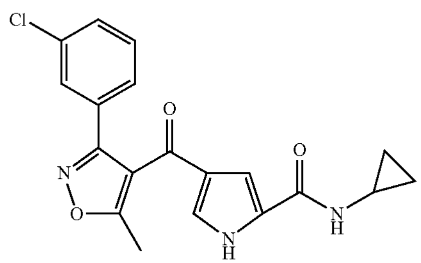 | 4-[3-(3-Chloro-phenyl)-5-methyl-isoxazole-4-carbonyl]-1H-pyrrole-2-carboxylic acid cyclopropylamide | 4-[3-(3-Chloro-phenyl)-5-methyl-isoxazole-4-carbonyl]-1H-pyrrole-2-carboxylic acid (intermediate 8) and cyclopropyl-amine (commercially available) | 370.0 |

TABLE 1-continued

| Example No. | Structure | Name | Starting materials | MW found [MH+] |
|---|---|---|---|---|
| 189 | 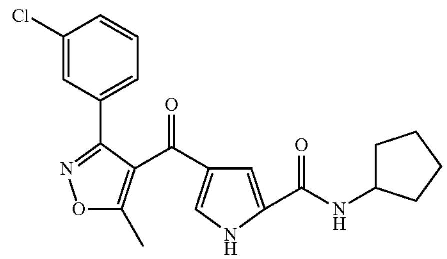 | 4-[3-(3-Chloro-phenyl)-5-methyl-isoxazole-4-carbonyl]-1H-pyrrole-2-carboxylic acid cyclopentylamide | 4-[3-(3-Chloro-phenyl)-5-methyl-isoxazole-4-carbonyl]-1H-pyrrole-2-carboxylic acid (intermediate 8) and cyclopentyl-amine (commercially available) | 398.1 |
| 190 | 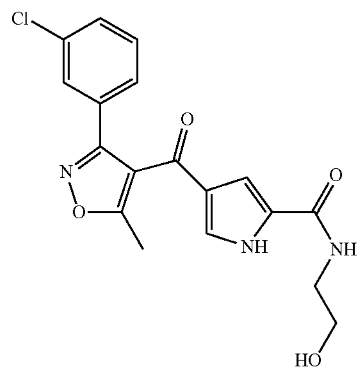 | 4-[3-(3-Chloro-phenyl)-5-methyl-isoxazole-4-carbonyl]-1H-pyrrole-2-carboxylic acid (2-hydroxy-ethyl)-amide | 4-[3-(3-Chloro-phenyl)-5-methyl-isoxazole-4-carbonyl]-1H-pyrrole-2-carboxylic acid (intermediate 8) and 2-hydroxy-ethyl-amine (commercially available) | 374.0 |
| 191 | 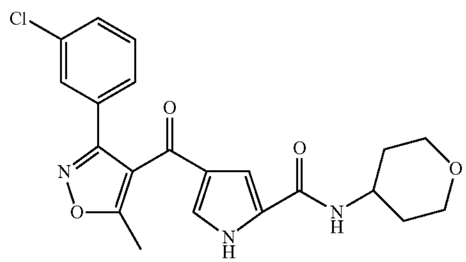 | 4-[3-(3-Chloro-phenyl)-5-methyl-isoxazole-4-carbonyl]-1H-pyrrole-2-carboxylic acid (tetrahydro-pyran-4-yl)-amide | 4-[3-(3-Chloro-phenyl)-5-methyl-isoxazole-4-carbonyl]-1H-pyrrole-2-carboxylic acid (intermediate 8) and tetrahydro-pyran-4-yl-amine (commercially available) | 414.1 |

TABLE 1-continued

| Example No. | Structure | Name | Starting materials | MW found [MH+] |
|---|---|---|---|---|
| 192 | 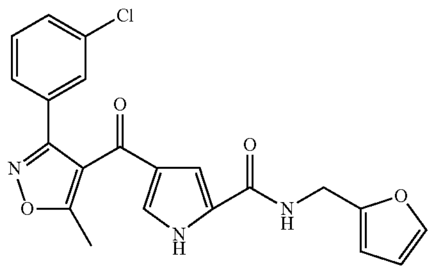 | 4-[3-(3-Chloro-phenyl)-5-methyl-isoxazole-4-carbonyl]-1H-pyrrole-2-carboxylic acid (furan-2-ylmethyl)-amide | 4-[3-(3-Chloro-phenyl)-5-methyl-isoxazole-4-carbonyl]-1H-pyrrole-2-carboxylic acid (intermediate 8) and furan-2-ylmethyl-amine (commercially available) | 410.1 |
| 193 | 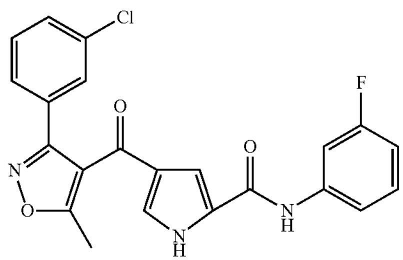 | 4-[3-(3-Chloro-phenyl)-5-methyl-isoxazole-4-carbonyl]-1H-pyrrole-2-carboxylic acid (3-fluoro-phenyl)-amide | 4-[3-(3-Chloro-phenyl)-5-methyl-isoxazole-4-carbonyl]-1H-pyrrole-2-carboxylic acid (intermediate 8) and 3-fluoro-phenyl-amine (commercially available) | 424.0 |
| 194 | 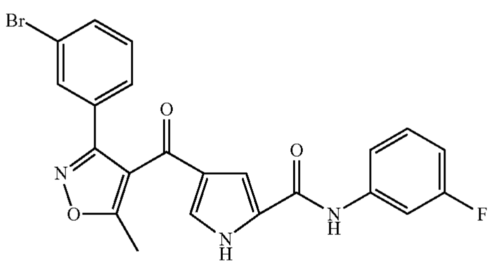 | 4-[3-(3-Bromo-phenyl)-5-methyl-isoxazole-4-carbonyl]-1H-pyrrole-2-carboxylic acid (3-fluoro-phenyl)-amide | 4-[3-(3-Bromo-phenyl)-5-methyl-isoxazole-4-carbonyl]-1H-pyrrole-2-carboxylic acid (intermediate 9) and 3-fluoro-phenyl-amine (commercially available) | 468.0 |

TABLE 1-continued

| Example No. | Structure | Name | Starting materials | MW found [MH+] |
|---|---|---|---|---|
| 195 | 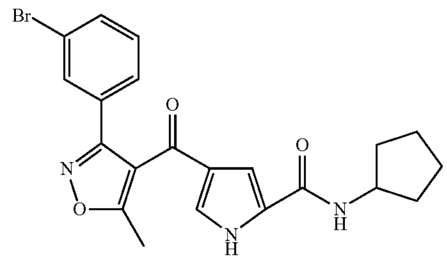 | 4-[3-(3-Bromo-phenyl)-5-methyl-isoxazole-4-carbonyl]-1H-pyrrole-2-carboxylic acid cyclopentylamide | 4-[3-(3-Bromo-phenyl)-5-methyl-isoxazole-4-carbonyl]-1H-pyrrole-2-carboxylic acid (intermediate 9) and cyclopentyl-amine (commercially available) | 442.1 |
| 196 | 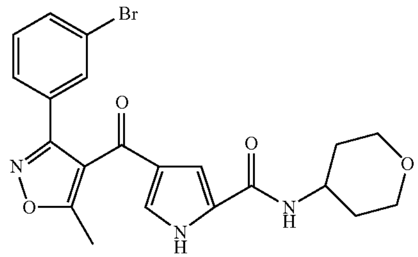 | 4-[3-(3-Bromo-phenyl)-5-methyl-isoxazole-4-carbonyl]-1H-pyrrole-2-carboxylic acid (tetrahydro-pyran-4-yl)-amide | 4-[3-(3-Bromo-phenyl)-5-methyl-isoxazole-4-carbonyl]-1H-pyrrole-2-carboxylic acid (intermediate 9) and tetrahydro-pyran-4-yl-amine (commercially available) | 458.0 |
| 197 | 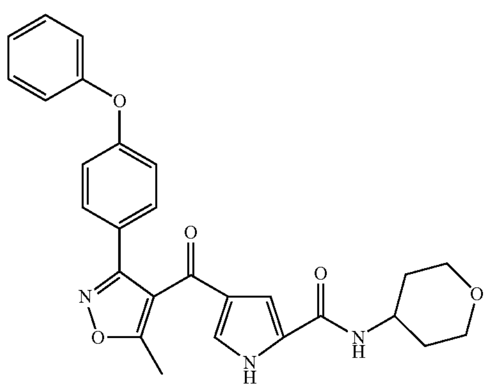 | 4-[5-Methyl-3-(4-phenoxy-phenyl)-isoxazole-4-carbonyl]-1H-pyrrole-2-carboxylic acid (tetrahydro-pyran-4-yl)-amide | 4-[5-Methyl-3-(4-phenoxy-phenyl)-isoxazole-4-carbonyl]-1H-pyrrole-2-carboxylic acid (intermediate 10) and tetrahydro-pyran-4-yl-amine (commercially available) | 472.1 |

TABLE 1-continued

| Example No. | Structure | Name | Starting materials | MW found [MH+] |
|---|---|---|---|---|
| 198 | 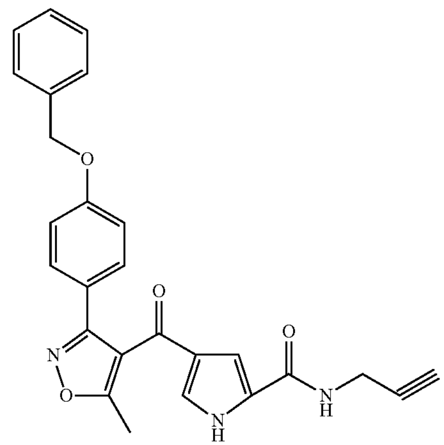 | 4-[3-(4-Benzyloxy-phenyl)-5-methyl-isoxazole-4-carbonyl]-1H-pyrrole-2-carboxylic acid prop-2-ynylamide | 4-[3-(4-Benzyloxy-phenyl)-5-methyl-isoxazole-4-carbonyl]-1H-pyrrole-2-carboxylic acid (intermediate 11) and prop-2-ynyl-amine (commercially available) | 440.2 |
| 199 | 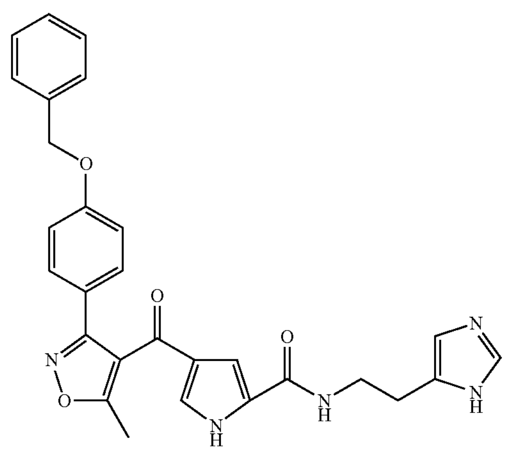 | 4-[3-(4-Benzyloxy-phenyl)-5-methyl-isoxazole-4-carbonyl]-1H-pyrrole-2-carboxylic acid [2-(1H-imidazol-4-yl)-ethyl]-amide | 4-[3-(4-Benzyloxy-phenyl)-5-methyl-isoxazole-4-carbonyl]-1H-pyrrole-2-carboxylic acid (intermediate 11) and 2-(1H-imidazol-4-yl)-ethyl-amine (commercially available) | 496.2 |

TABLE 1-continued

| Example No. | Name | Structure | Starting materials | MW found [MH+] |
|---|---|---|---|---|
| 200 | 4-[3-(4-Benzyloxy-phenyl)-5-methyl-isoxazole-4-carbonyl]-1H-pyrrole-2-carboxylic acid (2-morpholin-4-yl-ethyl)-amide | 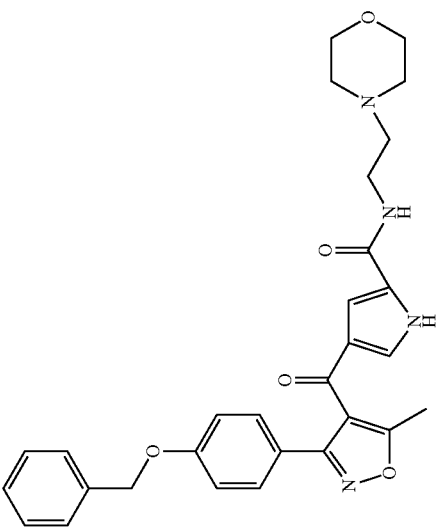 | 4-[3-(4-Benzyloxy-phenyl)-5-methyl-isoxazole-4-carbonyl]-1H-pyrrole-2-carboxylic acid (intermediate 11) and 2-morpholin-4-yl-ethyl-amine (commercially available) | 515.2 |
| 201 | 4-[3-(4-Benzyloxy-phenyl)-5-methyl-isoxazole-4-carbonyl]-1H-pyrrole-2-carboxylic acid cyclopropylamide | 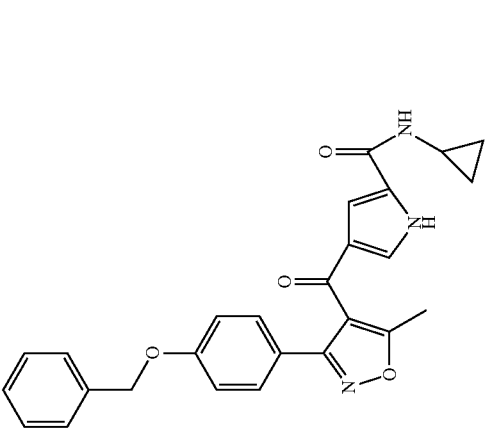 | 4-[3-(4-Benzyloxy-phenyl)-5-methyl-isoxazole-4-carbonyl]-1H-pyrrole-2-carboxylic acid (intermediate 11) and cyclopropyl-amine (commercially available) | 442.1 |

TABLE 1-continued

| Example No. | Name | Structure | Starting materials | MW found [MH+] |
|---|---|---|---|---|
| 202 | 4-[3-(4-Benzyloxy-phenyl)-5-methyl-isoxazole-4-carbonyl]-1H-pyrrole-2-carboxylic acid cyclobutylamide | 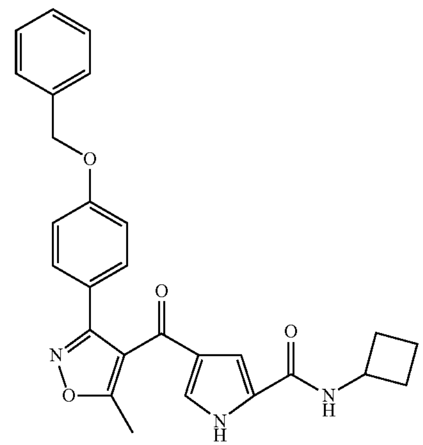 | 4-[3-(4-Benzyloxy-phenyl)-5-methyl-isoxazole-4-carbonyl]-1H-pyrrole-2-carboxylic acid (intermediate 11) and cyclobutyl-amine (commercially available) | 456.2 |
| 203 | 4-[3-(4-Benzyloxy-phenyl)-5-methyl-isoxazole-4-carbonyl]-1H-pyrrole-2-carboxylic acid cyclopentylamide | 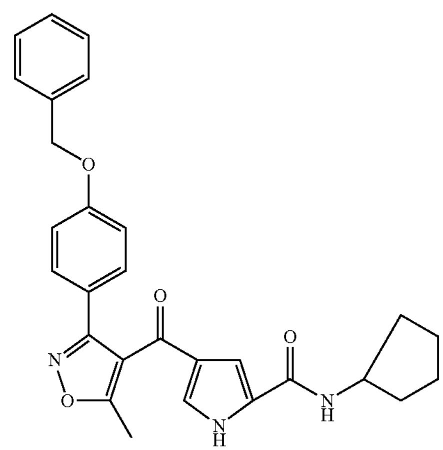 | 4-[3-(4-Benzyloxy-phenyl)-5-methyl-isoxazole-4-carbonyl]-1H-pyrrole-2-carboxylic acid (intermediate 11) and cyclopentyl-amine (commercially available) | 470.2 |

TABLE 1-continued

| Example No. | Name | Structure | Starting materials | MW found [MH+] |
|---|---|---|---|---|
| 204 | 4-[3-(4-Benzyloxy-phenyl)-5-methyl-isoxazole-4-carbonyl]-1H-pyrrole-2-carboxylic acid (2-hydroxy-ethyl)-amide | 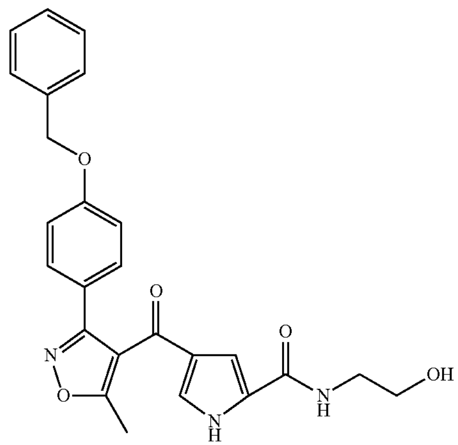 | 4-[3-(4-Benzyloxy-phenyl)-5-methyl-isoxazole-4-carbonyl]-1H-pyrrole-2-carboxylic acid (intermediate 11) and 2-hydroxy-ethyl-amine (commercially available) | 446.2 |
| 205 | 4-[3-(4-Benzyloxy-phenyl)-5-methyl-isoxazole-4-carbonyl]-1H-pyrrole-2-carboxylic acid (tetrahydro-pyran-4-yl)-amide | 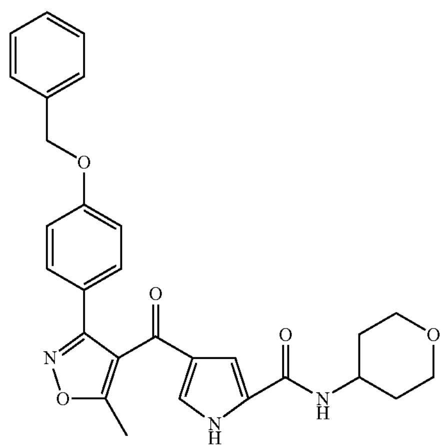 | 4-[3-(4-Benzyloxy-phenyl)-5-methyl-isoxazole-4-carbonyl]-1H-pyrrole-2-carboxylic acid (intermediate 11) and tetrahydro-pyran-4-yl-amine (commercially available) | 486.2 |

TABLE 1-continued

| Example No. | Name | Structure | Starting materials | MW found [MH+] |
|---|---|---|---|---|
| 206 | 4-(5-Ethyl-3-phenyl-isoxazole-4-carbonyl)-1H-pyrrole-2-carboxylic acid [2-(1H-imidazol-4-yl)-ethyl]-amide | 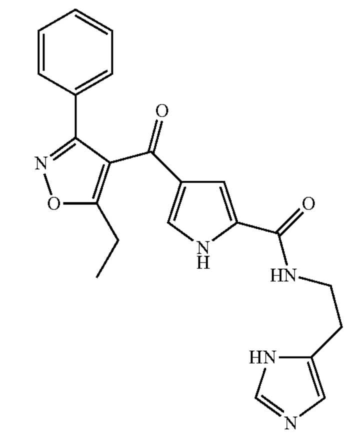 | 4-(5-Ethyl-3-phenyl-isoxazole-4-carbonyl)-1H-pyrrole-2-carboxylic acid (intermediate 12) and 2-(1H-imidazol-4-yl)-ethyl-amine (commercially available) | 404.0 |
| 207 | 4-(5-Ethyl-3-phenyl-isoxazole-4-carbonyl)-1H-pyrrole-2-carboxylic acid (pyridin-2-ylmethyl)-amide | 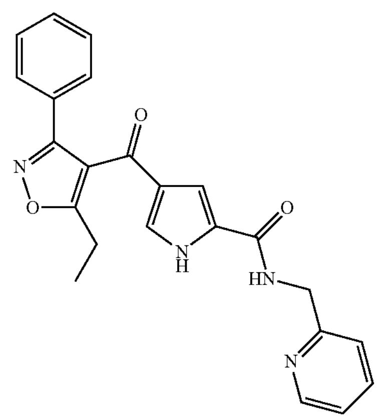 | 4-(5-Ethyl-3-phenyl-isoxazole-4-carbonyl)-1H-pyrrole-2-carboxylic acid (intermediate 12) and pyridin-2-ylmethyl-amine (commercially available) | 401.1 |

TABLE 1-continued

| Example No. | Structure | Name | Starting materials | MW found [MH+] |
|---|---|---|---|---|
| 208 | 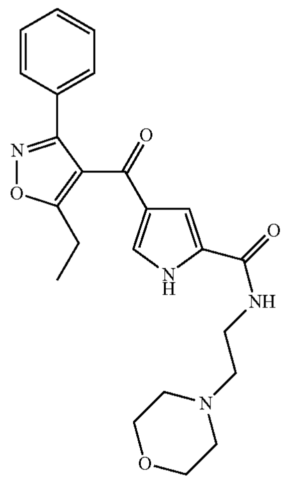 | 4-(5-Ethyl-3-phenyl-isoxazole-4-carbonyl)-1H-pyrrole-2-carboxylic acid (2-morpholin-4-yl-ethyl)-amide | 4-(5-Ethyl-3-phenyl-isoxazole-4-carbonyl)-1H-pyrrole-2-carboxylic acid (intermediate 12) and 2-morpholin-4-yl-ethyl-amine (commercially available) | 423.1 |
| 209 | 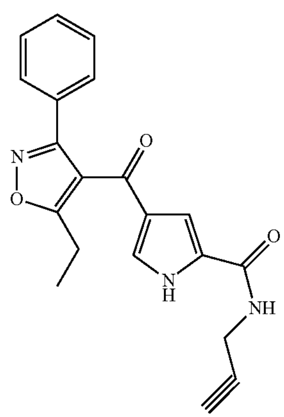 | 4-(5-Ethyl-3-phenyl-isoxazole-4-carbonyl)-1H-pyrrole-2-carboxylic acid prop-2-ynylamide | 4-(5-Ethyl-3-phenyl-isoxazole-4-carbonyl)-1H-pyrrole-2-carboxylic acid (intermediate 12) and prop-2-ynyl-amine (commercially available) | 348.0 |

TABLE 1-continued

| Example No. | Structure | Name | Starting materials | MW found [MH+] |
|---|---|---|---|---|
| 210 | 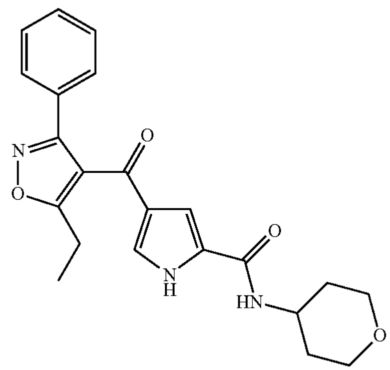 | 4-(5-Ethyl-3-phenyl-isoxazole-4-carbonyl)-1H-pyrrole-2-carboxylic acid (tetrahydro-pyran-4-yl)-amide | 4-(5-Ethyl-3-phenyl-isoxazole-4-carbonyl)-1H-pyrrole-2-carboxylic acid (intermediate 12) and tetrahydro-pyran-4-yl-amine (commercially available) | 394.1 |
| 211 | 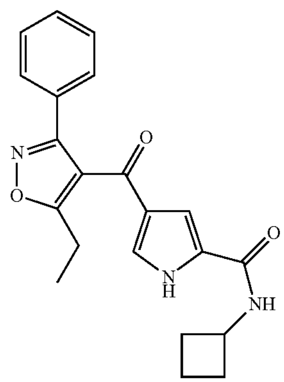 | 4-(5-Ethyl-3-phenyl-isoxazole-4-carbonyl)-1H-pyrrole-2-carboxylic acid cyclobutylamide | 4-(5-Ethyl-3-phenyl-isoxazole-4-carbonyl)-1H-pyrrole-2-carboxylic acid (intermediate 12) and cyclobutyl-amine (commercially available) | 364.1 |

TABLE 1-continued

| Example No. | Structure | Name | Starting materials | MW found [MH+] |
|---|---|---|---|---|
| 212 | 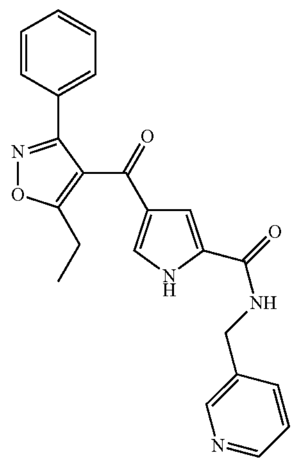 | 4-(5-Ethyl-3-phenyl-isoxazole-4-carbonyl)-1H-pyrrole-2-carboxylic acid (pyridin-3-ylmethyl)-amide | 4-(5-Ethyl-3-phenyl-isoxazole-4-carbonyl)-1H-pyrrole-2-carboxylic acid (intermediate 12) and pyridin-3-ylmethyl-amine (commercially available) | 401.1 |
| 213 | 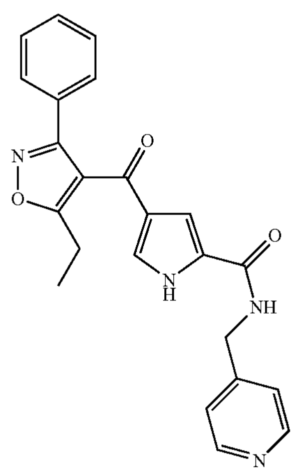 | 4-(5-Ethyl-3-phenyl-isoxazole-4-carbonyl)-1H-pyrrole-2-carboxylic acid (pyridin-4-ylmethyl)-amide | 4-(5-Ethyl-3-phenyl-isoxazole-4-carbonyl)-1H-pyrrole-2-carboxylic acid (intermediate 12) and pyridin-4-ylmethyl-amine (commercially available) | 401.1 |

TABLE 1-continued

| Example No. | Name | Structure | Starting materials | MW found [MH+] |
|---|---|---|---|---|
| 214 | 4-(5-Ethyl-3-phenyl-isoxazole-4-carbonyl)-1H-pyrrole-2-carboxylic acid (3-morpholin-4-yl-propyl)-amide | 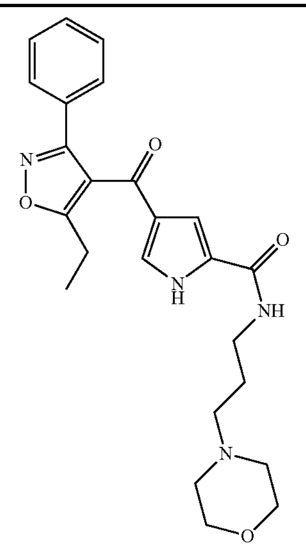 | 4-(5-Ethyl-3-phenyl-isoxazole-4-carbonyl)-1H-pyrrole-2-carboxylic acid (intermediate 12) and 3-morpholin-4-yl-propyl-amine (commercially available) | 437.1 |
| 215 | 4-(5-Ethyl-3-phenyl-isoxazole-4-carbonyl)-1H-pyrrole-2-carboxylic acid cyclopentylamide | 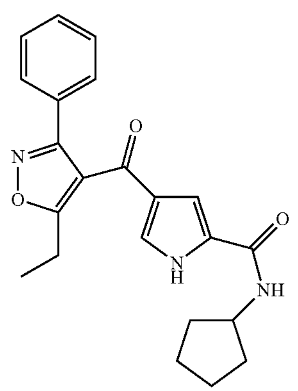 | 4-(5-Ethyl-3-phenyl-isoxazole-4-carbonyl)-1H-pyrrole-2-carboxylic acid (intermediate 12) and cyclopentyl-amine (commercially available) | 378.1 |

TABLE 1-continued

| Example No. | Structure | Name | Starting materials | MW found [MH+] |
|---|---|---|---|---|
| 216 | 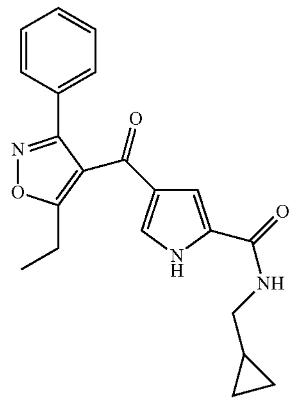 | 4-(5-Ethyl-3-phenyl-isoxazole-4-carbonyl)-1H-pyrrole-2-carboxylic acid cyclopropylmethylamide | 4-(5-Ethyl-3-phenyl-isoxazole-4-carbonyl)-1H-pyrrole-2-carboxylic acid (intermediate 12) and cyclopropylmethyl-amine (commercially available) | 364.1 |
| 217 | 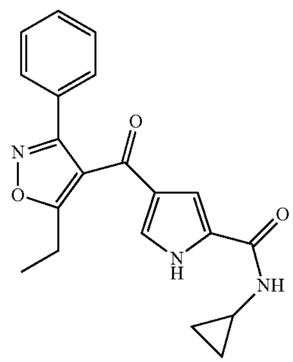 | 4-(5-Ethyl-3-phenyl-isoxazole-4-carbonyl)-1H-pyrrole-2-carboxylic acid cyclopropylamide | 4-(5-Ethyl-3-phenyl-isoxazole-4-carbo-nyl)-1H-pyrrole-2-carboxylic acid (intermediate 12) and cyclopropyl-amine (commercially available) | 350.1 |

TABLE 1-continued

| Example No. | Structure | Name | Starting materials | MW found [MH+] |
|---|---|---|---|---|
| 218 | 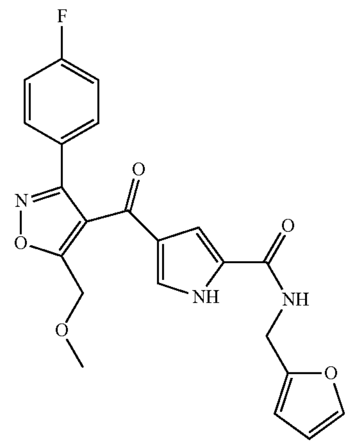 | 4-[3-(4-Fluoro-phenyl)-5-methoxymethyl-isoxazole-4-carbonyl]-1H-pyrrole-2-carboxylic acid (furan-2-ylmethyl)-amide | 4-[3-(4-Fluoro-phenyl)-5-methoxymethyl-isoxazole-4-carbo-nyl]-1H-pyrrole-2-carboxylic acid (intermediate 13) and furan-2-ylmethyl-amine (commercially available) | 424.0 |
| 219 | 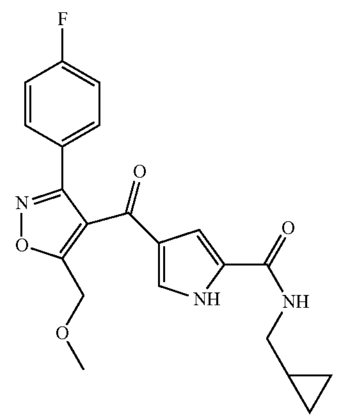 | 4-[3-(4-Fluoro-phenyl)-5-methoxymethyl-isoxazole-4-carbonyl]-1H-pyrrole-2-carboxylic acid cyclopropylmethyl-amide | 4-[3-(4-Fluoro-phenyl)-5-methoxy-methyl-isoxazole-4-carbonyl]-1H-pyrrole-2-carboxylic acid (intermediate 13) and cyclopropylmethyl-amine (commercially available) | 398.1 |

TABLE 1-continued

| Example No. | Structure | Name | Starting materials | MW found [MH+] |
|---|---|---|---|---|
| 220 | 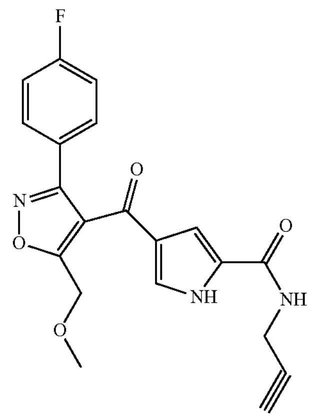 | 4-[3-(4-Fluoro-phenyl)-5-methoxymethyl-isoxazole-4-carbonyl]-1H-pyrrole-2-carboxylic acid prop-2-ynylamide | 4-[3-(4-Fluoro-phenyl)-5-methoxymethyl-isoxazole-4-carbonyl]-1H-pyrrole-2-carboxylic acid (intermediate 13) and prop-2-ynyl-amine (commercially available) | 382.1 |
| 221 | 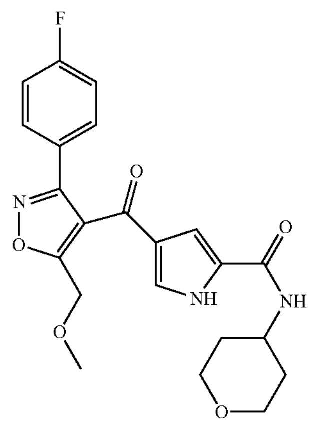 | 4-[3-(4-Fluoro-phenyl)-5-methoxymethyl-isoxazole-4-carbonyl]-1H-pyrrole-2-carboxylic acid (tetrahydro-pyran-4-yl)-amide | 4-[3-(4-Fluoro-phenyl)-5-methoxymethyl-isoxazole-4-carbonyl]-1H-pyrrole-2-carboxylic acid (intermediate 13) and tetrahydro-pyran-4-yl-amine (commercially available) | 428.0 |

TABLE 1-continued

| Example No. | Name | Starting materials | MW found [MH+] |
|---|---|---|---|
| 222 | 4-[3-(4-Fluoro-phenyl)-5-methoxymethyl-isoxazole-4-carbonyl]-1H-pyrrole-2-carboxylic acid (pyridin-3-ylmethyl)-amide | 4-[3-(4-Fluoro-phenyl)-5-methoxymethyl-isoxazole-4-carbonyl]-1H-pyrrole-2-carboxylic acid (intermediate 13) and pyridin-3-ylmethyl-amine (commercially available) | 435.1 |
| 223 | 4-(3,5-Diphenyl-isoxazole-4-carbonyl)-1H-pyrrole-2-carboxylic acid (pyridin-2-ylmethyl)-amide | 4-(3,5-Diphenyl-isoxazole-4-carbonyl)-1H-pyrrole-2-carboxylic acid (intermediate 14) and pyridin-2-ylmethyl-amine (commercially available) | 449.1 |

TABLE 1-continued

| Example No. | Name | Starting materials | MW found [MH⁺] |
|---|---|---|---|
| 224 | 4-(3,5-Diphenyl-isoxazole-4-carbonyl)-1H-pyrrole-2-carboxylic acid (2-morpholin-4-yl-ethyl)-amide | 4-(3,5-Diphenyl-isoxazole-4-carbonyl)-1H-pyrrole-2-carboxylic acid (intermediate 14) and 2-morpholin-4-yl-ethyl-amine (commercially available) | 471.1 |
| 225 | 4-(3,5-Diphenyl-isoxazole-4-carbonyl)-1H-pyrrole-2-carboxylic acid cyclopentylamide | 4-(3,5-Diphenyl-isoxazole-4-carbonyl)-1H-pyrrole-2-carboxylic acid (intermediate 14) and cyclopentyl-amine (commercially available) | 426.1 |

TABLE 1-continued

| Example No. | Structure | Name | Starting materials | MW found [MH+] |
|---|---|---|---|---|
| 226 | 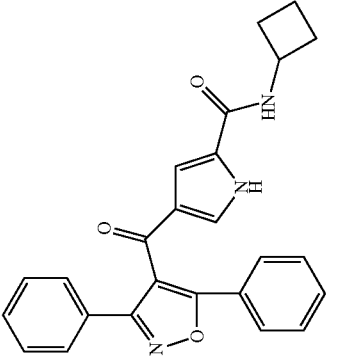 | 4-(3,5-Diphenyl-isoxazole-4-carbonyl)-1H-pyrrole-2-carboxylic acid cyclobutylamide | 4-(3,5-Diphenyl-isoxazole-4-carbonyl)-1H-pyrrole-2-carboxylic acid (intermediate 14) and cyclobutyl-amine (commercially available) | 412.1 |
| 227 | 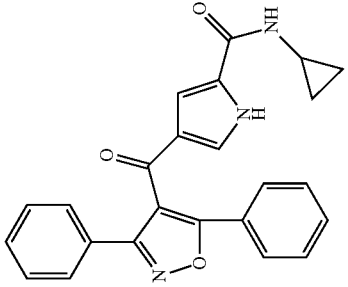 | 4-(3,5-Diphenyl-isoxazole-4-carbonyl)-1H-pyrrole-2-carboxylic acid cyclopropylamide | 4-(3,5-Diphenyl-isoxazole-4-carbonyl)-1H-pyrrole-2-carboxylic acid (intermediate 14) and cyclopropyl-amine (commercially available) | 398.1 |

TABLE 1-continued

| Example No. | Name | Structure | Starting materials | MW found [MH+] |
|---|---|---|---|---|
| 228 | 4-(3,5-Diphenyl-isoxazole-4-carbonyl)-1H-pyrrole-2-carboxylic acid (2-hydroxy-ethyl)-amide | 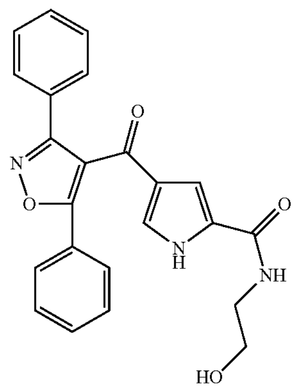 | 4-(3,5-Diphenyl-isoxazole-4-carbonyl)-1H-pyrrole-2-carboxylic acid (intermediate 14) and 2-hydroxy-ethyl-amine (commercially available) | 402.1 |
| 229 | 4-[3-(4-Fluoro-phenyl)-5-methyl-isoxazole-4-carbonyl]-1-methyl-1H-pyrrole-2-carboxylic acid cyclopropylmethyl-amide | 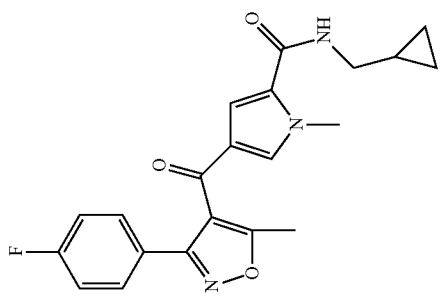 | 4-(5-Methyl-3-(4-phenyl)-isoxazole-4-carbonyl)-1H-pyrrole-2-carboxylic acid cyclopropylmethyl-amide) and methyl iodide (commercially available) | 382.1 |

TABLE 1-continued

| Example No. | Name | Structure | Starting materials | MW found [MH+] |
|---|---|---|---|---|
| 230 | 4-[3-(4-Fluoro-phenyl)-5-methyl-isoxazole-4-carbonyl]-1-methyl-1H-pyrrole-2-carboxylic acid cyclopentylamide | 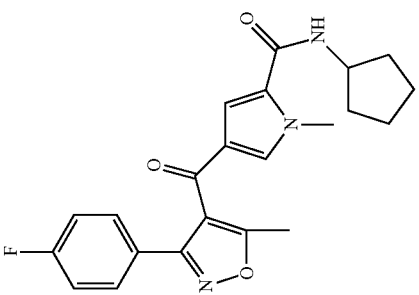 | 4-(5-Methyl-3-(4-fluorophenyl)-isoxazole-4-carbonyl]-1-methyl-1H-pyrrole-2-carboxylic acid (cyclopentyl)-amide) and methyl iodide (commercially available) | 396.1 |
| 231 | 4-[3-(4-Bromo-phenyl)-5-methyl-isoxazole-4-carbonyl]-1-methyl-1H-pyrrole-2-carboxylic acid (tetrahydro-pyran-4-yl)-amide | 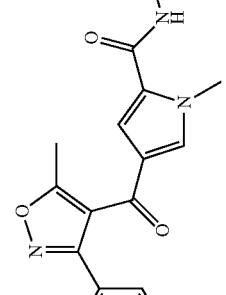 | 4-[3-(4-Bromo-phenyl)-5-methyl-isoxazole-4-carbonyl]-1-methyl-1H-pyrrole-2-carboxylic acid (intermediate 15) and tetrahydro-pyran-4-yl-amine (commercially available) | 472.1/473.9 |
| 232 | 4-[3-(4-Bromo-phenyl)-5-methyl-isoxazole-4-carbonyl]-1-methyl-1H-pyrrole-2-carboxylic acid (3-morpholin-4-yl-propyl)-amide | 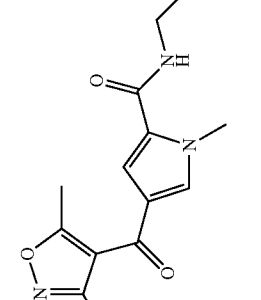 | 4-[3-(4-Bromo-phenyl)-5-methyl-isoxazole-4-carbonyl]-1-methyl-1H-pyrrole-2-carboxylic acid (intermediate 15) and 3-morpholin-4-yl-propyl-amine (commercially available) | 515.4/517.2 |

TABLE 1-continued

| Example No. | Name | Starting materials | MW found [MH+] |
|---|---|---|---|
| 233 | 4-[3-(4-Bromo-phenyl)-5-methyl-isoxazole-4-carbonyl]-1-methyl-1H-pyrrole-2-carboxylic acid cyclopentylamide | 4-[3-(4-Bromo-phenyl)-5-methyl-isoxazole-4-carbonyl]-1-methyl-1H-pyrrole-2-carboxylic acid (intermediate 15) and cyclopentyl-amine (commercially available) | 456.0/458.1 |
| 234 | [3-(4-Bromo-phenyl)-5-methyl-isoxazol-4-yl]-[5-(4-methyl-piperidine-1-carbonyl)-1H-pyrrol-3-yl]-methanone | 4-[3-(4-bromo-phenyl)-5-methyl-isoxazole-4-carbonyl]-1H-pyrrole-2-carboxylic acid (intermediate 2) and 4-methyl-piperidine (commercially available) | 456.2 |
| 235 | {4-[3-(4-Bromo-phenyl)-5-methyl-isoxazole-4-carbonyl]-1H-pyrrol-2-yl}-(2-isopropyl-pyrrolidin-1-yl)-methanone | 4-[3-(4-Bromo-phenyl)-5-methyl-isoxazole-4-carbonyl]-1H-pyrrole-2-carboxylic acid (intermediate 2) and 2-(methylethyl)pyrrolidine (commercially available) | 470.2/472.2 |
| 236 | 4-[3-(4-Bromo-phenyl)-5-methyl-isoxazole-4-carbonyl]-1H-pyrrole-2-carboxylic acid ((R)-1-cyclohexyl-ethyl)-amide | 4-[3-(4-Bromo-phenyl)-5-methyl-isoxazole-4-carbonyl]-1H-pyrrole-2-carboxylic acid (intermediate 2) and (R)-(−)-1-cyclohexylethylamine (commercially available) | 484.3/486.3 |

TABLE 1-continued

| Example No. | Structure | Name | Starting materials | MW found [MH+] |
|---|---|---|---|---|
| 237 | (structure) | 4-[3-(4-Methoxy-phenyl)-5-methyl-isoxazole-4-carbonyl]-1H-pyrrole-2-carboxylic acid cyclopropylmethyl-amide | 4-[3-(4-Methoxy-phenyl)-5-methyl-isoxazole-4-carbonyl]-1H-pyrrole-2-carboxylic acid (intermediate 4) and cyclopropylmethylamine (commercially available) | 380.1 |

Intermediate 16

4-[3-(2-Chloro-phenyl)-5-methyl-isoxazole-4-carbonyl]-1H-pyrrole-2-carboxylic acid

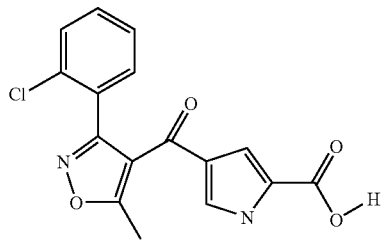

a) Step 1:

4-[3-(2-Chloro-phenyl)-5-methyl-isoxazole-4-carbonyl]-1H-pyrrole-2-carboxylic acid methyl ester

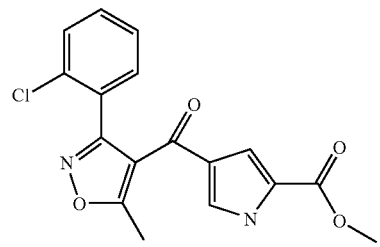

According to the procedure described for the synthesis of 4-[3-(4-bromophenyl-5-methyl-isoxazole-4-carbonyl)-1H-pyrrole-2-carboxylic acid methyl ester (intermediate 2, step 2), 4-[3-(2-Chloro-phenyl)-5-methyl-isoxazole-4-carbonyl]-1H-pyrrole-2-carboxylic acid methyl ester was obtained from 4-(1-oxo-but-2-ynyl)-1-H-pyrrole-2-carboxylic acid methyl ester and 2-chloro-N-hydroxybenzenecarboxymidoyl chloride (commercially available) in 55.0% yield as light brown solid. (m/e): 345.1 ($M^+$; 100%).

b) Step 2:

According to the procedure described for the synthesis of 4-(5-methyl-3-phenyl-isoxazole-4-carbonyl)-1H-pyrrole-2-carboxylic acid (intermediate 1), 4-[3-(2-chloro-phenyl)-5-methyl-isoxazole-4-carbonyl]-1H-pyrrole-2-carboxylic acid (intermediate 16) was synthesized from 4-[3-(2-chloro-phenyl)-5-methyl-isoxazole-4-carbonyl]-1H-pyrrole-2-carboxylic acid methyl ester through saponification with LiOH.$H_2O$. The title compound was obtained in 98% yield as light-yellow solid. (m/e): 331.1 ($M^+$; 100%).

EXAMPLE 238

4-[3-(2-Chloro-phenyl)-5-methyl-isoxazole-4-carbonyl]-1H-pyrrole-2-carboxylic acid (3-fluoro-phenyl)-amide

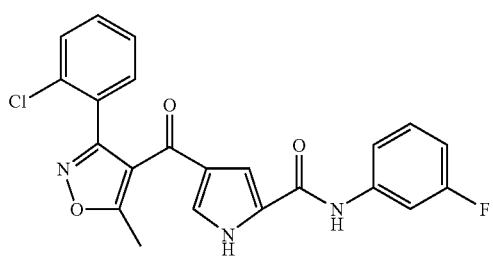

According to the procedure described for the synthesis of 4-(5-methyl-3-phenyl-isoxazole-4-carbonyl)-1H-pyrrole-2-carboxylic acid (pyridin-2-ylmethyl)-amide (example 2) the title compound has been synthesized from 4-[3-(2-Chloro-phenyl)-5-methyl-isoxazole-4-carbonyl]-1H-pyrrole-2-carboxylic acid (intermediate 16) and 3-fluorophenylamine (commercially available). (m/e): 424.2 ($MH^+$; 100%).

EXAMPLE 239

4-[3-(3-Bromo-phenyl)-5-methyl-isoxazole-4-carbonyl]-1H-pyrrole-2-carboxylic acid cyclopropylamide

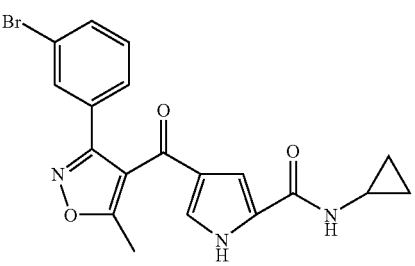

According to the procedure described for the synthesis of 4-(5-methyl-3-phenyl-isoxazole-4-carbonyl)-1H-pyrrole-2-carboxylic acid (pyridin-2-ylmethyl)-amide (example 2) the title compound has been synthesized from 4-[3-(3-bromo-phenyl)-5-methyl-isoxazole-4-carbonyl]-1H-pyrrole-2-carboxylic acid (intermediate 9) and cyclopropylamine (commercially available). (m/e): 412.3 ($MH^+$; 100%).

EXAMPLE 240

4-[3-(2-Chloro-phenyl)-5-methyl-isoxazole-4-carbonyl]-1H-pyrrole-2-carboxylic acid (tetrahydro-pyran-4-yl)-amide

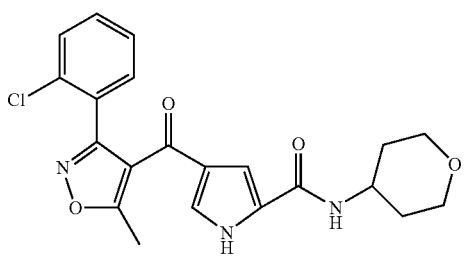

According to the procedure described for the synthesis of 4-(5-methyl-3-phenyl-isoxazole-4-carbonyl)-1H-pyrrole-2-carboxylic acid (pyridin-2-ylmethyl)-amide (example 2) the title compound has been synthesized from 4-[3-(2-Chloro-phenyl)-5-methyl-isoxazole-4-carbonyl]-1H-pyrrole-2-carboxylic acid (intermediate 16) and tetrahydro-pyran-4-ylamine(commercially available). (m/e): 414.7 ($MH^+$; 100%).

EXAMPLE 241

4-[5-Methyl-3-(4-phenoxy-phenyl)-isoxazole-4-carbonyl]-1H-pyrrole-2-carboxylic acid cyclobutylamide

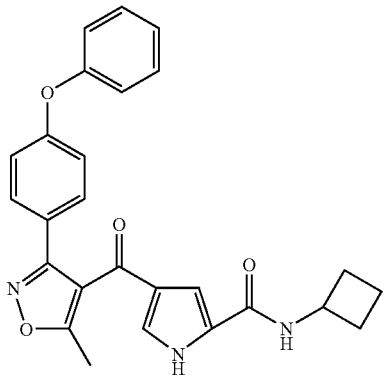

According to the procedure described for the synthesis of 4-(5-methyl-3-phenyl-isoxazole-4-carbonyl)-1H-pyrrole-2-carboxylic acid (pyridin-2-ylmethyl)-amide (example 2) the title compound has been synthesized from 4-[5-methyl-3-(4-phenoxy-phenyl)-isoxazole-4-carbonyl]-1H-pyrrole-2-carboxylic acid (intermediate 10) and cyclobutylamine (commercially available). (m/e): 442.1 (MH+; 100%).

EXAMPLE 242

4-[5-Methyl-3-(4-phenoxy-phenyl)-isoxazole-4-carbonyl]-1H-pyrrole-2-carboxylic acid cyclopentylamide

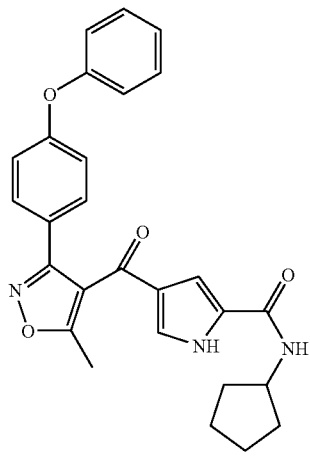

According to the procedure described for the synthesis of 4-(5-methyl-3-phenyl-isoxazole-4-carbonyl)-1H-pyrrole-2-carboxylic acid (pyridin-2-ylmethyl)-amide (example 2) the title compound has been synthesized from 4-[5-methyl-3-(4-phenoxy-phenyl)-isoxazole-4-carbonyl]-1H-pyrrole-2-carboxylic acid (intermediate 10) and cyclopentylamine (commercially available). (m/e): 456.6 (MH+; 100%).

Intermediate 17

4-[3-(2-Chloro-phenyl)-5-methyl-isoxazole-4-carbonyl]-1H-pyrrole-2-carboxylic acid

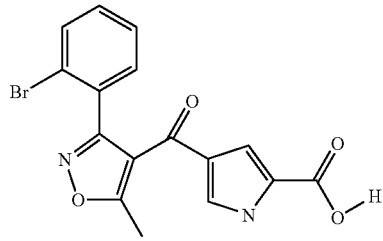

a) Step 1:

4-[3-(2-Bromo-phenyl)-5-methyl-isoxazole-4-carbonyl]-1H-pyrrole-2-carboxylic acid methyl ester

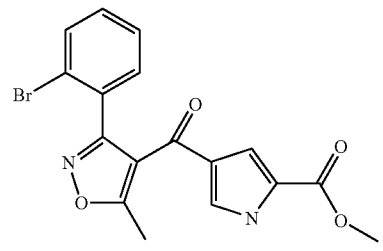

According to the procedure described for the synthesis of 4-[3-(4-bromophenyl-5-methyl-isoxazole-4-carbonyl)-1H-pyrrole-2-carboxylic acid methyl ester (intermediate 2, step 2), 4-[3-(2-bromo-phenyl)-5-methyl-isoxazole-4-carbonyl]-1H-pyrrole-2-carboxylic acid methyl ester was obtained from 4-(1-oxo-but-2-ynyl)-1-H-pyrrole-2-carboxylic acid methyl ester and 2-bromo-N-hydroxybenzenecarboxymidoyl chloride (commercially available) in 41.3% yield as light brown solid. (m/e): 388.9 (M+; 100%).

b) Step 2:

According to the procedure described for the synthesis of 4-(5-methyl-3-phenyl-isoxazole-4-carbonyl)-1H-pyrrole-2-carboxylic acid (intermediate 1), 4-[3-(2-bromo-phenyl)-5-methyl-isoxazole-4-carbonyl]-1H-pyrrole-2-carboxylic acid (intermediate 16) was synthesized from 4-[3-(2-bromo-phenyl)-5-methyl-isoxazole-4-carbonyl]-1H-pyrrole-2-carboxylic acid methyl ester through saponification with LiOH.H2O. The title compound was obtained in 88.1% yield as light-yellow solid. (m/e): 374.9 (M+; 100%).

EXAMPLE 243

4-[3-(2-Bromo-phenyl)-5-methyl-isoxazole-4-carbonyl]-1H-pyrrole-2-carboxylic acid methyl-prop-2-ynyl-amide

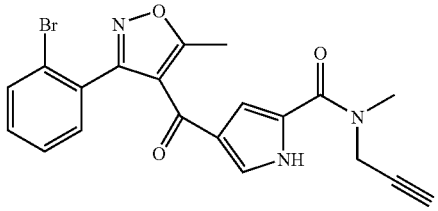

According to the procedure described for the synthesis of 4-(5-Methyl-3-phenyl-isoxazole-4-carbonyl)-1H-pyrrole-2-carboxylic acid (pyridin-2-ylmethyl)-amide (example 2) the title compound has been synthesized from 4-[3-(2-Chloro-phenyl)-5-methyl-isoxazole-4-carbonyl]-1H-pyrrole-2-carboxylic acid (intermediate 17) and methyl-prop-2-ynylamine (commercially available). (m/e): 426.2 (MH+; 100%).

EXAMPLE 244

4-[3-(4-Benzyloxy-phenyl)-5-methyl-isoxazole-4-carbonyl]-1H-pyrrole-2-carboxylic acid cyclopropyl-methyl-amide

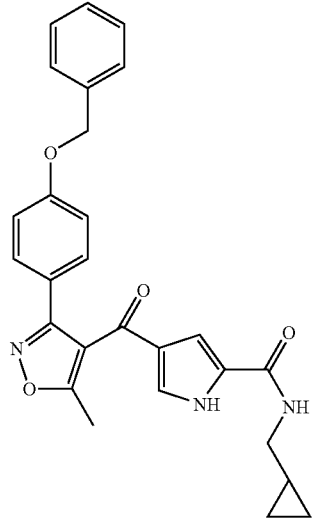

According to the procedure described for the synthesis of 4-(5-methyl-3-phenyl-isoxazole-4-carbonyl)-1H-pyrrole-2-carboxylic acid (pyridin-2-ylmethyl)-amide (example 2) the title compound has been synthesized from 4-[3-(4-benzyloxy-phenyl)-5-methyl-isoxazole-4-carbonyl]-1H-pyrrole-2-carboxylic acid (intermediate 11) and cyclopropylmethylamine (commercially available). (m/e): 442.2 (MH+; 100%).

Intermediate 18

4-[3-(3,4,5-trifluoro-phenyl)-5-methyl-isoxazole-4-carbonyl]-2-trichloroacetyl-1H-pyrrole

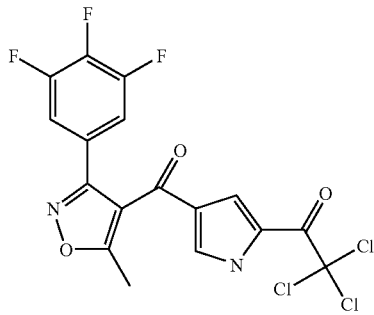

a) Step 1:

5-Methyl [3-(3,4,5-fluoro-phenyl)-isoxazole-4-carboxylic acid

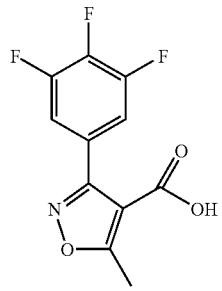

According to the procedure described for the synthesis of 5-ethyl-3-phenyl-isoxazole-4-carboxylic acid (intermediate 12, step 1), 5-Methyl [3-(3,4,5-fluoro-phenyl)-isoxazole-4-carboxylic acid was synthesized from 5-Methyl [3-(3,4,5-fluoro-phenyl)-isoxazole-4-carboxylic acid ethyl ester (prepared according to: Synthesis 2003; 1347-1356) in 53.7% yield as light yellow solid. (m/e): 258.5 (M+1; 100%).

b) Step 2:

According to the procedure described for the synthesis of 4-(5-methyl-3-(4-fluorophenyl)-isoxazole-4-carbonyl)-2-trichloroacetyl-1H-pyrrole (example 229, step 1), 4-[3-(3,4,5-trifluoro-phenyl)-5-methyl-isoxazole-4-carbonyl]-2-trichloroacetyl-1H-pyrrole (intermediate 18) was synthesized from 5-methyl [3-(3,4,5-fluoro-phenyl)-isoxazole-4-carboxylic acid in 47.1% yield as light-yellow solid. (m/e): 452.3 (M+1; 100%).

EXAMPLE 245

4-[5-Methyl-3-(3,4,5-trifluoro-phenyl)-isoxazole-4-carbonyl]-1H-pyrrole-2-carboxylic acid cyclopenty-lamide

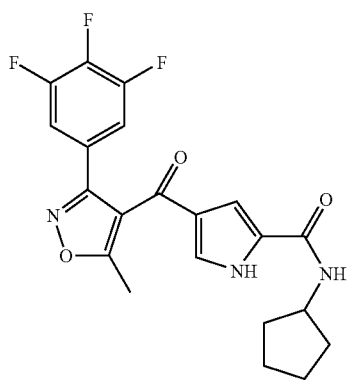

According to the procedure described for the synthesis of 4-(5-methyl-3-(4-fluorophenyl)-isoxazole-4-carbonyl)-1H-pyrrole-2-carboxylic acid (cyclopropylmethyl)-amide (example 229, step 2), the title compound has been synthesized from 4-[3-(3,4,5-trifluoro-phenyl)-5-methyl-isoxazole-4-carbonyl]-2-trichloroacetyl-1H-pyrrole (intermediate 18) and cyclopentylamine (commercially available) in 49.6 yield. (m/e): 418.3 (MH+; 100%).

EXAMPLE 246

1-Methyl-4-(5-methyl-3-phenyl-isoxazole-4-carbonyl)-1H-pyrrole-2-carboxylic acid cyclopropylmethyl-amide

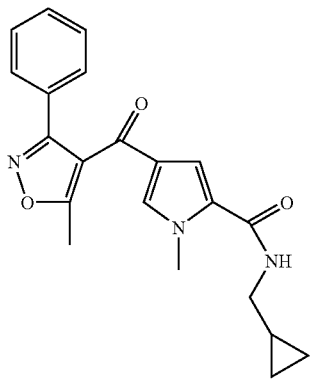

According to the procedure described for the synthesis of 4-(5-methyl-3-(4-fluorophenyl)-isoxazole-4-carbonyl)-1-methyl-pyrrole-2-carboxylic acid (cyclopropylmethyl)-amide (Example 229, step 3), 4-(5-methyl-3-phenyl-isoxazole-4-carbonyl)-1-methyl-pyrrole-2-carboxylic acid (cyclopropylmethyl)-amide was synthesized from 4-(5-methyl-3-phenyl-isoxazole-4-carbonyl)-1H-pyrrole-2-carboxylic acid (cyclopropylmethyl)-amide (example 12) in 31.7% yield as white solid. (m/e): 364.6 (M+1; 100%).

EXAMPLE 247

1-Methyl-4-(5-methyl-3-phenyl-isoxazole-4-carbonyl)-1H-pyrrole-2-carboxylic acid cyclopentylamide

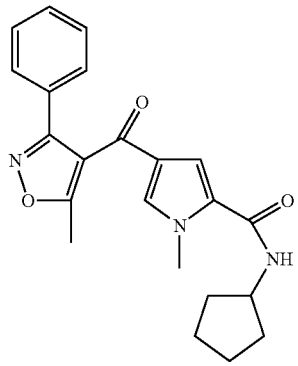

According to the procedure described for the synthesis of 4-(5-methyl-3-(4-fluorophenyl)-isoxazole-4-carbonyl)-1-methyl-pyrrole-2-carboxylic acid (cyclopropylmethyl)-amide (Example 229, step 3), 4-(5-methyl-3-phenyl-isoxazole-4-carbonyl)-1-methyl-pyrrole-2-carboxylic acid (cyclopentyl)-amide was synthesized from 4-(5-methyl-3-phenyl-isoxazole-4-carbonyl)-1H-pyrrole-2-carboxylic acid (cyclopentyl)-amide in 38.7% yield as white solid. (m/e): 378.3 (M+1; 100%).

EXAMPLE 248

4-[5-methyl-3-(3-Fluoro-phenyl)-isoxazole-4-carbonyl]-1-methyl-1H-pyrrole-2-carboxylic acid cyclopropylmethyl-amide

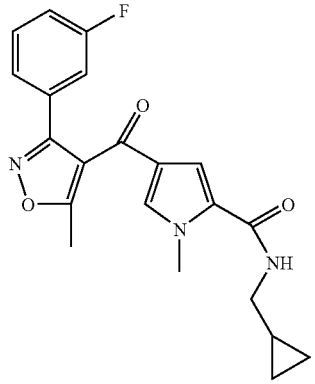

According to the procedure described for the synthesis of 4-(5-methyl-3-(4-fluorophenyl)-isoxazole-4-carbonyl)-1-methyl-pyrrole-2-carboxylic acid (cyclopropylmethyl)-amide (Example 229, step 3), 4-[5-methyl-3-(3-fluorophenyl)-isoxazole-4-carbonyl)-1-methyl-pyrrole-2-carboxylic acid (cyclopropylmethyl)-amide was synthesized from 4-[5-methyl-3-(3-fluorophenyl)-isoxazole-4-carbonyl]-1H-pyrrole-2-carboxylic acid (cyclopropylmethyl)-amide in 27% yield as white solid. (m/e): 382.3 (M+1; 100%).

EXAMPLE 249

4-[3-(3-Fluoro-phenyl)-5-methyl-isoxazole-4-carbonyl]-1-methyl-1H-pyrrole-2-carboxylic acid prop-2-ynylamide

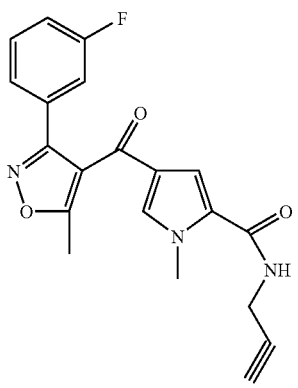

According to the procedure described for the synthesis of 4-(5-methyl-3-(4-fluorophenyl)-isoxazole-4-carbonyl)-1-methyl-pyrrole-2-carboxylic acid (cyclopropylmethyl)-amide (Example 229, step 3), the title compound was synthesized from 4-[5-methyl-3-(3-fluorophenyl)-isoxazole-4-carbonyl)-1H-pyrrole-2-carboxylic acid prop-2-ynylamide (example 179) in 43% yield as white solid. (m/e): 366.1 (M+1; 100%).

EXAMPLE 250

4-[3-(3-Fluoro-phenyl)-5-methyl-isoxazole-4-carbonyl]-1-methyl-1H-pyrrole-2-carboxylic acid cyclopentylamide

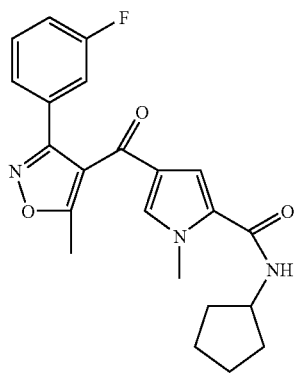

According to the procedure described for the synthesis of 4-(5-methyl-3-(4fluorophenyl)-isoxazole-4-carbonyl)-1-methyl-pyrrole-2-carboxylic acid (cyclopropylmethyl)-amide (Example 229, step 3), the title compound was synthesized from 4-[5-methyl-3-(3-fluorophenyl)-isoxazole-4-carbonyl)-1H-pyrrole-2-carboxylic acid cyclopentylamide (example 178) in 27.6% yield as white solid. (m/e): 396.2 (M+1; 100%).

EXAMPLE 251

4-[3-(3-Fluoro-phenyl)-5-methyl-isoxazole-4-carbonyl]-1-methyl-1H-pyrrole-2-carboxylic acid cyclobutylamide

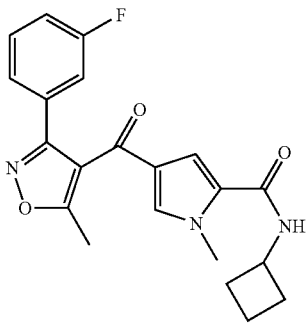

According to the procedure described for the synthesis of 4-(5-methyl-3-(4-fluorophenyl)-isoxazole-4-carbonyl)-1-methyl-pyrrole-2-carboxylic acid (cyclopropylmethyl)-amide (Example 229, step 3), the title compound was synthesized from 4-[5-methyl-3-(3-fluorophenyl)-isoxazole-4-carbonyl)-1H-pyrrole-2-carboxylic acid cyclobutylamide (example 174) in 34.2% yield as white solid. (m/e): 382.1 (M+1; 100%).

Intermediate 19

4-[3-(3,4-difluoro-phenyl)-5-methyl-isoxazole-4-carbonyl]-2-trichloroacetyl-1H-pyrrole

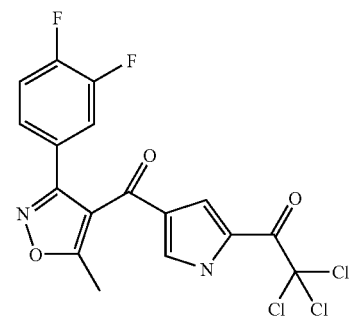

a) Step 1:

5-Ethyl-3-(3,4-diphenyl)l-isoxazole-4-carboxylic acid

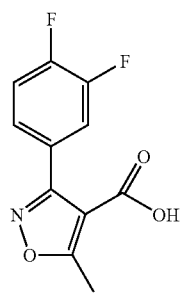

According to the procedure described for the synthesis of 5-ethyl-3-phenyl-isoxazole-4-carboxylic acid (intermediate 12, step 1), 5-methyl-3-(3,4-difluorophenyl)l-isoxazole-4-carboxylic acid was synthesized from 5-methyl-3-(3,4-difluorophenyl)-isoxazole-4-carboxylic acid ethyl ester (prepared according to: Synthesis 2003; 1347-1356) in 25% yield as yellow solid. (m/e): 240.1 (M+1; 100%).

b) Step 2:

According to the procedure described for the synthesis of 4-(5-methyl-3-(4-fluorophenyl)-isoxazole-4-carbonyl)-2-trichloroacetyl-1H-pyrrole (example 229, step 1), 4-[3-(3,4-difluoro-phenyl)-5-methyl-isoxazole-4-carbonyl]-2-trichloroacetyl-1H-pyrrole (intermediate 18) was synthesized from 5-methyl [3-(3,4-diflurorophenyl)-isoxazole-4-carboxylic acid in 46.0% yield as yellow solid. (m/e): 433.0 (M+1; 100%).

EXAMPLE 252

4-[3-(3,4-Difluoro-phenyl)-5-methyl-isoxazole-4-carbonyl]-1H-pyrrole-2-carboxylic acid cyclopropylmethyl-amide

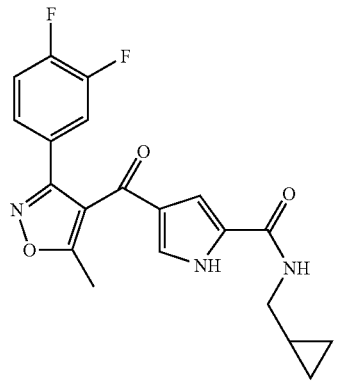

According to the procedure described for the synthesis of 4-(5-methyl-3-(4-fluorophenyl)-isoxazole-4-carbonyl)-1H-pyrrole-2-carboxylic acid (cyclopropylmethyl)-amide (example 229, step 2), the title compound has been synthesized from 4-[3-(3,4-difluoro-phenyl)-5-methyl-isoxazole-4-carbonyl]-2-trichloroacetyl-1H-pyrrole (intermediate 19) and cyclopropylmethylamine (commercially available) in 35.8 yield. (m/e): 386.1 (MH$^+$; 100%).

EXAMPLE 253

4-[3-(3,4-Difluoro-phenyl)-5-methyl-isoxazole-4-carbonyl]-1H-pyrrole-2-carboxylic acid prop-2-ynylamide

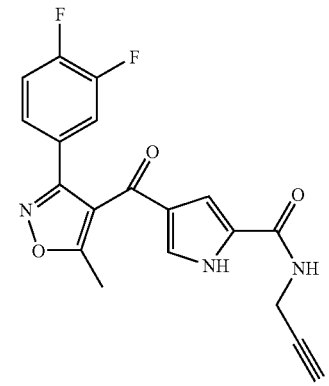

According to the procedure described for the synthesis of 4-(5-methyl-3-(4-fluorophenyl)-isoxazole-4-carbonyl)-1H-pyrrole-2-carboxylic acid (cyclopropylmethyl)-amide (example 229, step 2), the title compound has been synthesized from 4-[3-(3,4-difluoro-phenyl)-5-methyl-isoxazole-4-carbonyl]-2-trichloroacetyl-1H-pyrrole (intermediate 19) and prop-2-ynylamine (commercially available) in 28.1 yield. (m/e): 370.0 (MH$^+$; 100%).

EXAMPLE 254

4-[3-(3,4-Difluoro-phenyl)-5-methyl-isoxazole-4-carbonyl]-1H-pyrrole-2-carboxylic acid (tetrahydro-pyran-4-yl)-amide

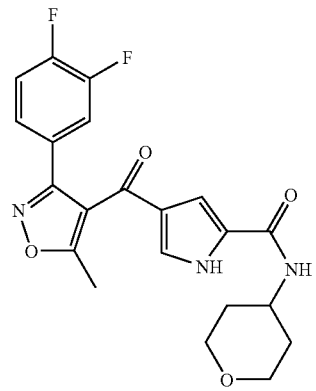

According to the procedure described for the synthesis of 4-(5-methyl-3-(4-fluorophenyl)-isoxazole-4-carbonyl)-1H-pyrrole-2-carboxylic acid (cyclopropylmethyl)-amide (example 229, step 2), the title compound has been synthesized from 4-[3-(3,4-difluoro-phenyl)-5-methyl-isoxazole-4-carbonyl]-2-trichloroacetyl-1H-pyrrole (intermediate 19) and tetrahydro-pyran-4-yl amine(commercially available) in 41.5 yield. (m/e): 416.1 (MH$^+$; 100%).

EXAMPLE 255

4-[3-(3,4-Difluoro-phenyl)-5-methyl-isoxazole-4-carbonyl]-1H-pyrrole-2-carboxylic acid cyclopentylamide

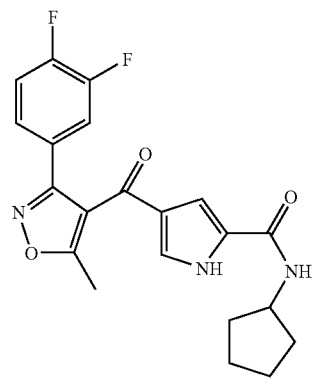

According to the procedure described for the synthesis of 4-(5-methyl-3-(4-fluorophenyl)-isoxazole-4-carbonyl)-1H-pyrrole-2-carboxylic acid (cyclopropylmethyl)-amide (example 229, step 2), the title compound has been synthesized from 4-[3-(3,4-difluoro-phenyl)-5-methyl-isoxazole-4-carbonyl]-2-trichloroacetyl-1H-pyrrole (intermediate 19) and cyclopentylamine (commercially available) in 38.1 yield. (m/e): 400.1 (MH$^+$; 100%).

The invention claimed is:
1. An aryl-isoxazole-4-carbonyl-pyrrole-2-carboxylic acid amide derivative of formula

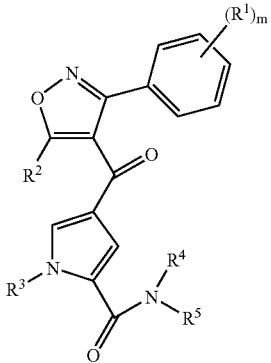

wherein
R$^1$ is hydrogen, halogen, lower alkoxy, phenyloxy or benzyloxy;
R$^2$ is lower alkyl, (CH$_2$)$_n$—O-lower alkyl or phenyl;
R$^3$ is hydrogen or lower alkyl;
R$^4$ and R$^5$ are each independently
  hydrogen,
  lower alkyl,
  lower alkyl substituted by halogen,
  lower alkynyl,
  —(CHR)$_n$-aryl, unsubstituted or substituted by halogen, lower alkyl or lower alkoxy,
  —(CH$_2$)$_n$-non aromatic heterocyclic ring, unsubstituted or substituted by one or two lower alkyl groups,
  —(CH$_2$)$_n$-aromatic heterocyclic rings,
  —(CR$_2$)$_n$-cycloalkyl, unsubstituted or substituted by one to three substituents, selected from the group consisting of hydroxy or lower alkyl,
  —(CHR)$_n$—O-lower alkyl,
  —(CR$_2$)$_n$—OH, or
  —(CHR)$_n$—NR'R",
or R$^4$ and R$^5$ together with the N-atom to which they are attached form the ring
  8-aza-bicyclo[3.2.1]octane, substituted by hydroxy, or 3,4-dihydro-1H-isoquinoline, or
  a non aromatic heterocyclic ring, unsubstituted or substituted by one or two substituents, selected from the group consisting of C(O)O-lower alkyl, lower alkyl, lower alkyl substituted by halogen, cycloalkyl, hydroxy, halogen, N(R)C(O)-lower alkyl, —(CH$_2$)$_n$—O-lower alkyl, or by an aromatic heterocyclic ring;
R is hydrogen, hydroxy, or lower alkyl, wherein when there are two R groups, each R can be the same or different;
R' and R" are each independently hydrogen or lower alkyl;
n is 0, 1, 2, 3 or 4; and
m is 1, 2 or 3;
or a pharmaceutically acceptable acid addition salt thereof.
2. The compound of claim 1, wherein R$^4$ and R$^5$ together with the N-atom to which they are attached do not form a heterocyclic ring.
3. The compound of claim 2, in which R$^1$ is hydrogen or halogen, R$^2$ is methyl, ethyl or CH$_2$OCH$_3$, R$^3$ is hydrogen or methyl and R$^4$ and R$^5$ do not form together with the N atom a heterocyclic ring.
4. The compound of claim 3, wherein R$^5$ is (CR$_2$)$_n$-cycloalkyl.
5. The compound of claim 4, wherein R$^1$ is hydrogen, R$^2$ is methyl or ethyl, R$^3$ and R$^4$ are hydrogen and R$^5$ is (CR$_2$)$_n$-cycloalkyl, unsubstituted or substituted by one to three substituents selected from the group consisting of hydroxy and lower alkyl.
6. The compound of claim 5, selected from the group consisting of
  4-(5-methyl-3-phenyl-isoxazole-4-carbonyl)-1H-pyrrole-2-carboxylic acid cyclopropylmethyl-amide,
  4-(5-methyl-3-phenyl-isoxazole-4-carbonyl)-1H-pyrrole-2-carboxylic acid cyclobutylamide,
  4-(5-ethyl-3-phenyl-isoxazole-4-carbonyl)-1H-pyrrole-2-carboxylic acid cyclopentylamide,
  4-(5-ethyl-3-phenyl-isoxazole-4-carbonyl)-1H-pyrrole-2-carboxylic acid cyclopropylmethyl-amide and
  4-(5-ethyl-3-phenyl-isoxazole-4-carbonyl)-1H-pyrrole-2-carboxylic acid cyclopropylamide.
7. The compound of claim 4, wherein R$^1$ is Br, Cl or F, R$^2$ is methyl, R$^3$ and R$^4$ are hydrogen, and R$^5$ is (CR$_2$)$_n$-cycloalkyl, unsubstituted or substituted by one to three substituents selected from the group consisting of hydroxy and lower alkyl.
8. The compound of claim 7, selected from the group consisting of
  4-[3-(4-bromo-phenyl)-5-methyl-isoxazole-4-carbonyl]-1H-pyrrole-2-carboxylic acid (4-hydroxy-cyclohexyl)-amide,
  4-[3-(4-fluoro-phenyl)-5-methyl-isoxazole-4-carbonyl]-1H-pyrrole-2-carboxylic acid cyclopentylamide,
  4-[3-(4-fluoro-phenyl)-5-methyl-isoxazole-4-carbonyl]-1H-pyrrole-2-carboxylic acid cyclopropylamide,
  4-[3-(4-fluoro-phenyl)-5-methyl-isoxazole-4-carbonyl]-1H-pyrrole-2-carboxylic acid cyclobutylamide,
  4-[3-(4-chloro-phenyl)-5-methyl-isoxazole-4-carbonyl]-1H-pyrrole-2-carboxylic acid cyclopentylamide,
  4-[3-(4-chloro-phenyl)-5-methyl-isoxazole-4-carbonyl]-1H-pyrrole-2-carboxylic acid cyclopropylamide,
  4-[3-(4-chloro-phenyl)-5-methyl-isoxazole-4-carbonyl]-1H-pyrrole-2-carboxylic acid cyclopropylmethyl-amide,
  4-[3-(2-fluoro-phenyl)-5-methyl-isoxazole-4-carbonyl]-1H-pyrrole-2-carboxylic acid cyclopentylamide,
  4-[3-(3-fluoro-phenyl)-5-methyl-isoxazole-4-carbonyl]-1H-pyrrole-2-carboxylic acid cyclopentylamide and
  4-[3-(3,4-difluoro-phenyl)-5-methyl-isoxazole-4-carbonyl]-1H-pyrrole-2-carboxylic acid cyclopentylamide.
9. The compound of claim 2, wherein R$^5$ is (CR$_2$)$_n$—OH or (CR$_2$)$_n$—O-lower alkyl.
10. The compound of claim 9, wherein R$^5$ is (CR$_2$)$_n$OH.
11. The compound of claim 10, wherein R$^1$ is Cl or F, R$^2$ is methyl, R$^3$ and R$^4$ are hydrogen, and R$^5$ is (CR$_2$)$_n$—OH.
12. The compound of claim 11, selected from the group consisting of
  4-[3-(4-fluoro-phenyl)-5-methyl-isoxazole-4-carbonyl]-1H-pyrrole-2-carboxylic acid (2-hydroxy-ethyl)-amide and
  4-[3-(4-chloro-phenyl)-5-methyl-isoxazole-4-carbonyl]-1H-pyrrole-2-carboxylic acid (2-hydroxy-ethyl)-amide.
13. The compound of claim 2, wherein R$^5$ is lower alkyl, lower alkyl substituted by halogen, or lower alkynyl.
14. The compound of claim 13, wherein R$^5$ is lower alkyl or lower alkynyl.
15. The compound of claim 14, wherein R$^1$ is Br, Cl or F, R$^2$ is methyl, R$^3$ and R$^4$ are hydrogen and R$^5$ is lower alkyl or alkynyl.

16. The compound of claim 15, selected from the group consisting of
 4-[3-(4-Bromo-phenyl)-5-methyl-isoxazole-4-carbonyl]-1H-pyrrole-2-carboxylic acid isopropylamide,
 4-[3-(4-Fluoro-phenyl)-5-methyl-isoxazole-4-carbonyl]-1H-pyrrole-2-carboxylic acid prop-2-ynylamide and
 4-[3-(4-Chloro-phenyl)-5-methyl-isoxazole-4-carbonyl]-1H-pyrrole-2-carboxylic acid prop-2-ynylamide.

17. The compound of claim 2, wherein $R^5$ is $(CH_2)_n$-non-aromatic heterocyclic ring, unsubstituted or substituted by one or two lower alkyl groups.

18. The compound of claim 17, wherein $R^1$ is hydrogen, $R^2$ is methyl or ethyl, $R^3$ and $R^4$ are hydrogen and $R^5$ is $(CH_2)_n$-non aromatic heterocyclic ring, unsubstituted or substituted by one or two lower alkyl groups.

19. The compound of claim 18, selected from the group consisting of
 4-(5-methyl-3-phenyl-isoxazole-4-carbonyl)-1H-pyrrole-2-carboxylic acid (tetrahydro-pyran-4-yl)-amide and
 4-(5-ethyl-3-phenyl-isoxazole-4-carbonyl)-1H-pyrrole-2-carboxylic acid (tetrahydro-pyran-4-yl)-amide.

20. The compound of claim 17, wherein $R^1$ is Br, $R^2$ is methyl, $R^3$ is methyl, $R^4$ is hydrogen and $R^5$ is $(CH_2)_n$-non aromatic heterocyclic ring, unsubstituted or substituted by one or two lower alkyl groups.

21. The compound of claim 20, selected from the group consisting of
 4-[3-(4-bromo-phenyl)-5-methyl-isoxazole-4-carbonyl]-1-methyl-1H-pyrrole-2-carboxylic acid (tetrahydro-pyran-4-yl)-amide and
 4-[3-(4-bromo-phenyl)-5-methyl-isoxazole-4-carbonyl]-1-methyl-1H-pyrrole-2-carboxylic acid (3-morpholin-4-yl-propyl)-amide.

22. The compound of claim 17, wherein $R^1$ is Br, Cl or F, $R^2$ is methyl or $CH_2OCH_3$, $R^3$ and $R^4$ are hydrogen and $R^5$ is $(CH_2)_n$-non aromatic heterocyclic ring, unsubstituted or substituted by one or two lower alkyl groups.

23. The compound claim 22, selected from the group consisting of
 4-[3-(4-bromo-phenyl)-5-methyl-isoxazole-4-carbonyl]-1H-pyrrole-2-carboxylic acid (tetrahydro-pyran-4-yl)-amide,
 4-[3-(4-bromo-phenyl)-5-methyl-isoxazole-4-carbonyl]-1H-pyrrole-2-carboxylic acid (2,2-dimethyl-tetrahydro-pyran-4-yl)-amide,
 4-[3-(4-fluoro-phenyl)-5-methyl-isoxazole-4-carbonyl]-1H-pyrrole-2-carboxylic acid (tetrahydro-pyran-4-yl)-amide,
 4-[3-(4-chloro-phenyl)-5-methyl-isoxazole-4-carbonyl]-1H-pyrrole-2-carboxylic acid (tetrahydro-pyran-4-yl)-amide,
 4-[3-(2-fluoro-phenyl)-5-methyl-isoxazole-4-carbonyl]-1H-pyrrole-2-carboxylic acid (tetrahydro-pyran-4-yl)-amide,
 4-[3-(4-fluoro-phenyl)-5-methoxymethyl-isoxazole-4-carbonyl]-1H-pyrrole-2-carboxylic acid (tetrahydro-pyran-4-yl)-amide and
 4-[3-(3,4-difluoro-phenyl)-5-methyl-isoxazole-4-carbonyl]-1H-pyrrole-2-carboxylic acid (tetrahydro-pyran-4-yl)-amide.

24. The compound of claim 2, wherein $R^5$ is $(CH_2)_n$-aromatic heterocyclic rings.

25. The compound of claim 24, wherein $R^1$ is Cl or F, $R^2$ is methyl, $R^3$ and $R^4$ are hydrogen and $R^5$ is $(CH_2)_n$-aromatic heterocyclic ring.

26. The compound of claim 25, selected from the group consisting of
 4-[3-(4-Fluoro-phenyl)-5-methyl-isoxazole-4-carbonyl]-1H-pyrrole-2-carboxylic acid [2-(1H-imidazol-4-yl)-ethyl]-amide,
 4-[3-(4-Fluoro-phenyl)-5-methyl-isoxazole-4-carbonyl]-1H-pyrrole-2-carboxylic acid (furan-2-ylmethyl)-amide,
 4-[3-(4-Chloro-phenyl)-5-methyl-isoxazole-4-carbonyl]-1H-pyrrole-2-carboxylic acid (furan-2-ylmethyl)-amide and
 4-[3-(4-Chloro-phenyl)-5-methyl-isoxazole-4-carbonyl]-1H-pyrrole-2-carboxylic acid [2-(1H-imidazol-4-yl)-ethyl]-amide.

27. The compound of claim 1, wherein $R^5$ is hydrogen.

28. The compound of claim 1, wherein $R^5$ is $(CHR)_n$-aryl, unsubstituted or substituted by halogen, lower alkyl, or lower alkoxy.

29. The compound of claim 1, wherein $R^5$ is $(CHR))_n$—NR'R''.

30. The compound of claim 1, wherein $R^4$ and $R^5$ together with the N-atom to which they are attached form
 8-aza-bicyclo[3.2.1]octane, substituted by hydroxy, or
 3,4-dihydro-1H-isoquinoline, or
 a non aromatic heterocyclic ring, unsubstituted or substituted by one or two substituents, selected from the group consisting of C(O)O-lower alkyl, lower alkyl, lower alkyl substituted by halogen, cycloalkyl, hydroxy, halogen, N(R)C(O)-lower alkyl, —$(CH_2)_n$—O-lower alkyl, or by an aromatic heterocyclic ring.

31. The compound of claim 30, wherein $R^1$ is hydrogen or halogen, $R^2$ is methyl, ethyl, or $CH_2OCH_3$, and $R^3$ is hydrogen or methyl.

32. A pharmaceutical composition comprising a therapeutically effective amount of a compound of formula I

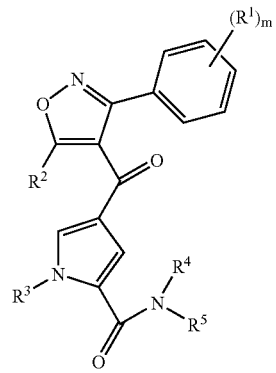

wherein
 $R^1$ is hydrogen, halogen, lower alkoxy, phenyloxy or benzyloxy;
 $R^2$ is lower alkyl, $(CH_2)_n$—O-lower alkyl or phenyl;
 $R^3$ is hydrogen or lower alkyl;
 $R^4$ and $R^5$ are each independently
  hydrogen,
  lower alkyl,
  lower alkyl substituted by halogen,
  lower alkynyl,
  —$(CHR)_n$-aryl, unsubstituted or substituted by halogen, lower alkyl or lower alkoxy,
  —$(CH_2)_n$-non aromatic heterocyclic ring, unsubstituted or substituted by one or two lower alkyl groups,
  —$(CH_2)_n$-aromatic heterocyclic rings, —(CR$_2$)$_n$-cycloalkyl, unsubstituted or substituted by one to three substituents, selected from the group consisting of hydroxy or lower alkyl,
—(CHR)$_n$—O-lower alkyl,
—(CR$_2$)$_n$—OH, or
—(CHR)$_n$—NR'R", or R$^4$ and R$^5$ together with the N-atom to which they are attached form the ring 8-aza-bicyclo[3.2.1]octane, substituted by hydroxy, or 3,4-dihydro-1H-isoquinoline, or a non aromatic heterocyclic ring, unsubstituted or substituted by one or two substituents, selected from the group consisting of C(O)O-lower alkyl, lower alkyl, lower alkyl substituted by halogen, cycloalkyl, hydroxy, halogen, N(R)C(O)-lower alkyl, —(CH$_2$))$_n$—O-lower alkyl, or by an aromatic heterocyclic ring;

R is hydrogen, hydroxy, or lower alkyl, wherein when there are two R groups, each R can be the same or different;

R' and R" are each independently hydrogen or lower alkyl;

n is 0, 1, 2, 3 or 4; and m is 1, 2 or 3;

or a pharmaceutically acceptable acid addition salt thereof and a pharmaceutically acceptable carrier.

* * * * *